(12) United States Patent
Brynolfsson et al.

(10) Patent No.: US 12,597,127 B2
(45) Date of Patent: Apr. 7, 2026

(54) SYSTEMS AND METHODS FOR AUTOMATED IDENTIFICATION AND CLASSIFICATION OF LESIONS IN LOCAL LYMPH AND DISTANT METASTASES

(71) Applicant: EXINI Diagnostics AB, Lund (SE)

(72) Inventors: Johan Martin Brynolfsson, Helsingborg (SE); Hannicka Maria Eleonora Sahlstedt, Malmö (SE); Jens Filip Andreas Richter, Lund (SE)

(73) Assignee: EXINI Diagnostics AB, Lund (SE)

( * ) Notice: Subject to any disclaimer, the term of this patent is extended or adjusted under 35 U.S.C. 154(b) by 697 days.

(21) Appl. No.: 17/959,357

(22) Filed: Oct. 4, 2022

(65) Prior Publication Data

US 2023/0115732 A1 Apr. 13, 2023

Related U.S. Application Data

(60) Provisional application No. 63/336,998, filed on Apr. 29, 2022, provisional application No. 63/253,709, filed on Oct. 8, 2021.

(51) Int. Cl.
| | |
|---|---|
| *G06T 7/00* | (2017.01) |
| *A61B 6/03* | (2006.01) |
| *G06T 7/11* | (2017.01) |

(52) U.S. Cl.
CPC ............ *G06T 7/0012* (2013.01); *A61B 6/037* (2013.01); *G06T 7/11* (2017.01); *G06T 2207/30024* (2013.01)

(58) Field of Classification Search
None
See application file for complete search history.

(56) References Cited

U.S. PATENT DOCUMENTS

| | | | |
|---|---|---|---|
| 5,762,608 | A | 6/1998 | Warne et al. |
| 6,944,330 | B2 | 9/2005 | Novak et al. |
| 7,450,747 | B2 | 11/2008 | Jabri et al. |
| 7,751,605 | B2 | 7/2010 | Gündel et al. |
| 7,876,938 | B2 | 1/2011 | Huang et al. |

(Continued)

FOREIGN PATENT DOCUMENTS

| | | |
|---|---|---|
| CN | 1200520 A | 12/1998 |
| CN | 1518719 A | 8/2004 |

(Continued)

OTHER PUBLICATIONS

Guan, H. et al., Automatic Hot Spot Detection and Segmentation in Whole Body FDG-PET Images, IEEE International Conference on Image Processing, 4 pages, (2006).

(Continued)

*Primary Examiner* — Miya J Cato
(74) *Attorney, Agent, or Firm* — Choate, Hall & Stewart LLP; Ronen Adato

(57) ABSTRACT

Presented herein are systems and methods that provide automated analysis of 3D images to classify representations of lesions identified therein. In particular, in certain embodiments, approaches described herein allow hotspots representing lesions to be classified based on their spatial relationship with (e.g., whether they are in proximity to, overlap with, or are located within) one or more pelvic lymph node regions in detailed fashion.

22 Claims, 40 Drawing Sheets
(31 of 40 Drawing Sheet(s) Filed in Color)

(56) References Cited

U.S. PATENT DOCUMENTS

| | | | |
|---|---|---|---|
| 7,935,055 B2 | 5/2011 | Burckhardt | |
| 7,970,194 B2 | 6/2011 | Kimura | |
| 8,199,985 B2 | 6/2012 | Jakobsson et al. | |
| 8,211,401 B2 | 7/2012 | Babich et al. | |
| 8,467,856 B2 | 6/2013 | Renisch et al. | |
| 8,538,166 B2 | 9/2013 | Gordon et al. | |
| 8,606,349 B2 | 12/2013 | Rousso et al. | |
| 8,705,887 B2 | 4/2014 | Ma et al. | |
| 8,778,305 B2 | 7/2014 | Pomper et al. | |
| 8,855,387 B2 | 10/2014 | Hamadeh et al. | |
| 8,962,799 B2 | 2/2015 | Babich et al. | |
| 8,995,736 B2 | 3/2015 | Kaufman et al. | |
| 9,002,081 B2 | 4/2015 | Brown | |
| 9,028,800 B2 | 5/2015 | D'Souza et al. | |
| 9,466,133 B2 | 10/2016 | Sowards-Emmerd et al. | |
| 9,710,915 B2 | 7/2017 | Firouzian et al. | |
| 9,721,340 B2 | 8/2017 | Gillies et al. | |
| 10,058,393 B2 | 8/2018 | Bonutti et al. | |
| 10,089,752 B1 | 10/2018 | Bronkalla et al. | |
| 10,112,974 B2 | 10/2018 | Neumaier et al. | |
| 10,140,544 B1 | 11/2018 | Zhao et al. | |
| 10,223,610 B1 | 3/2019 | Akselrod-Ballin et al. | |
| 10,311,971 B2 | 6/2019 | Opfer et al. | |
| 10,330,763 B2 | 6/2019 | James et al. | |
| 10,339,653 B2 | 7/2019 | Gillies et al. | |
| 10,340,044 B2 | 7/2019 | Yao et al. | |
| 10,340,046 B2 | 7/2019 | Baker | |
| RE47,609 E | 9/2019 | Hamadeh et al. | |
| 10,492,723 B2 | 12/2019 | Madabhushi et al. | |
| 10,600,184 B2 | 3/2020 | Golden et al. | |
| 10,665,346 B2 | 5/2020 | Baker | |
| 10,748,652 B2 | 8/2020 | Yao et al. | |
| 10,762,993 B2 | 9/2020 | Baker | |
| 10,815,200 B2 | 10/2020 | Cardinale et al. | |
| 10,818,386 B2 | 10/2020 | Yao et al. | |
| 10,943,681 B2 | 3/2021 | Yao et al. | |
| 10,973,486 B2 | 4/2021 | Sjostrand et al. | |
| 11,011,257 B2 | 5/2021 | Lints et al. | |
| 11,094,066 B2 | 8/2021 | Nie et al. | |
| 11,321,844 B2 | 5/2022 | Johnsson et al. | |
| 11,386,988 B2 | 7/2022 | Johnsson et al. | |
| 11,424,035 B2 | 8/2022 | Baker | |
| 11,508,059 B2 | 11/2022 | Wang et al. | |
| 11,534,125 B2 | 12/2022 | Sjöstrand et al. | |
| 11,564,621 B2 | 1/2023 | Anand et al. | |
| 11,657,508 B2 | 5/2023 | Richter et al. | |
| 11,721,428 B2 | 8/2023 | Brynolfsson et al. | |
| 11,894,141 B2 | 2/2024 | Baker | |
| 11,900,597 B2 | 2/2024 | Anand et al. | |
| 11,937,962 B2 | 3/2024 | Sjöstrand et al. | |
| 11,941,817 B2 | 3/2024 | Richter et al. | |
| 12,224,067 B1 | 2/2025 | Baker | |
| 12,243,236 B1 | 3/2025 | Richter et al. | |
| 12,243,637 B2 | 3/2025 | Brynolfsson et al. | |
| 12,414,748 B2 | 9/2025 | Sjöstrand et al. | |
| 12,417,533 B2 | 9/2025 | Anand et al. | |
| 12,431,246 B2 | 9/2025 | Baker | |
| 2003/0215120 A1 | 11/2003 | Uppaluri et al. | |
| 2005/0065421 A1 | 3/2005 | Burckhardt | |
| 2005/0281381 A1 | 12/2005 | Guendel | |
| 2006/0062425 A1 | 3/2006 | Shen et al. | |
| 2006/0064396 A1 | 3/2006 | Wei et al. | |
| 2006/0078183 A1 | 4/2006 | deCharms | |
| 2007/0081712 A1 | 4/2007 | Huang et al. | |
| 2007/0081713 A1 | 4/2007 | Jerebko | |
| 2007/0100225 A1 | 5/2007 | Maschke | |
| 2007/0115204 A1 | 5/2007 | Budz et al. | |
| 2007/0265230 A1 | 11/2007 | Rousso et al. | |
| 2008/0027315 A1 | 1/2008 | McGinnis | |
| 2008/0214933 A1 | 9/2008 | Von Busch et al. | |
| 2009/0213034 A1 | 8/2009 | Wu et al. | |
| 2009/0309874 A1 | 12/2009 | Salganicoff et al. | |
| 2009/0311182 A1 | 12/2009 | Wang et al. | |
| 2010/0032575 A1 | 2/2010 | Iagaru et al. | |
| 2010/0080434 A1 | 4/2010 | Seifert et al. | |
| 2010/0215581 A1 | 8/2010 | Hoffmann | |
| 2010/0266170 A1 | 10/2010 | Khamene et al. | |
| 2010/0322488 A1 | 12/2010 | Virtue et al. | |
| 2011/0007954 A1 | 1/2011 | Suehling et al. | |
| 2011/0063288 A1 | 3/2011 | Valadez | |
| 2011/0255763 A1 | 10/2011 | Bogoni et al. | |
| 2012/0123253 A1 | 5/2012 | Renisch et al. | |
| 2013/0038707 A1 | 2/2013 | Cunningham et al. | |
| 2013/0094704 A1 | 4/2013 | Hamadeh et al. | |
| 2013/0129168 A1 | 5/2013 | Ross | |
| 2013/0211231 A1 | 8/2013 | Sundarapandian et al. | |
| 2013/0281841 A1 | 10/2013 | Everett et al. | |
| 2014/0105471 A1 | 4/2014 | Brown | |
| 2014/0193336 A1 | 7/2014 | Rousso et al. | |
| 2015/0003703 A1 | 1/2015 | Franz et al. | |
| 2015/0063667 A1 | 3/2015 | Sprencz et al. | |
| 2015/0110716 A1 | 4/2015 | Armor | |
| 2015/0119704 A1 | 4/2015 | Roth et al. | |
| 2015/0221083 A1 | 8/2015 | Berker | |
| 2015/0287188 A1 | 10/2015 | Gazit et al. | |
| 2015/0331995 A1 | 11/2015 | Zhao et al. | |
| 2015/0356730 A1 | 12/2015 | Grove et al. | |
| 2016/0012604 A1 | 1/2016 | Firouzian et al. | |
| 2016/0180042 A1 | 6/2016 | Menon et al. | |
| 2016/0203263 A1 | 7/2016 | Maier et al. | |
| 2016/0275674 A1 | 9/2016 | Rivet-Sabourin et al. | |
| 2016/0335395 A1 | 11/2016 | Wu et al. | |
| 2016/0350947 A1 | 12/2016 | Kelly | |
| 2017/0083682 A1 | 3/2017 | McNutt et al. | |
| 2017/0112577 A1 | 4/2017 | Bonutti et al. | |
| 2018/0140260 A1 | 5/2018 | Taguchi et al. | |
| 2018/0144828 A1 | 5/2018 | Baker | |
| 2018/0259608 A1 | 9/2018 | Golden et al. | |
| 2018/0360402 A1 | 12/2018 | Carmi | |
| 2019/0038239 A1 | 2/2019 | Flohr et al. | |
| 2019/0105009 A1 | 4/2019 | Siemionow et al. | |
| 2019/0105200 A1 | 4/2019 | Hipsley | |
| 2019/0209116 A1 | 7/2019 | Sjostrand et al. | |
| 2019/0333623 A1 | 10/2019 | Hibbard | |
| 2019/0388049 A1 | 12/2019 | Gupta et al. | |
| 2020/0027559 A1 | 1/2020 | Baker | |
| 2020/0051238 A1 | 2/2020 | El Harouni et al. | |
| 2020/0074634 A1 | 3/2020 | Kecskemethy et al. | |
| 2020/0085382 A1 | 3/2020 | Taerum et al. | |
| 2020/0090328 A1 | 3/2020 | Takei et al. | |
| 2020/0097701 A1 | 3/2020 | Chukka et al. | |
| 2020/0126666 A1 | 4/2020 | Baker | |
| 2020/0170604 A1 | 6/2020 | Yildirim et al. | |
| 2020/0193594 A1 | 6/2020 | Georgescu et al. | |
| 2020/0193603 A1 | 6/2020 | Golden et al. | |
| 2020/0245960 A1* | 8/2020 | Richter | G06V 20/698 |
| 2020/0311919 A1* | 10/2020 | Grimmer | G06T 7/0012 |
| 2020/0315455 A1 | 10/2020 | Lee et al. | |
| 2020/0337658 A1 | 10/2020 | Sjostrand et al. | |
| 2020/0342600 A1 | 10/2020 | Sjostrand et al. | |
| 2020/0352518 A1 | 11/2020 | Lyman et al. | |
| 2020/0357117 A1 | 11/2020 | Lyman et al. | |
| 2020/0357118 A1 | 11/2020 | Yao et al. | |
| 2020/0357521 A1 | 11/2020 | Baker | |
| 2020/0410672 A1 | 12/2020 | Katscher et al. | |
| 2021/0032206 A1 | 2/2021 | Neumaier et al. | |
| 2021/0082547 A1 | 3/2021 | Yao et al. | |
| 2021/0093249 A1 | 4/2021 | Anand et al. | |
| 2021/0183485 A1 | 6/2021 | Yao et al. | |
| 2021/0233633 A1 | 7/2021 | Lints et al. | |
| 2021/0334974 A1 | 10/2021 | Johnsson et al. | |
| 2021/0335480 A1 | 10/2021 | Johnsson et al. | |
| 2022/0005586 A1 | 1/2022 | Brynolfsson et al. | |
| 2022/0058804 A1 | 2/2022 | Carmi | |
| 2022/0142480 A1 | 5/2022 | Peck et al. | |
| 2022/0375612 A1 | 11/2022 | Baker | |
| 2022/0398724 A1 | 12/2022 | Anand et al. | |
| 2023/0148980 A1 | 5/2023 | Sjöstrand et al. | |
| 2023/0316530 A1 | 10/2023 | Richter et al. | |
| 2023/0351586 A1 | 11/2023 | Brynolfsson et al. | |
| 2023/0410985 A1 | 12/2023 | Brynolfsson et al. | |
| 2023/0420112 A1 | 12/2023 | Brynolfsson et al. | |
| 2024/0029252 A1 | 1/2024 | Ichinose et al. | |
| 2024/0127437 A1 | 4/2024 | Anand et al. | |

(56) References Cited

U.S. PATENT DOCUMENTS

| | | | |
|---|---|---|---|
| 2024/0169546 A1 | 5/2024 | Richter et al. |
| 2024/0186010 A1 | 6/2024 | Baker |
| 2024/0285246 A1 | 8/2024 | Sjöstrand et al. |
| 2024/0285248 A1 | 8/2024 | Sjöstrand et al. |
| 2024/0354940 A1 | 10/2024 | Sjöstrand et al. |
| 2025/0061580 A1 | 2/2025 | Richter et al. |
| 2025/0062029 A1 | 2/2025 | Baker |
| 2025/0069232 A1 | 2/2025 | Richter et al. |
| 2025/0104225 A1 | 3/2025 | Sjöstrand et al. |
| 2025/0191752 A1 | 6/2025 | Sjöstrand et al. |

FOREIGN PATENT DOCUMENTS

| | | | |
|---|---|---|---|
| CN | 101528267 A | 9/2009 |
| CN | 101639937 A | 2/2010 |
| CN | 102096804 A | 6/2011 |
| CN | 102361594 A | 2/2012 |
| CN | 102438529 A | 5/2012 |
| CN | 102947840 A | 2/2013 |
| CN | 103607954 A | 2/2014 |
| CN | 103930030 A | 7/2014 |
| CN | 104463840 A | 3/2015 |
| CN | 106127819 A | 11/2016 |
| CN | 106558045 A | 4/2017 |
| CN | 107563378 A | 1/2018 |
| CN | 107644421 A | 1/2018 |
| CN | 114219787 A | 3/2022 |
| EP | 1426903 A2 | 6/2004 |
| EP | 1508872 A1 | 2/2005 |
| EP | 2816525 A1 | 12/2014 |
| EP | 3043318 A1 | 7/2016 |
| EP | 3811845 A1 | 4/2021 |
| GB | 2457577 A | 8/2009 |
| JP | 2010-029481 A | 2/2010 |
| JP | 2011-067594 A | 4/2011 |
| JP | 2012-533384 A | 12/2012 |
| JP | 2014-006130 A | 1/2014 |
| JP | 2015-513083 A | 4/2015 |
| JP | 6013042 B2 | 10/2016 |
| JP | 2017-500537 A | 1/2017 |
| JP | 2017067489 A | 4/2017 |
| JP | 6170284 B2 | 7/2017 |
| JP | 2017-198697 A | 11/2017 |
| JP | 2019-537714 A | 12/2019 |
| SE | 524500 C2 | 8/2004 |
| TW | 201201847 A | 1/2012 |
| TW | 201825049 A | 7/2018 |
| TW | 201941750 A | 11/2019 |
| TW | 202006742 A | 2/2020 |
| WO | WO-99/05503 A2 | 2/1999 |
| WO | WO-2007/062135 A2 | 5/2007 |
| WO | WO-2009/084995 A1 | 7/2009 |
| WO | WO-2010/071999 A1 | 7/2010 |
| WO | WO-2011/010231 A1 | 1/2011 |
| WO | WO-2011/077303 A1 | 6/2011 |
| WO | WO-2011/091378 A1 | 7/2011 |
| WO | WO-2011/095580 A1 | 8/2011 |
| WO | WO-2013/059177 A1 | 4/2013 |
| WO | WO-2013/126147 A2 | 8/2013 |
| WO | WO-2015/058151 A2 | 4/2015 |
| WO | WO-2016/087592 A1 | 6/2016 |
| WO | WO-2018/014475 A1 | 1/2018 |
| WO | WO-2018/015953 A1 | 1/2018 |
| WO | WO-2018/081354 A1 | 5/2018 |
| WO | WO-2019/005722 A1 | 1/2019 |
| WO | WO-2019/103912 A2 | 5/2019 |
| WO | WO-2019/136349 A2 | 7/2019 |
| WO | WO-2020/144134 A1 | 7/2020 |
| WO | WO-2020/146032 A1 | 7/2020 |
| WO | WO-2020/190821 A1 | 9/2020 |
| WO | WO-2020/219619 A1 | 10/2020 |
| WO | WO-2020/219620 A1 | 10/2020 |
| WO | WO-2021/061315 A1 | 4/2021 |
| WO | WO-2022/008374 A1 | 1/2022 |
| WO | WO-2022/215530 A1 | 10/2022 |
| WO | WO-2023/057411 A1 | 4/2023 |
| WO | WO-2023/239829 A2 | 12/2023 |
| WO | WO-2024/173297 A1 | 8/2024 |
| WO | WO-2024/211651 A1 | 10/2024 |
| WO | WO-2025/072177 A1 | 4/2025 |

OTHER PUBLICATIONS

Ali, A. et al., The Automated Bone Scan Index as a Predictor of Response to Prostate Radiotherapy in Men with Newly Diagnosed Metastatic Prostate Cancer: An Exploratory Analysis of STAMPEDE's "M1 |Rt Comparison", European Urology Oncology 3:412-419, (2020).

American College of Radiology (ACR) and the Society for Pediatric Radiology (SPR), ACR-SPR Practice Parameter For The Performance Of Skeletal Scintigraphy (Bone Scan), Resolution 28, (2013-Revused2017), available from: <http://www.acr.org>, 9 pages (2017).

Anand, A. et al., A Pre-Analytical Validation Study of Automated Bone Scan Index: Effect on Accuracy and Reproducibility Due to the Procedural Variabilities in Bone Scan Image Acquisition. J Nucl Med. pp. 1865-1871, (2016).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, 1 page, presented Feb. 16, 2017.

Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).

Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).

Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138, 5 pages, (2017).

Armstrong, A. J. et al., Phase 3 Assessment of the Automated Bone Scan Index as a Prognostic Imaging Biomarker of Overall Survival in Men with Metastatic Castration-Resistant Prostate Cancer: A Secondary Analysis of a Randomized Clinical Trial. JAMA Oncology 4:944-951, (2018).

Armstrong, A. J. et al., Phase 3 prognostic analysis of the automated bone scan index (aBSI) in men with bone-metastatic castration-resistant prostate cancer (CRPC), Meeting Library ASC University, 11 pages (2017).

Bai, P. et. al., Body region localization in whole-body low-dose CT images of PET/CT scans using virtual landmarks, Medical Physics Wiley USA, 46(3): 1286-1299 (2019).

Belal, S. et al., Association of PET Index quantifying skeletal uptake in NaF PET/CT images with overall survival in prostate cancer patients, ASCO GU 2017, Poster 178, 1 page, presented Feb. 16, 2017.

Belal, S. et al., PET Index quantifying skeletal uptake in NaF PET/CT images with overall survival in prostate cancer patients, ASCO GU 2017, Abstract, 1 page, (Feb. 13, 2017).

Belal, S. L. et al., 3D skeletal uptake of 18F sodium fluoride in PET/CT images is associate with overall survival in patients with prostate cancer, EJNMMI Research, 7(15):1-8 (2017).

Belal, S.L. et al., Automated evaluation of normal uptake in different skeletal parts in 18F-sodium fluoride (NaF) PET/CT using

(56) References Cited

OTHER PUBLICATIONS a new convolutional neural network method, EJNMMI, EANM '17, 44(Suppl 2):S119-S956, Abstract EP-0116 (2017).

Bombardieri, E. et al., Bone scintigraphy: procedure guidelines for tumour imaging, Eur J. Nucl. Med. Mol. Imaging, 30:BP99-BP106, (2003).

Brynolfsson, J., et al., Deep Learning based urinary bladder segmentation using 18FDCFPyL (PyL-PSMA) PET/CT images, EPS-145, European Association of Nuclear Medicine, (2020), <http://link.springer.com/article/10.1007/s00259-020-04988-4>. pp. S1 and S403-S404, Retrieved Sep. 18, 2020.

Brynolfsson, J., et al., Deep Learning-Enabled comprehensive detection and quantification of 18FDCFPyL (PyL-PSMA) PET/CT, OP-548, European Association of Nuclear Medicine, (2020), <http://link.springer.com/article/10.1007/s00259-020-04988-4>. pp. S1 and S273, Retrieved Sep. 18, 2020.

Bushberg, J. T. et al., Essential Physics of Medical Imaging, Essential Physics of Medical Imaging, 19.3: p. 581 (table 15-3), p. 713 paragraph 6, section 19.3 and p. 720, (2011).

Capobianco, N. et al., Whole-body uptake classification and prostate cancer staging in $^{68}$Ga-PSMA-11 PET/CT using dual-tracer learning, European Journal of Nuclear Medicine and Molecular Imaging, (2021), <https://doi.org/10.1007/s00259-021-05473-2> 10 pages. Retrieved on Apr. 18, 2021.

Ceci, F. et al., E-PSMA: the EANM standardized reporting guidelines v1.0 for PSMA-PET, European Journal of Nuclear Medicine and Molecular Imaging, 48:1626-1638, (2021).

Cha, K. H., et al. Urinary bladder segmentation in CT urography using deep-learning convolutional neural network and level sets, Medical physics, 43(4):1882-1896, (2016).

Christ, P.F. et al., Automatic Liver and Tumor Segmentation of CT and MRI Volumes Using Cascaded Fully Convolutional Neural Networks, Arxiv.org, Cornell University Library, 20 pages, (2017).

Ciernik, I. F., et al. 3D-segmentation of the 18F-choline PET signal for target volume definition in radiation therapy of the prostate, Technology in cancer research & treatment 6(1): 23-30, (2007).

Dennis, E. et al., Bone Scan Index: A Quantitative Treatment Response Biomarker for Castration-Resistant Metastatic Prostate Cancer, Journal of Clinical Oncology, 30(5):519-524 (2012).

Dertat, A., Applied Deep Learning-Part 4: Convolutional Neural Networks, Towards Data Science,<http://towardsdatascience.com/applied-deep-learning-part-4-convolutional-neural-networks-584bc134c1e2> 26 pages, (2017).

Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).

Fendler, W.P. et al., $^{68}$Ga-PSMA PET/CT: Joint EANM and SNMMI procedure guideline for prostate cancer imaging: version 1.0, Eur J Nucl Med Mol Imaging, DOI 10.1007/s00259-017-3670-z, 11 pages, (2017).

GE Healthcare, SPECT/CT Cameras, 2 pages, retrieved Oct. 25, 2017: <http://www3.gehealthcare.com.sg/en-gb/products/categories/nuclear_medicine/spect-ct_cameras>.

Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).

Gjertsson, K., et al., A Novel Automated Deep Learning Algorithm for Segmentation of the Skeleton in Low-Dose CT for [(18)F] DCFPyL PET/CT Hybrid Imaging in Patients with Metastatic Prostate Cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0823, p. S765.

Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>.

Goffin, K. E. et al., Phase 2 study of 99mTc-trofolastat SPECT/CT to identify and localize prostate cancer in intermediate- and high-risk patients undergoing radical prostatectomy and extended pelvic lymph node dissection, J. Nucl. Med., 27 pages (2017).

Guimond, A. et al., Average Brain Models: A Convergence Study, Computer Vision and Image Understanding, 77:192-210 (2000).

Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).

Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.

Horikoshi, H. et al., Computer-aided diagnosis system for bone scintigrams from Japanese patients: importance of training database, Annals of Nuclear Medicine, 26(8):622-626 (2012).

Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).

Im, HJ, et al., et al., Current Methods to Define Metabolic Tumor Volume in Positron Emission Tomography: Which One is Better?, Nucl. Med. Mol. Imaging, 52(1):5-15, (2018).

Johnsson, K. et al., Analytical performance of aPROMISE: automated anatomic contextualization, detection, and quantification of [18F]DCFPyL (PSMA) imaging for standardized reporting, European Journal of Nuclear Medicin and Molecular Imaging, 11 pages, Aug. 31, 2021, doi: 10.1007/s00259-021-05497-8. Epub ahead of print. PMID: 34463809.

Johnsson, K., et. al., miPSMA Index: Comprehensive and Automated Quantification of 18F-DCFPyL (PyL-PSMA) PET/CT for Prostate Cancer Staging, J Nucl Med., 61: (Supplement 1): 1435, 5 pages, (2020).

Kaboteh R. et al., Progression of bone metastases in patients with prostate cancer—automated detection of new lesions and calculation of bone scan index, EJNMMI Research, 3:64, 6 pages, (2013).

Kaboteh, R. et al., Convolutional neural network based quantification of choline uptake in PET/CT studies is associated with overall survival in patents with prostate cancer, EJNMMI, EANM '17, 44(Suppl 2):S119-S956, Abstract EP-0642 (2017).

Kiess, et al., Prostate-specific membrane antigen and a target for cancer imaging and therapy, The Quarterly Journal of Nuclear Medicine and Molecular Imaging, 59(3):241-268 (2015).

Kikuchi, A. et al., Automated segmentation of the skeleton in whole-body bone scans: influence of difference in atlas, Nuclear Medicine Communications, 33(9):947-953 (2012).

Kinahan, P.E. et al., PET/CT Standardized Update Values (SUVs) in Clinical Practice and Assessing Response to Therapy, Semin Ultrasound CT MR 31(6):496-505 (2010) retrieved Oct. 25, 2017: <https://www.ncbi.nlm.nih.gov/pmc/articles/PMC3026294/>.

Knutsson, H., and Andersson, M., Morphons: Segmentation using Elastic Canvas and Paint on Priors, IEEE International Conference on Image Processing (ICIP 2005), Genova, Italy, 4 pages (2005).

Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).

Lin, T.Y. et. al., Feature Pyramid Networks for object detection, FAIR, 10 pages, (2016), <https://arxiv.org/abs/1612.03144v1>.

Litjens, G. et al., A survey on deep learning in medical image analysis, Medical Image Analysis, 42:60-88, (2017).

Liu, L. et al., Computer-Aided Detection of Prostate Cancer with MRI: Technology and Applications, Acad Radiol. Author manuscript, 50 pages 2016.

Ma, L. et al., Automatic segmentation of the prostate on CT images using deep learning and multi-atlas fusion, Proc. of SPIE vol. 10133:1013320-1-1013320-9 (2017).

Ma, L. et al., Combining Population and Patient-Specific Characteristics for Prostate Segmentation on 3D CT Images, Proc of SPIE 9784:978427-1-8 (2016).

(56)     References Cited

OTHER PUBLICATIONS

Ma, L. et al., Random Walk Based Segmentation for the Prostate on 3D Transrectal Ultrasound Images, Proc SPIE Int Soc Opt Eng. Author manuscript, 13 pages (2016).

Matsubara, N. et al., A Phase II, Randomized, Open-Label, Multi-arm Study of TAS-115 for Castration-Resistant Prostate Cancer Patients With Bone Metastases, Clinical Genitourinary Cancer, 000(xxx):1-10, (2021).

Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.

Meyer, A., et. al., Deep learning algorithm improves identification of men with low-risk prostate cancer using PSMA targeted 99mTc-MIP-1404 SPECT/CT, Journal of Clinical Oncology, 37:(15), (2019).

Nakajima, K. et al., Enhanced diagnostic accuracy for quantitative bone scan using an artificial neural network system: a Japanese multi-center database project, EJNMMI Research, 3:83, 9 pages, (2013).

National Cancer Institute, NCI Drug Dictionary: gallium Ga 68-labeled PSMA-11, 1 page, retrieved Oct. 25, 2017: <https://www.cancer.gov/publications/dictionaries/cancer-drug?cdrid=766400>.

National Cancer Institute, NCI Drug Dictionary: technetium Tc 99m methylene diphosphonate, 1 page, retrieved Oct. 25, 2017: <https://www.cancer.gov/publications/dictionaries/cancer-drug?cdrid=537722>.

Nickols, N. et al., aPROMISE: A Novel Automated-PROMISE platform to Standardize Evaluation of Tumor Burden in 18F-DCFPyL (PSMA) images of Veterans with Prostate Cancer, Journal of Nuclear Medicine, 26 pages, May 28, 2021, doi: 10.2967/jnumed.120.261863.

Nickols, N.G., et al., A deep learning algorithm to predict coexisting metastatic disease using intraprostatic [F18]DCFPYL PSMA image alone in veterans with prostate cancer, Journal of Clinical Oncology 38, (Supplement 6), 2020.

Ohlsson, M., et. al., Automated decision support for bone scintigraphy, Computer-based medical systems, pp. 1-6, (2009).

Paschalis, A. et al., Prostate-specific Membrane Antigen Heterogeneity and DNA Repair Defects in Prostate Cancer, European Urology, 76(4):469-478, (2019).

Perera, M. et al., Sensitivity, Specificity, and Predictors of Positive 68Ga-Prostate-specific Membrane Antigen Positron Emission Tomography in Advanced Prostate Cancer: A Systematic Review and Meta-analysis, European Urology, 70(6):926-937 (2016).

Polymeri, E. et al., Analytical validation of an automated method for segmentation of the prostate gland in CT images, EJNMMI, EANM '17, 44(Suppl 2):S119-S956, Abstract EP-0641 (2017).

Polymeri, E., et al., Deep learning-based quantification of PET/CT prostate gland uptake: association with overall survival, Clinical Physiology Functional Imaging, DOI: 10.1111/cpf.12611, 40(2):106-113, (2019).

Pouliot, F., et al., Prospective evaluation of a Novel Deep Learning Algorithm (PSMA-AI) in the assessment of 99mTc-MIP-1404 SPECT/CT in patients with low or intermediate risk prostate cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0804, p. S765.

Radiologyinfo.org for Patients, Computed Tomography (CT), 2 pages, retrieved Oct. 25, 2017: <https://www.radiologyinfo.org/en/submenu.cfm?pg=ctscan>.

Ren, S., et al., Faster R-CNN: Towards Real-Time Object Detection with Region Proposal Networks, 14 pages, (2015), <http://image-net.org/challenges/LSVRC/2015/results>.

Ronneberger, O., et al., U-Net: Convolutional Networks for Biomedical Image Segmentation, Springer International Publishing, pp. 234-241, (2015), <http://lmb.informatik.uni-freiburg.de/>. Published online on Nov. 18, 2015.

Rowe, S. P. et al., PET Imaging of prostate-specific membrane antigen in prostate cancer: current state of the art and future challenges, Prostate Cancer and Prostatic Diseases, pp. 1-8 (2016).

Rowe, S. P. et al., PSMA-Based [18F]DCFPyL PET/CT Is Superior to Conventional Imaging for Lesion Detection in Patients with Metastatic Prostate Cancer, Mol Imaging Biol, 18:411-419, (2016).

Sabbatini, P. et al., Prognostic Significance of Extent of Disease in Bone in Patients With Androgen-Independent Prostate Cancer, Journal of Clinical Oncology, 17(3):948-957 (1999).

Sadik, M. et al., 3D prostate gland uptake of 18F-choline—association with overall survival in patients with hormone-naïve prostate cancer, The Journal of Nuclear Medicine, 58(Suppl. 1):Abstract 544, 2 pages, (2017).

Sadik, M. et al., A new computer-based decision-support system for the interpretation of bone scans, Nuclear Medicine Communications, 27(5):417-423 (2006).

Sadik, M. et al., Automated 3D segmentation of the prostate gland in CT images—a first step towards objective measurements of prostate uptake in PET and SPECT images, Journal of Nuclear Medicine, 58(1):1074, (2017).

Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).

Sadik, M. et al., Computer-assisted interpretation of planar whole-body bone scans, Journal Nuclear Medicine, 49(12):1958-65, 2008.

Sadik, M. et al., Convolutional neural networks for segmentation of 49 selected bones in CT images show high reproducibility, EJNMMI, EANM '17, 44(Suppl 2):S119-S956, Abstract OP-657 (2017).

Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.

Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).

Sajn, L. et al., Computerized segmentation of whole-body bone scintigrams and its use in automated diagnostics, Computer Methods and Programs in Biomedicine, 80:47-55 (2005).

Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).

Santos-Cuevas, C. et al. 99mTc-labeled PSMA inhibitor: Biokinetics and radiation dosimetry in healthy subjects and imaging of prostate cancer tumors in patients, Nuclear Medicine and Biology 52:1-6, (2017).

Shi, F. et al., Deep learning empowered volume delineation of whole-body organs-at-risk for accelerated radiotherapy, Nat. Commun., 13(1):6566 (2022).

Sjöstrand K. et al., Statistical regularization of deformation fields for atlas-based segmentation of bone scintigraphy images, MICCAI 5761:664-671 (2009).

Sjöstrand, K., et al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).

Sjostrand, K., et al., Automated Assessment of Prostatic PSMA Expression in SPECT/CT using Deep Convolutional Neural Networks—A Prospectively Planned Retrospective Analysis of Phase 3 Study MIP-1404-3301, The Journal of Nuclear Medicine, 60 (Supplement 1): Abstract 401, 1 page, (2019).

Sluimer, I. et al., Toward Automated Segmentation of the Pathological Lung in CT, IEEE Transactions on Medical Imaging, 24(8):1025-1038 (2005).

Tian, Z. et al., A fully automatic multi-atlas based segmentation method for prostate MR images, Proc SPIE Int Soc Opt Eng. Author manuscript, 12 pages (2015).

Tian, Z. et al., A supervoxel-based segmentation method for prostate MR images, Med. Phys., 44(2):558-569 (2017).

Tian, Z. et al., Deep convolutional neural network for prostate MR segmentation, Proc. of SPIE 10135:101351L-1-101351L-6 12 pages, (2017).

(56) References Cited

OTHER PUBLICATIONS

Tian, Z., et al., Superpixel-based Segmentation for 3D Prostate MR Images, IEEE Trans Med Imaging, Author manuscript, pp. 558-569, (2016).
Trägårdh, E., et al., RECOMIA—a cloud-based platform for artificial intelligence research in nuclear medicine and radiology, EJNMMI Physics, <https://doi.org/10.1186/s40658-020-00316-9>, 7:51, 12 pages, (2020).
Ulmert, D. et al., A Novel Automated Platform for Quantifying the Extent of Skeletal Tumour Involvement in Prostate Cancer Patients Using the Bone Scan Index, European Urology, 62(1):78-84 (2012).
Wallis, J.W. et. al., Three-dimensional display in nuclear medicine, IEEE Trans Med Imaging, 8(4):297-303, (1989).
Wrangsjo, A. et al., Non-rigid Registration Using Morphons, Proceedings of the 14th Scandinavian Conference on Image Analysis (SCIA '05), pp. 501-510 (2005).
Yin, T.-K., and Chiu, N.T., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).
Afshar-Oromieh, A. et al., Radiation dosimetry of (68)Ga-PSMA-11 (HBED-CC) and preliminary evaluation of optimal imaging timing, Eur. J. Nucl. Med. Mol. Imaging, 43(9):1611-1620 (2016).
Gandaglia, G. et al., Distribution of metastatic sites in patients with prostate cancer: A population-based analysis, Prostate, 74(2):210-216 (2014).
Giesel, F.L. et al., (18)F-Labelled PSMA-1007 shows similarity in structure, biodistribution and tumour uptake to the theragnostic compound PSMA-617, Eur. J. Nucl. Med. Mol. Imaging, 43(10):1929-1930 (2016).
Greenspan, H. et al., Deep Learning in Medical Imaging: Overview and Future Promise of an Exciting New Technique, IEEE Transactions on Medical Imaging, 35(5):1153-1159 (2016).
Guntur, A.R. and Rosen, C.J., Bone as an endocrine organ, Endocr. Pract., 18(5):758-762 (2012).
Kaur, D. and Kaur, Y., Various Image Segmentation Techniques: A Review, International Journal of Computer Science and Mobile Computing, 3(5):809-814 (2014).
Pizzuto, D.A. et al., The central zone has increased 68Ga-PSMA-11 uptake: "Mickey Mouse ears" can be hot on 68Ga-PSMA-11 PET, Eur. J. Nucl. Med. Mol. Imaging, 45(8):1335-1343 (2018).
Seifert, S. et al., Hierarchical parsing and semantic navigation of full body CT data, Medical Imaging 2009: Image Processing, Proceedings of SPIE vol. 7259, 8 pages, (2009).
Sharma, N. and Aggarwal, L.M., Automated medical image segmentation techniques, J. Med. Phys., 35(1):3-14 (2010).
Shen, D. et al., Deep Learning in Medical Image Analysis, Annu. Rev. Biomed. Eng., 19:221-248 (2017).
Weineisen, M. et al., 68Ga- and 177Lu-Labeled Psma I&T: Optimization of a PSMA-Targeted Theranostic Concept and First Proof-of-Concept Human Studies, J. Nucl. Med., 56(8):1169-1176 (2015).
Partin, A.W. et al., Combination of prostate-specific antigen, clinical stage, and Gleason score to predict pathological stage of localized prostate cancer. A multi-institutional update, JAMA, 277(18):1445-1451 (1997).
Partin, A.W. et al., The use of prostate specific antigen, clinical stage and Gleason score to predict pathological stage in men with localized prostate cancer, J. Urol., 150(1):110-114 (1993).
Poulakis, V. et al., Preoperative neural network using combined magnetic resonance imaging variables, prostate specific antigen, and Gleason score to predict prostate cancer recurrence after radical prostatectomy, Eur. Urol., 46(5):571-578 (2004).
Ghosh, P. and Mitchell, M., Prostate segmentation on pelvic CT images using a genetic algorithm, Proceedings of SPIE, vol. 6914, Medical Imaging 2008: Image Processing, 8 pages, (2008).
He, K. et al., Pelvic Organ Segmentation Using Distinctive Curve Guided Fully Convolutional Networks, IEEE Trans. Med. Imaging, 38(2):585-595 (2019).
Iandola, F.N. et al., SqueezeNet: AlexNet-level accuracy with 50x fewer parameters and <0.5MB model size, arXiv, 13 pages, (2016).

Chen, X. et al., TensorMask: A Foundation for Dense Object Segmentation, Proceedings of the IEEE/CVF International Conference on Computer Vision (ICCV), 10 pages, (2019).
De Brabandere, B. et al., Semantic Instance Segmentation with a Discriminative Loss Function, arXiv preprint, 10 pages, (2017).
Hatamizadeh, A. et al., UNETR: Transformers for 3D Medical Image Segmentation, Proceedings of the IEEE/CVF Winter Conference on Applications of Computer Vision (WACV), 11 pages, (2022).
Milletari, F. et al., V-Net: Fully Convolutional Neural Networks for Volumetric Medical Image Segmentation, 2016 Fourth International Conference on 3D Vision (3DV), 11 pages, (2016).
Blue Earth Diagnostics, Posluma Highlights of Prescribing Information, 12 pages, (2023).
Emmett, L. et al., The PRIMARY Score: Using Intraprostatic 68Ga-PSMA PET/CT Patterns to Optimize Prostate Cancer Diagnosis, J. Nucl. Med., 63(11):1644-1650 (2022).
Benitez, C.M. et al., Treatment Response Assessment According to Updated PROMISE Criteria in Patients with Metastatic Prostate Cancer Using an Automated Imaging Platform for Identification, Measurement, and Temporal Tracking of Disease, European Urology Oncology, 9 pages, (2024).
Wan, H., Automated Contouring Using Neural Networks, Contour Protege AI White Paper, 3 pages, (2020), <https://go.mimsoftware.com/contour-protegeai-plus/white-paper>.
Nitta, S. et al., Assisted Diagnosis System by Automatic Extraction of Tumor Candidate Areas from PET/CT Images, Medical Imaging Technology, 24(3):181-190 (2006). English translation included.
Gafita, A. et al., Novel Framework for Treatment Response Evaluation Using PSMA PET/CT in Patients with Metastatic Castration-Resistant Prostate Cancer (RECIP 1.0): An International Multicenter Study, J. Nucl. Med., 63(11):1651-1658 (2022).
Inoue, T., What cancers can be understood and not known by "PET"?—Effects of PET scanning by site, Medical Note Interview, 4 pages, (2015), retrieved from the internet at: https://medicalnote.jp/contents/150715-000003-CYJIZE.
Kawakami, K. et al., Introduction of bone scintigraphy diagnosis support software "BONENAVI" (Topics), Journal of Nuclear Medicine (Japanese), 63:41-51 (2011).
Kawakami, K., Evaluation of bone metastasis by bone scintigraphy diagnostic support software BONENAVI, Communication of the Imaging Group of the JSRT, 36(1):74-77 (2013).
Nogi, S. et al., Metastatic bone tumor quantified by computer-assisted diagnosis system of bone scintigraphy, Nuclear Medicine in Clinic, 45(3):35-37 (2012).
Seifert, R. et al., Second Version of the Prostate Cancer Molecular Imaging Standardized Evaluation Framework Including Response Evaluation for Clinical Trials (PROMISE V2), Eur. Urol., 83(5):405-412 (2023).
US Food and Drug Administration, Clinical Trial Endpoints for the Approval of Cancer Drugs and Biologics, 21 pages, (2018).
Washino, H., Injectable for bone scintigraphy: Technetium hydroxymethylenediphosphonate (99mTc) injection solution (Revised Edition), 9 pages, (2007), retrieved from the internet at:https://rada.or.jp/database/home4/normal/ht-docs/member/synopsis/030292.html#:%7E:text=%E6%A6%82%E8%A6%81).
Gorthi, S. et al., Segmentation of Head and Neck Lymph Node Regions for Radiotherapy Planning Using Active Contour-Based Atlas Registration, IEEE Journal of Selected Topics in Signal Processing, 3(1):135-147 (2009).
Grahovac, M. et al., Machine learning predictive performance evaluation of conventional and fuzzy radiomics in clinical cancer imaging cohorts, Eur. J. Med. Mol. Imaging, 50(6):1607-1620 (2023).
International Search Report for PCT/EP2022/077505, filed Oct. 4, 2022, 9 pages, (mailed Mar. 23, 2023).
Invitation to Pay Additional Fees for PCT/EP2022/077505, filed Oct. 4, 2022, 15 pages, (mailed Feb. 2, 2023).
Kertesz, H. et al., Implementation of a Spatially-Variant and Tissue-Dependent Positron Range Correction for PET/CT Imaging, Front. Physiol., 13:818463 (2022).

(56)          References Cited

OTHER PUBLICATIONS

Kertesz, H. et al., Positron range in combination with point-spread-function correction: an evaluation of different implementations for [124I]-PET imaging, ENJMMI Phys., 9(1):56 (2022).

Khurshid, Z. et al., Role of textural heterogeneity parameters in patient selection for 177Lu-PSMA therapy via response prediction, Oncotarget., 9(70):33312-33321 (2018).

Krajnc, D. et al., Automated data preparation for in vivo tumor characterization with machine learning, Front. Oncol., 12:1017911 (2022).

Papp, L. et al., Glioma Survival Prediction with Combined Analysis of In Vivo 11C-MET PET Features, Ex Vivo Features, and Patient Features by Supervised Machine Learning, J. Nucl. Med., 59(6):892-899 (2018).

Papp, L. et al., Optimized Feature Extraction for Radiomics Analysis of 18F-FDG PET Imaging, J. Nucl. Med., 60(6):864-872 (2019).

Papp, L. et al., Supervised machine learning enables non-invasive lesion characterization in primary prostate cancer with [68Ga]Ga-PSMA-11 PET/MRI, Eur. J. Nucl. Mol. Imaging, 48(6):1795-1805 (2021).

Teng, C. et al., Head and neck lymph node region delineation using a hybrid image registration method, 3rd IEEE International Symposium on Biomedical Imaging: Nano to Macro, 4 pages, (2006).

Valladares, A. et al., A multi-modality physical phantom for mimicking tumor heterogeneity patterns in PET/CT and PET/MRI, Med. Phys., 49(9):5819-5829 (2022).

Written Opinion for PCT/EP2022/077505, filed Oct. 4, 2022, 11 pages, (mailed Mar. 23, 2023).

Kumar, A. et al., Designing user interfaces to enhance human interpretation of medical content-based image retrieval: application to PET-CT images, Int. J. Comput. Assist. Radiol. Surg., 8(6):1003-1014 (2013).

Mata, C. et al., ProstateAnalyzer: GUI in Medical Domain with Management of DICOM Images of Prostate Cancer (PCa), 1 page, (2012).

Roman-Jimenez, G. et al., Detection of bladder metabolic artifacts in (18)F-FDG PET imaging, Comput. Biol. Med., 71:77-85 (2016).

Saha, M. et al., An Advanced Deep Learning Approach for Ki-67 Stained Hotspot Detection and Proliferation Rate Scoring for Prognostic Evaluation of Breast Cancer, Sci. Rep., 7(1):3213 (2017).

* cited by examiner

106

104

102

Translation

Rigid registration

2702

2704

2800

2804

2808

Anatomical segmentation

2810

2812

Determine whole body landmarks

2814

Whole-body landmarks

2816

Classify hotspots according to distant metastases type

2820

Classified hotspots

2806

SYSTEMS AND METHODS FOR AUTOMATED IDENTIFICATION AND CLASSIFICATION OF LESIONS IN LOCAL LYMPH AND DISTANT METASTASES

CROSS-REFERENCE TO RELATED APPLICATIONS

This application claims priority to and benefit of U.S. Provisional Patent Application No. 63/336,998, filed Apr. 29, 2022 and U.S. Provisional Patent Application No. 63/253,709, filed Oct. 8, 2021, the contents of each of which is incorporated herein by reference in its entirety.

TECHNICAL FIELD

This invention relates generally to systems and methods for creation, analysis, and/or presentation of medical image data. More particularly, in certain embodiments, the invention relates to systems and methods for automated analysis of medical images to identify and/or characterize cancerous lesions.

BACKGROUND

Nuclear medicine imaging involves the use of radiolabeled compounds, referred to as radiopharmaceuticals. Radiopharmaceuticals are administered to patients and accumulate in various regions in the body in manner that depends on, and is therefore indicative of, biophysical and/or biochemical properties of tissue therein, such as those influenced by presence and/or state of disease, such as cancer. For example, certain radiopharmaceuticals, following administration to a patient, accumulate in regions of abnormal osteogenesis associated with malignant bone lesions, which are indicative of metastases. Other radiopharmaceuticals may bind to specific receptors, enzymes, and proteins in the body that are altered during evolution of disease. After administration to a patient, these molecules circulate in the blood until they find their intended target. The bound radiopharmaceutical remains at the site of disease, while the rest of the agent clears from the body.

Nuclear medicine imaging techniques capture images by detecting radiation emitted from the radioactive portion of the radiopharmaceutical. The accumulated radiopharmaceutical serves as a beacon so that an image may be obtained depicting the disease location and concentration using commonly available nuclear medicine modalities. Examples of nuclear medicine imaging modalities include bone scan imaging (also referred to as scintigraphy), single-photon emission computerized tomography (SPECT), and positron emission tomography (PET). Bone scan, SPECT, and PET imaging systems are found in most hospitals throughout the world. Choice of a particular imaging modality depends on and/or dictates the particular radiopharmaceutical used. For example, technetium 99m ($^{99m}$Tc) labeled compounds are compatible with bone scan imaging and SPECT imaging, while PET imaging often uses fluorinated compounds labeled with 18F. The compound $^{99m}$Tc methylenediphosphonate ($^{99m}$Tc MDP) is a popular radiopharmaceutical used for bone scan imaging in order to detect metastatic cancer. Radiolabeled prostate-specific membrane antigen (PSMA) targeting compounds such as $^{99m}$Tc labeled 1404 and PyL™ (also referred to as [18F]DCFPyL) can be used with SPECT and PET imaging, respectively, and offer the potential for highly specific prostate cancer detection.

Accordingly, nuclear medicine imaging is a valuable technique for providing physicians with information that can be used to determine the presence and the extent of disease in a patient. The physician can use this information to provide a recommended course of treatment to the patient and to track the progression of disease.

For example, an oncologist may use nuclear medicine images from a study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the nuclear medicine images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results. If an imaging study shows that the patient has a particular disease or condition (e.g., cancer), the physician discusses various treatment options, including surgery, as well as risks of doing nothing or adopting a watchful waiting or active surveillance approach, rather than having surgery.

Accordingly, the process of reviewing and analyzing multiple patient images, over time, plays a critical role in the diagnosis and treatment of cancer. There is a significant need for improved tools that facilitate and improve accuracy of image review and analysis for cancer diagnosis and treatment. Improving the toolkit utilized by physicians, radiologists, and other healthcare professionals in this manner provides for significant improvements in standard of care and patient experience.

SUMMARY

Presented herein are systems and methods that provide for automated analysis of 3D images to classify representations of lesions identified therein. In particular, in certain embodiments, approaches described herein allow hotspots representing lesions to be classified based on their spatial relationship with (e.g., whether they are in proximity to, overlap with, or are located within) one or more pelvic lymph node regions in detailed fashion.

In particular, in certain embodiments, approaches described herein address difficulties in identifying and/or directly segmenting pelvic lymph regions, such as an iliac or portion thereof, within anatomical images such as low dose CT images. In certain embodiments, systems and methods described herein utilize an approach that combines direct (e.g., machine learning-based) segmentation of a 3D anatomical image with an atlas image approach. For example, a CT image may be segmented to create a segmentation map [e.g., comprising one or more labeled regions (e.g., segmentation masks), each identifying a particular anatomical or tissue region] that identifies various regions, including pelvic bones (e.g., which can be accurately segmented within a CT image) within the CT image. The pelvic bone regions of the segmentation map are used, together with corresponding reference pelvic bone regions of a pelvic atlas image, as landmarks to determine a transformation (e.g., coordinate transformation) that co-registers the pelvic atlas image with the segmentation map.

The pelvic atlas image may also include identifications of pelvic lymph regions (e.g., an internal iliac, an external iliac, a common iliac, an obturator, and a presacral region). In certain embodiments, by transforming the pelvic atlas image to register it with the segmentation map, the pelvic lymph regions of the transformed pelvic atlas image are thereby aligned to the 3D anatomical image. Where the 3D anatomical image is (e.g., also) aligned with a 3D functional image, such as a PET image (e.g., as in a PET/CT composite image), hotspots within the 3D functional image can be identified as being located within, overlapping with, and/or in close proximity to particular pelvic lymph regions. In this manner, hotspots can be classified based on their spatial relationship with particular lymph sub-regions, allowing for detailed local-lymph-based classification.

In one aspect, the invention is directed to a method for automatically processing 3D images of a subject to identify and/or characterize cancerous lesions within the subject, the method comprising: (a) receiving, by a processor of a computing device, (i) a 3D functional image of the subject obtained using a functional imaging modality and (ii) a 3D anatomical image of the subject obtained using an anatomical imaging modality, wherein the 3D functional image and the 3D anatomical image are aligned [e.g., the 3D functional image and the 3D anatomical image having been acquired using a (e.g., single) multimodal imaging system (e.g., a PET/CT imaging system; e.g., a SPECT/CT imaging system); e.g., the 3D functional image and the 3D anatomical image having been acquired separately and subsequently co-registered] and include a representation of a pelvic region of the subject, and wherein the 3D functional image includes one or more hotspots representing potential lesions within the pelvic region of the subject; (b) segmenting, by the processor, the 3D anatomical image of the subject to identify representations of one or more pelvic bones within the 3D anatomical image of the subject, thereby creating a 3D segmentation map aligned with the 3D anatomical image of the subject and comprising one or more (e.g., labeled) pelvic bone regions, wherein each pelvic bone region corresponds to a particular pelvic bone and/or group of one or more pelvic bones and identifies a representation of the particular pelvic bone and/or group of one or more pelvic bones within the 3D anatomical image; (c) receiving, by the processor, a 3D pelvic atlas image comprising: (A) an identification (e.g., one or more segmentation masks; e.g., one or more 3D segmentation masks, e.g., a segmentation map) of one or more pelvic lymph sub-regions in the 3D pelvic atlas image [e.g., wherein each pelvic lymph sub-region is a segmented region that identifies a particular anatomical structure (e.g., an internal iliac (e.g., a left and/or right internal iliac), an external iliac (e.g., a left and/or right external iliac), a common iliac (e.g., a left and/or right common iliac), an obturator, a presacral) and/or that identifies a sub-volume corresponding to a local region surrounding a particular anatomical structure (e.g., a left/right internal iliac, a left/right external iliac, a left/right common iliac, an obturator, a presacral)] (e.g., each pelvic lymph sub-region identified by a particular segmentation mask); and (B) an identification (e.g., one or more segmentation masks; e.g., one or more 3D segmentation masks, e.g., a segmentation map) of one or more reference pelvic bone regions in the 3D pelvic atlas image, wherein at least a portion of the one or more reference pelvic bone regions in the 3D pelvic atlas image corresponds to (e.g., depicts a same particular pelvic bone or group of one or more pelvic bones) one or more of the pelvic bone regions of the 3D segmentation map; (d) transforming (e.g., applying a coordinate transform to), by the processor, the 3D pelvic atlas image to co-register it with the 3D segmentation map using (i) the one or more reference pelvic bone regions identified within the pelvic atlas image and (ii) the one or more pelvic bone regions of the 3D segmentation map (e.g., as landmarks), thereby creating a transformed 3D pelvic atlas image comprising the identified one or more pelvic lymph sub-regions thereby aligned to the 3D anatomical image and segmentation thereof (e.g., the 3D segmentation map); and (e) determining, by the processor, for each of the one or more hotspots of the 3D functional image, a pelvic lymph classification using the identification of the one or more pelvic lymph sub-regions within the transformed 3D pelvic atlas image [e.g., by identifying each particular hotspot of the one or more hotspots as lying within and/or overlapping with and/or in proximity to a particular pelvic lymph sub-region (e.g., based on a determination that the particular hotspot is located within and/or is located closest to a particular pelvic lymph sub-region)].

In certain embodiments, the 3D functional image is a positron emission tomography (PET) image obtained following administration, to the subject, of a radiopharmaceutical [e.g., a radiopharmaceutical comprising a PSMA binding agent (e.g., [18F]DCFPyL, [18F]DCFBC, $^{68}$Ga-PSMA-11 (also known as $^{68}$Ga-PSMA-HBED-CC), $^{68}$Ga-PSMA-617, PSMA I&T, 18F-PSMA-1007, 18F-JK-PSMA-7)] (e.g., and wherein the 3D anatomical image is a CT image).

In certain embodiments, the radiopharmaceutical comprises a Prostate Specific Membrane Antigen (PSMA) binding agent.

In certain embodiments, the 3D anatomical image is a CT image.

In certain embodiments, the 3D pelvic atlas image received at step (c) is selected from a set of multiple prospective 3D pelvic atlas images (e.g., multiple different 3D pelvic atlas image options, e.g., reflecting different subject body types, height/weights ranges, etc.).

In certain embodiments, the 3D pelvic atlas image comprises (e.g., as the identification of the one or more pelvic lymph sub-regions) one or more reference markers [e.g., 2D surfaces (e.g., planar surfaces, e.g., curved surfaces)], each of which demarks a boundary between two or more of the pelvic lymph sub-regions, thereby identifying the one or more pelvic lymph sub-regions within the 3D pelvic atlas image.

In certain embodiments, the 3D pelvic atlas image comprises (e.g., as the identification of the one or more pelvic lymph sub-regions) one or more representations of extended sub-volumes, each extended sub-volume corresponding to a particular one of the one or more pelvic lymph sub-regions and representing a local volume about a particular pelvic lymph node, thereby identifying the one or more pelvic lymph sub-regions within the 3D pelvic atlas image.

In certain embodiments, the 3D pelvic atlas image comprises (e.g., as the identification of the one or more pelvic lymph sub-regions) a 3D pelvic lymph segmentation map that identifies one or more pelvic lymph nodes.

In certain embodiments, step (d) comprises: determining a first transformation that aligns (i) a first subset of the one or more reference pelvic bone regions identified within the pelvic atlas image to (ii) a corresponding first subset of the one or more pelvic bone regions of the 3D segmentation map (e.g., as landmarks) (e.g., representing pelvic bones and/or group(s) of pelvic bones on a left side of the subject); determining a second transformation that aligns (i) a second subset of the one or more reference pelvic bone regions identified within the pelvic atlas image to (ii) a corresponding second subset of the one or more pelvic bone regions of the 3D segmentation map (e.g., as landmarks) (e.g., representing pelvic bones and/or group(s) of pelvic bones on a right side of the subject); and determining a final overall transformation based on the first transformation and the second transformation (e.g., as a weighted function of the first transformation and the second transformation), and using the final overall transformation to transform the 3D pelvic atlas image.

In certain embodiments, the method comprises: performing steps (c) and (d) for a plurality of prospective 3D pelvic atlas images to determine, for each of the prospective 3D pelvic atlas images, a corresponding transformed version and selecting, by the processor, a particular one of the prospective 3D pelvic atlas images as a best-fit 3D pelvic atlas image [e.g., based on one or more performance metrics computed for each of the prospective 3D pelvic atlas images (e.g., based on the transformed version of each of the prospective 3D pelvic atlas images)]; and using the transformed version of the best-fit 3D pelvic atlas image as the transformed 3D pelvic atlas image to determine, at step (e), the pelvic lymph classification for each of the one or more hotspots.

In certain embodiments, step (d) comprises: performing coarse registration to co-register the 3D pelvic atlas image with the 3D segmentation map using (i) the one or more reference pelvic bone regions identified within the pelvic atlas image and (ii) the one or more pelvic bone regions of the 3D segmentation map; and refining the 3D pelvic atlas image to create the transformed 3D pelvic atlas image {e.g., wherein performing the coarse registration comprises determining a registration transformation that that aligns (i) a reference pelvic bone region comprising the one or more reference pelvic bone regions identified within the 3D pelvic atlas image [e.g., a reference pelvic bone mask and/or distance map created therefrom that represent a combined pelvic bone region comprising the one or more reference pelvic bones (together)] to (ii) a target pelvic bone region comprising the one or more pelvic bone regions of the 3D segmentation map [e.g., a reference pelvic bone mask and/or distance map created therefrom that represent a combined pelvic bone region comprising the one or more reference pelvic bone regions (together)]; e.g., wherein refining the 3D pelvic atlas image comprises determining a fine registration transformation by: determining a left-side transformation that aligns (i) a left reference hip bone region of the 3D pelvic atlas image with (ii) a left hip bone region of the 3D segmentation map; determining a right-side transformation that aligns (i) a right reference hip bone region of the 3D pelvic atlas image with (ii) a right hip bone region of the 3D segmentation map; and determining a weighted transformation based on the left-side transformation and the right side transformation; and transforming the 3D pelvic atlas image using the weighted transformation to create the transformed 3D pelvic atlas image}.

In certain embodiments, the method comprises: receiving, at step (c), a plurality of prospective 3D pelvic atlas images;

at step (d): for each particular one of the plurality of prospective 3D pelvic atlas images, determining a first (e.g., coarse) registration transform (e.g., wherein the first registration transform is determined via a coarse registration) to co-register the particular prospective 3D pelvic atlas image with the 3D segmentation map using (i) the one or more reference pelvic bone regions identified within the particular prospective 3D pelvic atlas image and (ii) the one or more pelvic bone regions of the 3D segmentation map and transforming the particular prospective 3D pelvic atlas image according to the first registration transformation (determined for the particular prospective 3D pelvic atlas image), thereby creating a plurality of transformed prospective pelvic atlas images; [e.g., computing, for each transformed prospective pelvic atlas image, a registration quality metric (e.g., a Dice score) (e.g., based on overlap of the reference pelvic bone regions of the pelvic atlas image with the pelvic bone regions of the 3D segmentation map)] selecting a particular one of the transformed prospective pelvic atlas images as an initial best-fit pelvic atlas image [e.g., based on the registration quality metrics computed for each of the transformed prospective pelvic atlas images]; and determining, for the initial best-fit pelvic atlas image, a second registration transform to refine co-registration of the initial best-fit pelvic atlas image with the 3D segmentation map using (i) the one or more reference pelvic bone regions identified initial best-fit pelvic atlas image and (ii) the one or more pelvic bone regions of the 3D segmentation map and transforming the initial best-fit pelvic atlas image according to the second registration transformation, thereby creating a final transformed pelvic atlas image; and using the final transformed pelvic atlas image as the transformed 3D pelvic atlas image to determine, at step (e), the pelvic lymph classification for each of the one or more hotspots {e.g., wherein the first (coarse) registration comprises a registration transformation that that aligns (i) a reference pelvic bone region comprising the one or more reference pelvic bone regions identified within the particular prospective pelvic atlas image [e.g., a reference pelvic bone mask and/or distance map created therefrom that represent a combined pelvic bone region comprising the one or more reference pelvic bones (together)] to (ii) a target pelvic bone region comprising the one or more pelvic bone regions of the 3D segmentation map [e.g., a reference pelvic bone mask and/or distance map created therefrom that represent a combined pelvic bone region comprising the one or more reference pelvic bone regions (together)]; e.g., wherein determining the second (e.g., fine) registration transform comprises determining a fine registration transformation by: determining a left-side transformation that aligns (i) a left reference hip bone region of the initial best-fit pelvic atlas image with (ii) a left hip bone region of the 3D segmentation map; determining a right-side transformation that aligns (i) a right reference hip bone region of the initial best-fit pelvic atlas image with (ii) a right hip bone region of the 3D segmentation map; and determining a weighted transformation based on the left-side transformation and the right side transformation}.

In certain embodiments, the one or more reference pelvic bone regions identified within the pelvic atlas image comprise one or more members selected from the group consisting of a right hip bone region (e.g., representing a segmented right hip bone), a left hip bone (e.g., representing a segmented left hip bone), a sacrum region (e.g., representing a segmented sacrum), a coccyx region (e.g., representing a segmented coccyx), and a (e.g., combined) sacrum and coccyx region.

In certain embodiments, the one or more pelvic lymph sub-regions comprise one or more members selected from the group consisting of: a left internal iliac region, a right internal iliac region, a left external iliac region, a right external iliac region, a left common iliac region, a right common iliac region, a left obturator region, a right obturator region, and a presacral region.

In certain embodiments, the one or more pelvic bone regions of the 3D segmentation map comprise one or more members selected from the group consisting of a right hip bone region (e.g., representing a segmented right hip bone), a left hip bone (e.g., representing a segmented left hip bone), a sacrum region (e.g., representing a segmented sacrum), a coccyx region (e.g., representing a segmented coccyx), and a (e.g., combined) sacrum and coccyx region.

In another aspect, the invention is directed to a method for automatically processing 3D images of a subject to identify and/or characterize cancerous lesions within the subject, the method comprising: (a) receiving, by a processor of a computing device, (i) a 3D functional image of the subject obtained using a functional imaging modality and (ii) a 3D anatomical image of the subject obtained using an anatomical imaging modality, wherein the 3D functional image and the 3D anatomical image are co-registered and include a representation of at least a portion of a torso of the subject, and wherein the 3D functional image includes one or more hotspots representing potential lesions within the portion of the torso of the subject; (b) segmenting, by the processor, the 3D anatomical image to identify a plurality of volumes of interest within the 3D anatomical image of the subject, each VOI corresponding to a particular target tissue region [e.g., a thoracic spine and/or portion thereof (e.g., one or more thoracic vertebrae), a liver, etc.]; (c) determining, by the processor, one or more whole-body landmarks (e.g., a medial line of a thoracic spine in a coronal plane and a superior point of a liver in a corresponding sagittal plane) using the VOIs; and (d) determining, by the processor, for each of the one or more hotspots of the 3D functional image, a distant metastases classification using the one or more whole-body landmarks (e.g., by classifying hotspots lying above an identified superior point of a liver as supradiaphragmatic and classifying hotspots lying below the superior point of the liver as retroperitoneal).

In another aspect, the invention is directed to a method for automatically processing a 3D anatomical image of a subject to identify one or more pelvic lymph regions therein, the method comprising: (a) receiving, by a processor of a computing device, the 3D anatomical image of the subject, the 3D anatomical image having been obtained using an anatomical imaging modality (e.g., CT; e.g., MRI) and including a representation of a pelvic region of the subject; (b) segmenting, by the processor, the 3D anatomical image of the subject to identify representations of one or more pelvic bones within the 3D anatomical image of the subject, thereby creating a 3D segmentation map aligned with the 3D anatomical image of the subject and comprising one or more pelvic bone regions (e.g., labeled segmentation masks), wherein each pelvic bone region corresponds to a particular pelvic bone and/or group of one or more pelvic bones and identifies a representation of the particular pelvic bone and/or group of one or more pelvic bones within the 3D anatomical image; (c) receiving, by the processor, a 3D pelvic atlas image comprising: (A) an identification (e.g., one or more segmentation masks; e.g., one or more 3D segmentation masks, e.g., a segmentation map) of one or more pelvic lymph sub-regions in the 3D pelvic atlas image [e.g., wherein each pelvic lymph sub-region is a segmented region that identifies a particular anatomical structure (e.g., an internal iliac (e.g., a left and/or right internal iliac), an external iliac (e.g., a left and/or right external iliac), a common iliac (e.g., a left and/or right common iliac), an obturator, a presacral) and/or that identifies a sub-volume corresponding to a local region surrounding a particular anatomical structure (e.g., a left/right internal iliac, a left/right external iliac, a left/right common iliac, an obturator, a presacral)] (e.g., each pelvic lymph sub-region identified by a particular segmentation mask); and (B) an identification (e.g., one or more segmentation masks; e.g., one or more 3D segmentation masks, e.g., a segmentation map) of one or more reference pelvic bone regions in the 3D pelvic atlas image, wherein at least a portion of the one or more reference pelvic bone regions in the 3D pelvic atlas image corresponds to (e.g., depicts a same particular pelvic bone or group of one or more pelvic bones) one or more of the pelvic bone regions of the 3D segmentation map; (d) transforming (e.g., applying a coordinate transform to), by the processor, the 3D pelvic atlas image to co-register it with the 3D segmentation map using (i) the one or more reference pelvic bone regions identified within the pelvic atlas image and (ii) the one or more pelvic bone regions of the 3D segmentation map (e.g., as landmarks), thereby creating a transformed 3D pelvic atlas image comprising the identified one or more pelvic lymph sub-regions thereby aligned to the 3D anatomical image and segmentation thereof; and (e) storing and/or providing (e.g., for further processing and/or display), by the processor, the transformed 3D pelvic atlas image.

In another aspect, the invention is directed to a system for automatically processing 3D images of a subject to identify and/or characterize cancerous lesions within the subject, the system comprising: a processor of a computing device; and a memory having instructions stored thereon, wherein the instructions, when executed by the processor, cause the processor to: (a) receive (i) a 3D functional image of the subject obtained using a functional imaging modality and (ii) a 3D anatomical image of the subject obtained using an anatomical imaging modality, wherein the 3D functional image and the 3D anatomical image are aligned [e.g., the 3D functional image and the 3D anatomical image having been acquired using a (e.g., single) multimodal imaging system (e.g., a PET/CT imaging system; e.g., a SPECT/CT imaging system); e.g., the 3D functional image and the 3D anatomical image having been acquired separately and subsequently co-registered] and include a representation of a pelvic region of the subject, and wherein the 3D functional image includes one or more hotspots representing potential lesions within the pelvic region of the subject; (b) segment the 3D anatomical image of the subject to identify representations of one or more pelvic bones within the 3D anatomical image of the subject, thereby creating a 3D segmentation map aligned with the 3D anatomical image of the subject and comprising one or more (e.g., labeled) pelvic bone regions, wherein each pelvic bone region corresponds to a particular pelvic bone and/or group of one or more pelvic bones and identifies a representation of the particular pelvic bone and/or group of one or more pelvic bones within the 3D anatomical image; (c) receive a 3D pelvic atlas image comprising: (A) an identification (e.g., one or more segmentation masks; e.g., one or more 3D segmentation masks, e.g., a segmentation map) of one or more pelvic lymph sub-regions in the 3D pelvic atlas image [e.g., wherein each pelvic lymph sub-region is a segmented region that identifies a particular anatomical structure (e.g., an internal iliac (e.g., a left and/or right internal iliac), an external iliac (e.g., a left and/or right external iliac), a common iliac (e.g., a left and/or right common iliac), an obturator, a presacral) and/or that identifies a sub-volume corresponding to a local region surrounding a particular anatomical structure (e.g., a left/right internal iliac, a left/right external iliac, a left/right common iliac, an obturator, a presacral)] (e.g., each pelvic lymph sub-region identified by a particular segmentation mask); and (B) an identification (e.g., one or more segmentation masks; e.g., one or more 3D segmentation masks, e.g., a segmentation map) of one or more reference pelvic bone regions in the 3D pelvic atlas image, wherein at least a portion of the one or more reference pelvic bone regions in the 3D pelvic atlas image corresponds to (e.g., depicts a same particular pelvic bone or group of one or more pelvic bones) one or more of the pelvic bone regions of the 3D segmentation map; (d) transform (e.g., apply a coordinate transform to) the 3D pelvic atlas image to co-register it with the 3D segmentation map using (i) the one or more reference pelvic bone regions identified within the pelvic atlas image and (ii) the one or more pelvic bone regions of the 3D segmentation map (e.g., as landmarks), thereby creating a transformed 3D pelvic atlas image comprising the identified one or more pelvic lymph sub-regions thereby aligned to the 3D anatomical image and segmentation thereof (e.g., the 3D segmentation map); and (e) determine for each of the one or more hotspots of the 3D functional image, a pelvic lymph classification using the identification of the one or more pelvic lymph sub-regions within the transformed 3D pelvic atlas image [e.g., by identifying each particular hotspot of the one or more hotspots as lying within and/or overlapping with and/or in proximity to a particular pelvic lymph sub-region (e.g., based on a determination that the particular hotspot is located within and/or is located closest to a particular pelvic lymph sub-region)].

In certain embodiments, the 3D functional image is a positron emission tomography (PET) image obtained following administration, to the subject, of a radiopharmaceutical [e.g., a radiopharmaceutical comprising a PSMA binding agent (e.g., [18F]DCFPyL, [18F]DCFBC, $^{68}$Ga-PSMA-11 (also known as $^{68}$Ga-PSMA-HBED-CC), $^{68}$Ga-PSMA-617, PSMA I&T, 18F-PSMA-1007, 18F-JK-PSMA-7)] (e.g., and wherein the 3D anatomical image is a CT image).

In certain embodiments, the radiopharmaceutical comprises a Prostate Specific Membrane Antigen (PSMA) binding agent.

In certain embodiments, the 3D anatomical image is a CT image.

In certain embodiments, at step (c), the instructions cause the processor to select the 3D pelvic atlas image from a set of multiple prospective 3D pelvic atlas images (e.g., multiple different 3D pelvic atlas image options, e.g., reflecting different subject body types, height/weights ranges, etc.).

In certain embodiments, the 3D pelvic atlas image comprises (e.g., as the identification of the one or more pelvic lymph sub-regions) one or more reference markers [e.g., 2D surfaces (e.g., planar surfaces, e.g., curved surfaces)], each of which demarks a boundary between two or more of the pelvic lymph sub-regions, thereby identifying the one or more pelvic lymph sub-regions within the 3D pelvic atlas image.

In certain embodiments, the 3D pelvic atlas image comprises (e.g., as the identification of the one or more pelvic lymph sub-regions) one or more representations of extended sub-volumes, each extended sub-volume corresponding to a particular one of the one or more pelvic lymph sub-regions and representing a local volume about a particular pelvic lymph node, thereby identifying the one or more pelvic lymph sub-regions within the 3D pelvic atlas image.

In certain embodiments, the 3D pelvic atlas image comprises (e.g., as the identification of the one or more pelvic lymph sub-regions) a 3D pelvic lymph segmentation map that identifies one or more pelvic lymph nodes.

In certain embodiments, at step (d), the instructions cause the processor to: determine a first transformation that aligns (i) a first subset of the one or more reference pelvic bone regions identified within the pelvic atlas image to (ii) a corresponding first subset of the one or more pelvic bone regions of the 3D segmentation map (e.g., as landmarks) (e.g., representing pelvic bones and/or group(s) of pelvic bones on a left side of the subject); determine a second transformation that aligns (i) a second subset of the one or more reference pelvic bone regions identified within the pelvic atlas image to (ii) a corresponding second subset of the one or more pelvic bone regions of the 3D segmentation map (e.g., as landmarks) (e.g., representing pelvic bones and/or group(s) of pelvic bones on a right side of the subject); and determine a final overall transformation based on the first transformation and the second transformation (e.g., as a weighted function of the first transformation and the second transformation), and using the final overall transformation to transform the 3D pelvic atlas image.

In certain embodiments, the instruction cause the processor to: perform steps (c) and (d) for a plurality of prospective 3D pelvic atlas images to determine, for each of the prospective 3D pelvic atlas images, a corresponding transformed version and selecting, by the processor, a particular one of the prospective 3D pelvic atlas images as a best-fit 3D pelvic atlas image [e.g., based on one or more performance metrics computed for each of the prospective 3D pelvic atlas images (e.g., based on the transformed version of each of the prospective 3D pelvic atlas images)]; and use the transformed version of the best-fit 3D pelvic atlas image as the transformed 3D pelvic atlas image to determine, at step (e), the pelvic lymph classification for each of the one or more hotspots.

In certain embodiments, at step (d), the instructions cause the processor to: perform a coarse registration to co-register the 3D pelvic atlas image with the 3D segmentation map using (i) the one or more reference pelvic bone regions identified within the pelvic atlas image and (ii) the one or more pelvic bone regions of the 3D segmentation map; and refine the 3D pelvic atlas image to create the transformed 3D pelvic atlas image {e.g., wherein performing the coarse registration comprises determining a registration transformation that that aligns (i) a reference pelvic bone region comprising the one or more reference pelvic bone regions identified within the 3D pelvic atlas image [e.g., a reference pelvic bone mask and/or distance map created therefrom that represent a combined pelvic bone region comprising the one or more reference pelvic bones (together)] to (ii) a target pelvic bone region comprising the one or more pelvic bone regions of the 3D segmentation map [e.g., a reference pelvic bone mask and/or distance map created therefrom that represent a combined pelvic bone region comprising the one or more reference pelvic bone regions (together)]; e.g., wherein refining the 3D pelvic atlas image comprises determining a fine registration transformation by: determining a left-side transformation that aligns (i) a left reference hip bone region of the 3D pelvic atlas image with (ii) a left hip bone region of the 3D segmentation map; determining a right-side transformation that aligns (i) a right reference hip bone region of the 3D pelvic atlas image with (ii) a right hip bone region of the 3D segmentation map; and determining a weighted transformation based on the left-side transformation and the right side transformation; and transforming the 3D pelvic atlas image using the weighted transformation to create the transformed 3D pelvic atlas image}.

In certain embodiments, the instructions cause the processor to: receive, at step (c), a plurality of prospective 3D pelvic atlas images; at step (d): for each particular one of the plurality of prospective 3D pelvic atlas images, determine a first (e.g., coarse) registration transform (e.g., wherein the first registration transform is determined via a coarse registration) to co-register the particular prospective 3D pelvic atlas image with the 3D segmentation map using (i) the one or more reference pelvic bone regions identified within the particular prospective 3D pelvic atlas image and (ii) the one or more pelvic bone regions of the 3D segmentation map and transforming the particular prospective 3D pelvic atlas image according to the first registration transformation (determined for the particular prospective 3D pelvic atlas image), thereby creating a plurality of transformed prospective pelvic atlas images; [e.g., compute, for each transformed prospective pelvic atlas image, a registration quality metric (e.g., a Dice score) (e.g., based on overlap of the reference pelvic bone regions of the pelvic atlas image with the pelvic bone regions of the 3D segmentation map)] select a particular one of the transformed prospective pelvic atlas images as an initial best-fit pelvic atlas image [e.g., based on the registration quality metrics computed for each of the transformed prospective pelvic atlas images]; and determine, for the initial best-fit pelvic atlas image, a second registration transform to refine co-registration of the initial best-fit pelvic atlas image with the 3D segmentation map using (i) the one or more reference pelvic bone regions identified initial best-fit pelvic atlas image and (ii) the one or more pelvic bone regions of the 3D segmentation map and transforming the initial best-fit pelvic atlas image according to the second registration transformation, thereby creating a final transformed pelvic atlas image; and using the final transformed pelvic atlas image as the transformed 3D pelvic atlas image to determine, at step (e), the pelvic lymph classification for each of the one or more hotspots {e.g., wherein the first (coarse) registration comprises a registration transformation that that aligns (i) a reference pelvic bone region comprising the one or more reference pelvic bone regions identified within the particular prospective pelvic atlas image [e.g., a reference pelvic bone mask and/or distance map created therefrom that represent a combined pelvic bone region comprising the one or more reference pelvic bones (together)] to (ii) a target pelvic bone region comprising the one or more pelvic bone regions of the 3D segmentation map [e.g., a reference pelvic bone mask and/or distance map created therefrom that represent a combined pelvic bone region comprising the one or more reference pelvic bone regions (together)]; e.g., wherein determining the second (e.g., fine) registration transform comprises determining a fine registration transformation by: determining a left-side transformation that aligns (i) a left reference hip bone region of the initial best-fit pelvic atlas image with (ii) a left hip bone region of the 3D segmentation map; determining a right-side transformation that aligns (i) a right reference hip bone region of the initial best-fit pelvic atlas image with (ii) a right hip bone region of the 3D segmentation map; and determining a weighted transformation based on the left-side transformation and the right side transformation}.

In certain embodiments, the one or more reference pelvic bone regions identified within the pelvic atlas image comprise one or more members selected from the group consisting of a right hip bone region (e.g., representing a segmented right hip bone), a left hip bone (e.g., representing a segmented left hip bone), a sacrum region (e.g., representing a segmented sacrum), a coccyx region (e.g., representing a segmented coccyx), and a (e.g., combined) sacrum and coccyx region.

In certain embodiments, the one or more pelvic lymph sub-regions comprise one or more members selected from the group consisting of: a left internal iliac region, a right internal iliac region, a left external iliac region, a right external iliac region, a left common iliac region, a right common iliac region, a left obturator region, a right obturator region, and a presacral region.

In certain embodiments, the one or more pelvic bone regions of the 3D segmentation map comprise one or more members selected from the group consisting of a right hip bone region (e.g., representing a segmented right hip bone), a left hip bone (e.g., representing a segmented left hip bone), a sacrum region (e.g., representing a segmented sacrum), a coccyx region (e.g., representing a segmented coccyx), and a (e.g., combined) sacrum and coccyx region.

In another aspect, the invention is directed to a system for automatically processing 3D images of a subject to identify and/or characterize cancerous lesions within the subject, the system comprising: a processor of a computing device; and a memory having instructions stored thereon, wherein the instructions, when executed by the processor, cause the processor to: (a) receive (i) a 3D functional image of the subject obtained using a functional imaging modality and (ii) a 3D anatomical image of the subject obtained using an anatomical imaging modality, wherein the 3D functional image and the 3D anatomical image are co-registered and include a representation of at least a portion of a torso of the subject, and wherein the 3D functional image includes one or more hotspots representing potential lesions within the portion of the torso of the subject; (b) segment the 3D anatomical image to identify a plurality of volumes of interest within the 3D anatomical image of the subject, each VOI corresponding to a particular target tissue region [e.g., a thoracic spine and/or portion thereof (e.g., one or more thoracic vertebrae), a liver, etc.]; (c) determine one or more whole-body landmarks (e.g., a medial line of a thoracic spine in a coronal plane and a superior point of a liver in a corresponding sagittal plane) using the VOIs; and (d) determine, for each of the one or more hotspots of the 3D functional image, a distant metastases classification using the one or more whole-body landmarks (e.g., by classifying hotspots lying above an identified superior point of a liver as supradiaphragmatic and classifying hotspots lying below the superior point of the liver as retroperitoneal).

In another aspect, the invention is directed to a system for automatically processing a 3D anatomical image of a subject to identify one or more pelvic lymph regions therein, the system comprising: a processor of a computing device; and a memory having instructions stored thereon, wherein the instructions, when executed by the processor, cause the processor to: (a) receive the 3D anatomical image of the subject, the 3D anatomical image having been obtained using an anatomical imaging modality (e.g., CT; e.g., MRI) and including a representation of a pelvic region of the subject; (b) segment the 3D anatomical image of the subject to identify representations of one or more pelvic bones within the 3D anatomical image of the subject, thereby creating a 3D segmentation map aligned with the 3D anatomical image of the subject and comprising one or more pelvic bone regions (e.g., labeled segmentation masks), wherein each pelvic bone region corresponds to a particular pelvic bone and/or group of one or more pelvic bones and identifies a representation of the particular pelvic bone and/or group of one or more pelvic bones within the 3D anatomical image; (c) receive a 3D pelvic atlas image comprising: (A) an identification (e.g., one or more segmentation masks; e.g., one or more 3D segmentation masks, e.g., a segmentation map) of one or more pelvic lymph sub-regions in the 3D pelvic atlas image [e.g., wherein each pelvic lymph sub-region is a segmented region that identifies a particular anatomical structure (e.g., an internal iliac (e.g., a left and/or right internal iliac), an external iliac (e.g., a left and/or right external iliac), a common iliac (e.g., a left and/or right common iliac), an obturator, a presacral) and/or that identifies a sub-volume corresponding to a local region surrounding a particular anatomical structure (e.g., a left/ right internal iliac, a left/right external iliac, a left/right common iliac, an obturator, a presacral)] (e.g., each pelvic lymph sub-region identified by a particular segmentation mask); and (B) an identification (e.g., one or more segmentation masks; e.g., one or more 3D segmentation masks, e.g., a segmentation map) of one or more reference pelvic bone regions in the 3D pelvic atlas image, wherein at least a portion of the one or more reference pelvic bone regions in the 3D pelvic atlas image corresponds to (e.g., depicts a same particular pelvic bone or group of one or more pelvic bones) one or more of the pelvic bone regions of the 3D segmentation map; (d) transform (e.g., apply a coordinate transform to) the 3D pelvic atlas image to co-register it with the 3D segmentation map using (i) the one or more reference pelvic bone regions identified within the pelvic atlas image and (ii) the one or more pelvic bone regions of the 3D segmentation map (e.g., as landmarks), thereby creating a transformed 3D pelvic atlas image comprising the identified one or more pelvic lymph sub-regions thereby aligned to the 3D anatomical image and segmentation thereof; and (e) store and/or provide (e.g., for further processing and/or display) the transformed 3D pelvic atlas image.

In another aspect, the invention is directed to a method for automatically processing 3D images of a subject to identify one or more pelvic lymph regions therein, the method comprising: (a) receiving, by a processor of a computing device, (i) a 3D functional image (e.g., a 3D PET image) of the subject obtained using a functional imaging modality (e.g., a PET scanner, e.g., of a multimodal imaging system) and (ii) a 3D anatomical image (e.g., a CT image) of the subject obtained using an anatomical imaging modality (e.g., a CT scanner, e.g., of a multimodal imaging system), wherein the 3D functional image and the 3D anatomical image are aligned [e.g., the 3D functional image and the 3D anatomical image having been acquired using a (e.g., single) multimodal imaging system (e.g., a PET/CT imaging system; e.g., a SPECT/CT imaging system); e.g., the 3D functional image and the 3D anatomical image having been acquired separately and subsequently co-registered] and include a representation of a pelvic region of the subject, and wherein the 3D functional image includes one or more hotspots representing potential lesions within the pelvic region of the subject; (b) segmenting [e.g., using one or more machine learning modules, such as convolutional neural networks (CNNs)], by the processor, the 3D anatomical image of the subject to identify representations of one or more pelvic bones within the 3D anatomical image of the subject, thereby creating a 3D segmentation map aligned with the 3D anatomical image of the subject and comprising one or more (e.g., labeled) pelvic bone regions (e.g., a left hip bone region, a right hip bone region, and a sacrum and coccyx region), wherein each pelvic bone region corresponds to a particular pelvic bone and/or group of one or more pelvic bones (e.g., a left hip bone, a right hip bone, and a sacrum and coccyx) and identifies a representation of the particular pelvic bone and/or group of one or more pelvic bones within the 3D anatomical image, and wherein the one or more pelvic bone regions comprise a left hip bone region that identifies a representation of a left hip bone within the 3D anatomical image and a right hip bone region that identifies a representation of a right hip bone within the 3D anatomical image; (c) receiving, by the processor, a plurality of prospective 3D pelvic atlas images, each particular prospective 3D pelvic atlas image comprising: (A) an identification of one or more pelvic lymph sub-regions in the particular prospective 3D pelvic atlas image [e.g., one or more segmented anatomical structures, extended sub-volumes, and or reference markers (e.g., planar reference markers) identifying one or more members selected from the group consisting of an internal iliac region (e.g., a left and/or right internal iliac region), an external iliac region (e.g., a left and/or right external iliac region), a common iliac region (e.g., a left and/or right common iliac region), an obturator (e.g., a left and/or right obturator region), and a presacral region]; and (B) an identification of one or more reference pelvic bone regions in the particular 3D pelvic atlas image, wherein the one or more reference pelvic bone regions comprise a left reference hip bone region corresponding to the left hip bone region of the 3D segmentation map and a right reference hip bone region corresponding to the right hip bone region of the 3D segmentation map; (d) for each particular prospective pelvic atlas image of the plurality of prospective 3D pelvic atlas images, determining, by the processor, a corresponding coarse registration transformation that aligns (i) a reference pelvic bone region comprising the one or more reference pelvic bone regions identified within the particular prospective pelvic atlas image [e.g., a reference pelvic bone mask and/or distance map created therefrom that represent a combined pelvic bone region comprising the one or more reference pelvic bones (together)] to (ii) a target pelvic bone region comprising the one or more pelvic bone regions of the 3D segmentation map [e.g., a reference pelvic bone mask and/or distance map created therefrom that represent a combined pelvic bone region comprising the one or more reference pelvic bone regions (together)]; (e) transforming, by the processor, each one of the plurality of prospective 3D pelvic atlas images according to its corresponding coarse registration transformation to create a plurality of transformed prospective pelvic atlas images; (f) selecting, by the processor, a best-fit pelvic atlas image from the plurality of prospective 3D pelvic atlas images based on the plurality of transformed prospective pelvic atlas images [e.g., in comparison with the 3D segmentation map (e.g., by computing, for each transformed prospective pelvic atlas image, a similarity/alignment measure (e.g., a Dice score) between reference pelvic bone region, having been transformed, within the transformed prospective pelvic atlas image and the target pelvic bone image and selecting, as the best-fit pelvic atlas image, the prospective pelvic atlas image having the highest similarity/alignment measure)]; (g) determining, by the processor, a fine registration transformation for the best-fit pelvic atlas image by: determining a left-side transformation that aligns (i) the left reference hip bone region of the best-fit pelvic atlas image with (ii) the left hip bone region of the 3D segmentation map; determining a right-side transformation that aligns (i) the right reference hip bone region of the best-fit pelvic atlas image with (ii) the right hip bone region of the 3D segmentation map; and determining a weighted transformation based on the left-side transformation and the right side transformation; (h) transforming, by the processor, the best-fit pelvic atlas image using the weighted transformation to create a final transformed pelvic atlas image; and (i) determining, by the processor, for each of the one or more hotspots of the 3D functional image, a pelvic lymph classification using the identification of the one or more pelvic lymph sub-regions within the final transformed 3D pelvic atlas image [e.g., by identifying each particular hotspot of the one or more hotspots as lying within and/or overlapping with and/or in proximity to a particular pelvic lymph sub-region (e.g., based on a determination that the particular hotspot is located within and/or is located closest to a particular pelvic lymph sub-region)].

In certain embodiments, the one or more pelvic bone regions of the 3D segmentation map comprise a sacrum and coccyx region identifying a representation of sacrum and coccyx bones within the 3D anatomical image; the one or more pelvic lymph sub-regions comprise a presacral region (e.g., corresponding to a presacral lymph node, located in proximity to a sacrum of the subject); the one or more reference pelvic bone regions of the pelvic atlas images comprise a reference sacrum and coccyx region; step (d) comprises, for each particular prospective pelvic atlas image, determining, as the corresponding coarse registration transformation, a transformation that aligns (i) a reference pelvic bone region comprising the left reference hip bone region, the right reference hip bone region, and the reference sacrum and coccyx region within the particular prospective pelvic atlas image to (ii) a target pelvic bone region comprising the left hip bone region, the right hip bone region, and the sacrum and coccyx region of the 3D segmentation map; and step (g) comprises combining the weighted transformation with the coarse registration transformation determined for the best-fit pelvic atlas image at step (d) by applying the coarse registration transformation to transform the presacral region of the best-fit pelvic atlas image and applying the weighted transformation to transform other regions (e.g., outside the presacral region) of the best-fit pelvic atlas image.

In another aspect, the invention is directed to a system for automatically processing 3D images of a subject to identify one or more pelvic lymph regions therein, the system comprising: a processor of a computing device; and a memory having instructions stored thereon, wherein the instructions, when executed by the processor, cause the processor to: (a) receive (i) a 3D functional image (e.g., a 3D PET image) of the subject obtained using a functional imaging modality (e.g., a PET scanner, e.g., of a multimodal imaging system) and (ii) a 3D anatomical image (e.g., a CT image) of the subject obtained using an anatomical imaging modality (e.g., a CT scanner, e.g., of a multimodal imaging system), wherein the 3D functional image and the 3D anatomical image are aligned [e.g., the 3D functional image and the 3D anatomical image having been acquired using a (e.g., single) multimodal imaging system (e.g., a PET/CT imaging system; e.g., a SPECT/CT imaging system); e.g., the 3D functional image and the 3D anatomical image having been acquired separately and subsequently co-registered] and include a representation of a pelvic region of the subject, and wherein the 3D functional image includes one or more hotspots representing potential lesions within the pelvic region of the subject; (b) segment [e.g., using one or more machine learning modules, such as convolutional neural networks (CNNs)] the 3D anatomical image of the subject to identify representations of one or more pelvic bones within the 3D anatomical image of the subject, thereby creating a 3D segmentation map aligned with the 3D anatomical image of the subject and comprising one or more (e.g., labeled) pelvic bone regions (e.g., a left hip bone region, a right hip bone region, and a sacrum and coccyx region), wherein each pelvic bone region corresponds to a particular pelvic bone and/or group of one or more pelvic bones (e.g., a left hip bone, a right hip bone, and a sacrum and coccyx) and identifies a representation of the particular pelvic bone and/or group of one or more pelvic bones within the 3D anatomical image, and wherein the one or more pelvic bone regions comprise a left hip bone region that identifies a representation of a left hip bone within the 3D anatomical image and a right hip bone region that identifies a representation of a right hip bone within the 3D anatomical image; (c) receive a plurality of prospective 3D pelvic atlas images, each particular prospective 3D pelvic atlas image comprising: (A) an identification of one or more pelvic lymph sub-regions in the particular prospective 3D pelvic atlas image [e.g., one or more segmented anatomical structures, extended sub-volumes, and or reference markers (e.g., planar reference markers) identifying one or more members selected from the group consisting of an internal iliac region (e.g., a left and/or right internal iliac region), an external iliac region (e.g., a left and/or right external iliac region), a common iliac region (e.g., a left and/or right common iliac region), an obturator (e.g., a left and/or right obturator region), and a presacral region]; and (B) an identification of one or more reference pelvic bone regions in the particular 3D pelvic atlas image, wherein the one or more reference pelvic bone regions comprise a left reference hip bone region corresponding to the left hip bone region of the 3D segmentation map and a right reference hip bone region corresponding to the right hip bone region of the 3D segmentation map; (d) for each particular prospective pelvic atlas image of the plurality of prospective 3D pelvic atlas images, determine a corresponding coarse registration transformation that aligns (i) a reference pelvic bone region comprising the one or more reference pelvic bone regions identified within the particular prospective pelvic atlas image [e.g., a reference pelvic bone mask and/or distance map created therefrom that represent a combined pelvic bone region comprising the one or more reference pelvic bones (together)] to (ii) a target pelvic bone region comprising the one or more pelvic bone regions of the 3D segmentation map [e.g., a reference pelvic bone mask and/or distance map created therefrom that represent a combined pelvic bone region comprising the one or more reference pelvic bone regions (together)]; (e) transform each one of the plurality of prospective 3D pelvic atlas images according to its corresponding coarse registration transformation to create a plurality of transformed prospective pelvic atlas images; (f) select a best-fit pelvic atlas image from the plurality of prospective 3D pelvic atlas images based on the plurality of transformed prospective pelvic atlas images [e.g., in comparison with the 3D segmentation map (e.g., by computing, for each transformed prospective pelvic atlas image, a similarity/alignment measure (e.g., a Dice score) between reference pelvic bone region, having been transformed, within the transformed prospective pelvic atlas image and the target pelvic bone image and selecting, as the best-fit pelvic atlas image, the prospective pelvic atlas image having the highest similarity/alignment measure)]; (g) determine a fine registration transformation for the best-fit pelvic atlas image by: determining a left-side transformation that aligns (i) the left reference hip bone region of the best-fit pelvic atlas image with (ii) the left hip bone region of the 3D segmentation map; determining a right-side transformation that aligns (i) the right reference hip bone region of the best-fit pelvic atlas image with (ii) the right hip bone region of the 3D segmentation map; and determining a weighted transformation based on the left-side transformation and the right side transformation; (h) transform the best-fit pelvic atlas image using the weighted transformation to create a final transformed pelvic atlas image; and (i) determine, for each of the one or more hotspots of the 3D functional image, a pelvic lymph classification using the identification of the one or more pelvic lymph sub-regions within the final transformed 3D pelvic atlas image [e.g., by identifying each particular hotspot of the one or more hotspots as lying within and/or overlapping with and/or in proximity to a particular pelvic lymph sub-region (e.g., based on a determination that the particular hotspot is located within and/or is located closest to a particular pelvic lymph sub-region)].

In certain embodiments, the one or more pelvic bone regions of the 3D segmentation map comprise a sacrum and coccyx region identifying a representation of sacrum and coccyx bones within the 3D anatomical image; the one or more pelvic lymph sub-regions comprise a presacral region (e.g., corresponding to a presacral lymph node, located in proximity to a sacrum of the subject); the one or more reference pelvic bone regions of the pelvic atlas images comprise a reference sacrum and coccyx region; at step (d), the instructions cause the processor to, for each particular prospective pelvic atlas image, determine, as the corresponding coarse registration transformation, a transformation that aligns (i) a reference pelvic bone region comprising the left reference hip bone region, the right reference hip bone region, and the reference sacrum and coccyx region within the particular prospective pelvic atlas image to (ii) a target pelvic bone region comprising the left hip bone region, the right hip bone region, and the sacrum and coccyx region of the 3D segmentation map; and at step (g), the instructions cause the processor to combine the weighted transformation with the coarse registration transformation determined for the best-fit pelvic atlas image at step (d) by applying the coarse registration transformation to transform the presacral region of the best-fit pelvic atlas image and applying the weighted transformation to transform other regions (e.g., outside the presacral region) of the best-fit pelvic atlas image.

Features of embodiments described with respect to one aspect of the invention may be applied with respect to another aspect of the invention.

BRIEF DESCRIPTION OF THE DRAWING

The patent or application file contains at least one drawing executed in color. Copies of this patent or patent application publication with color drawing(s) will be provided by the Office upon request and payment of the necessary fee.

The foregoing and other objects, aspects, features, and advantages of the present disclosure will become more apparent and better understood by referring to the following description taken in conjunction with the accompanying drawings, in which.

Figure 1:
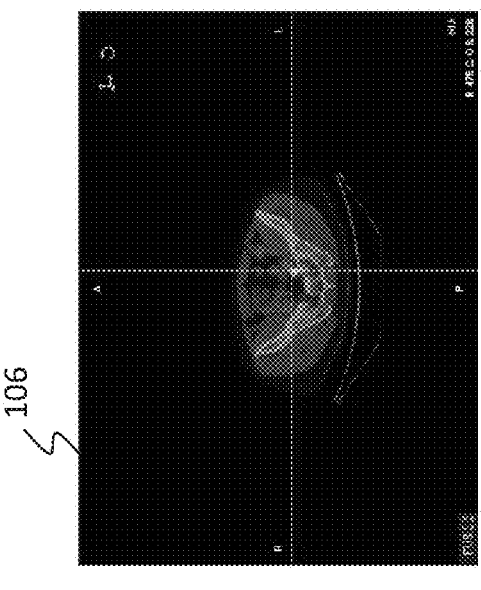
FIG. 1 is a set of corresponding slices of a CT image, a PET image, and a PET/CT fusion, of a PET/CT scan, according to an illustrative embodiment.
Figure 1:
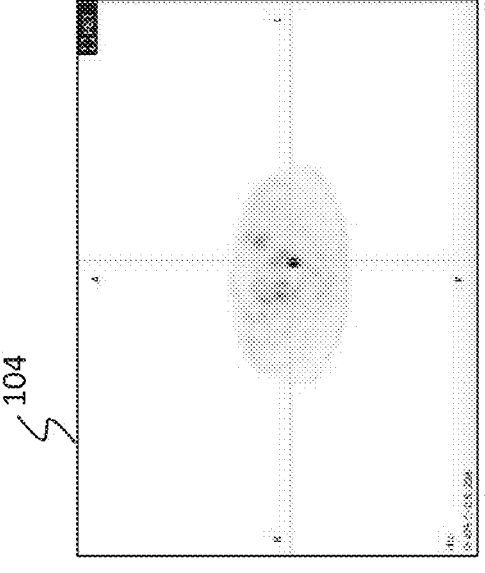
Figure 1:
Figure 1:
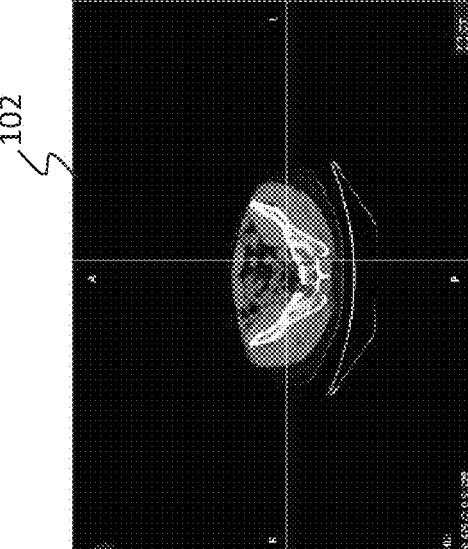

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

CERTAIN DEFINITIONS

In order for the present disclosure to be more readily understood, certain terms are first defined below. Additional definitions for the following terms and other terms are set forth throughout the specification.

A, an: The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

About, approximately: As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

First, second, etc.: It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed or that the first element must precede the second element in some manner In addition, unless stated otherwise, a set of elements may comprise one or more elements.

Image: As used herein, an "image"—for example, a 3D image of subject, includes any visual representation, such as a photo, a video frame, streaming video, as well as any electronic, digital or mathematical analogue of a photo (e.g., a digital image), video frame, or streaming video, displayed or stored in memory (e.g., a digital image may, but need not be displayed for visual inspection). Any apparatus described herein, in certain embodiments, includes a display for displaying an image or any other result produced by the processor. Any method described herein, in certain embodiments, includes a step of displaying an image or any other result produced via the method. In certain embodiments, an image is a 3D image, conveying information that varies with position within a 3D volume. Such images may, for example, be represented digitally as a 3D matrix (e.g., a N×M×L matrix) with each voxel of a 3D image represented by an element of a 3D matrix. Other representations are also contemplated and included, for example, a 3D matrix may be reshaped as a vector (e.g., a 1×K size vector, where K is a total number of voxels) by stitching each row or column end to end. Examples of images include, for example, medical images, such as bone-scan images (also referred to as scintigraphy images), computed tomography (CT) images, magnetic resonance images (MRIs), optical images (e.g., bright-field microscopy images, fluorescence images, reflection or transmission images, etc.), positron emission tomography (PET) images, single-photon emission tomography (SPECT) images, ultrasound images, x-ray images, and the like. In certain embodiments, a medical image is or comprises a nuclear medicine image, produced from radiation emitted from within a subject being imaged. In certain embodiments, a medical image is or comprises an anatomical image (e.g., a 3D anatomical image) conveying information regarding location and extent of anatomical structures such as internal organs, bones, soft-tissue, and blood vessels, within a subject. Examples of anatomical images include, without limitation, x-ray images, CT images, MRIs, and ultrasound images. In certain embodiments, a medical image is or comprises a functional image (e.g., a 3D functional image) conveying information relating to physiological activities within specific organs and/or tissue, such as metabolism, blood flow, regional chemical composition, absorption, etc. Examples of functional images include, without limitation, PET images, SPECT images.

Map: As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume. A three-dimensional map may be displayed in two-dimensions (e.g., on a two-dimensional screen, or on a two-dimensional printout).

Segmentation map: As used herein, the term "segmentation map" refers to a computer representation that identifies one or more 2D or 3D regions determined by segmenting an image. In certain embodiments, a segmentation map distinguishably identifies multiple different (e.g., segmented) regions, allowing them to be individually and distinguishably accessed and operated upon and/or used for operating on, for example, one or more images.

3D, three-dimensional As used herein, "3D" or "three-dimensional" with reference to an "image" means conveying information about three dimensions. A 3D image may be rendered as a dataset in three dimensions and/or may be displayed as a set of two-dimensional representations, or as a three-dimensional representation. In certain embodiments, a 3D image is represented as voxel (e.g., volumetric pixel) data.

Whole body: As used herein, the terms "full body" and "whole body" used (interchangeably) in the context of segmentation and other manners of identification of regions within an image of a subject refer to approaches that evaluate a majority (e.g., greater than 50%) of a graphical representation of a subject's body in a 3D anatomical image to identify target tissue regions of interest. In certain embodiments, full body and whole body segmentation refers to identification of target tissue regions within at least an entire torso of a subject. In certain embodiments, portions of limbs are also included, along with a head of the subject.

Radionuclide: As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{211}$At and $^{192}$Ir.

Radiopharmaceutical: As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

Machine learning module: As used herein, the term "machine learning module" refers to a computer implemented process (e.g., function) that implements one or more specific machine learning algorithms in order to determine, for a given input (such as an image (e.g., a 2D image; e.g., a 3D image), dataset, and the like) one or more output values. For example, a machine learning module may receive as input a 3D image of a subject (e.g., a CT image; e.g., an MRI), and for each voxel of the image, determine a value that represents a likelihood that the voxel lies within a region of the 3D image that corresponds to a representation of a particular organ or tissue of the subject. In certain embodiments, two or more machine learning modules may be combined and implemented as a single module and/or a single software application. In certain embodiments, two or more machine learning modules may also be implemented separately, e.g., as separate software applications. A machine learning module may be software and/or hardware. For example, a machine learning module may be implemented entirely as software, or certain functions of a CNN module may be carried out via specialized hardware (e.g., via an application specific integrated circuit (ASIC)).

Subject: As used herein, a "subject" means a human or other mammal (e.g., rodent (mouse, rat, hamster), pig, cat, dog, horse, primate, rabbit, and the like).

Administering: As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments.

Tissue: As used herein, the term "tissue" refers to bone (osseous tissue) as well as soft-tissue.

DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps. It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are provided for the convenience of the reader—the presence and/or placement of a header is not intended to limit the scope of the subject matter described herein.

A. Nuclear Medicine Images

Nuclear medicine images may be obtained using a nuclear medicine imaging modality such as bone scan imaging (also referred to as scintigraphy), Positron Emission Tomography (PET) imaging, and Single-Photon Emission Tomography (SPECT) imaging.

In certain embodiments, nuclear medicine images are obtained using imaging agents comprising radiopharmaceuticals. Nuclear medicine images may be obtained following administration of a radiopharmaceutical to a patient (e.g., a human subject), and provide information regarding the distribution of the radiopharmaceutical within the patient.

Nuclear medicine imaging techniques detect radiation emitted from the radionuclides of radiopharmaceuticals to form an image. The distribution of a particular radiopharmaceutical within a patient may be influenced and/or dictated by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body. In certain embodiments, intensities of voxels of a nuclear medicine image, for example a PET image, represent standard uptake values (SUVs) (e.g., having been calibrated for injected radiopharmaceutical dose and/or patient weight).

For example, upon administration to a patient, technetium 99m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity—in nuclear medicine images. Accordingly, presence of malignant bone lesions associated with metastatic prostate cancer can be inferred by identifying such hotspots within a whole-body scan of the patient. In certain embodiments, analyzing intensity variations in whole-body scans obtained following administration of $^{99m}$Tc MDP to a patient, such as by detecting and evaluating features of hotspots, can be used to compute, risk indices that correlate with patient overall survival and other prognostic metrics indicative of disease state, progression, treatment efficacy, and the like. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example 18F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells.

In certain embodiments, radiopharmaceuticals that selectively bind to particular proteins or receptors of interest—particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals that comprise PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}Tc$ MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. Risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

Several exemplary PSMA binding agents and radionuclide labelled versions thereof are described in further detail in Section H herein, as well as in U.S. Pat. Nos. 8,778,305, 8,211,401, and 8,962,799, and in U.S. Patent Publication No. US 2021/0032206 A1, the content of each of which are incorporated herein by reference in their entireties.

B. Image Segmentation in Nuclear Medicine Imaging

Nuclear medicine images are functional images. Functional images convey information relating to physiological activities within specific organs and/or tissue, such as metabolism, blood flow, regional chemical composition, and/or absorption. In certain embodiments, nuclear medicine images are acquired and/or analyzed in combination with anatomical images, such as computed tomography (CT) images. Anatomical images provide information regarding location and extent of anatomical structures such as internal organs, bones, soft-tissue, and blood vessels, within a subject. Examples of anatomical images include, without limitation, x-ray images, CT images, magnetic resonance images, and ultrasound images.

Accordingly, in certain embodiments, anatomical images can be analyzed together with nuclear medicine images in order to provide anatomical context for the functional information that they (nuclear medicine images) convey. For example, while nuclear medicine images, such as PET and SPECT convey a three-dimensional distribution of radiopharmaceutical within a subject, adding anatomical context from an anatomical imaging modality, such as CT imaging, allows one to determine the particular organs, soft-tissue regions, bones, etc. that radiopharmaceutical has accumulated in.

For example, a functional image may be aligned with an anatomical image so that locations within each image that correspond to a same physical location—and therefore correspond to each other—can be identified. For example, coordinates and/or pixels/voxels within a functional image and an anatomical image may be defined with respect to a common coordinate system, or a mapping (i.e., a functional relationship) between voxels within the anatomical image and voxels within the functional image established. In this manner, one or more voxels within an anatomical image and one or more voxels within a functional image that represent a same physical location or volume can be identified as corresponding to each other.

For example, FIG. 1 shows axial slices of a 3D CT image 102 and a 3D PET image 104, along with a fused image 106 in which the slice of the 3D CT image is displayed in grayscale and with the PET image is displayed as a semitransparent overlay. By virtue of the alignment between the CT and PET images, a location of a hotspot within the PET image, indicative of accumulated radiopharmaceutical and, accordingly a potential lesion, can be identified in the corresponding CT image, and viewed in anatomical context, for example, within a particular location in the pelvic region (e.g., within a prostate).

In certain embodiments, the aligned pair are a composite image, such as a PET/CT or SPECT/CT. In certain embodiments, an anatomical image (e.g., a 3D anatomical image, such as a CT image) and a functional image (e.g., a 3D functional image, such as a PET or SPECT image) are acquired using separate anatomical and functional imaging modalities, respectively. In certain embodiments, an anatomical image (e.g., a 3D anatomical image, such as a CT image) and a functional image (e.g., a 3D functional image, such as a PET or SPECT image) are acquired using a single multimodality imaging system. A functional image and an anatomical image may, for example, be acquired via two scans using a single multimodal imaging system—for example first performing a CT scan and then, second, performing a PET scan—during which a subject remains in a substantially fixed position.

In certain embodiments, 3D boundaries of particular tissue regions of interest can be accurately identified by analyzing 3D anatomical images. For example, automated segmentation of 3D anatomical images can be performed to segment 3D boundaries of regions such as particular organs, organ sub-regions and soft-tissue regions, as well as bone. In certain embodiments, organs such as a prostate, urinary bladder, liver, aorta (e.g., portions of an aorta, such as a thoracic aorta), a parotid gland, etc., are segmented. In certain embodiments, one or more particular bones are segmented. In certain embodiments, an overall skeleton is segmented.

In certain embodiments, automated segmentation of 3D anatomical images may be performed using one or more machine learning modules that are trained to receive a 3D anatomical image and/or a portion thereof, as input, and segment one or more particular regions of interest, producing a 3D segmentation map as output. For example as described in PCT publication WO/2020/144134, entitled "Systems and Methods for Platform Agnostic Whole Body Segmentation," and published Jul. 16, 2020, the contents of which are incorporated herein by reference in their entirety, multiple machine learning modules implementing convolutional neural networks (CNNs) may be used to segment 3D anatomical images, such as CT images, of a whole body of a subject and thereby create a 3D segmentation map that identifies multiple target tissue regions across a subject's body.

In certain embodiments, for example to segment certain organs where functional images are believed to provide additional useful information that facilitate segmentation, a machine learning module may receive both an anatomical image and a functional image as input, for example as two different channels of input (e.g., analogous to multiple color channels in a color, RGB, image) and use these two inputs to determine an anatomical segmentation. This, multi-channel, approach is described in further detail in U.S. Patent Publication No. US 2021/0334974 A1, entitled "Systems and Methods for Deep-Learning-Based Segmentation of Composite Images," and published Oct. 28, 2021, the contents of which is hereby incorporated by reference in its entirety.

Figure 2:
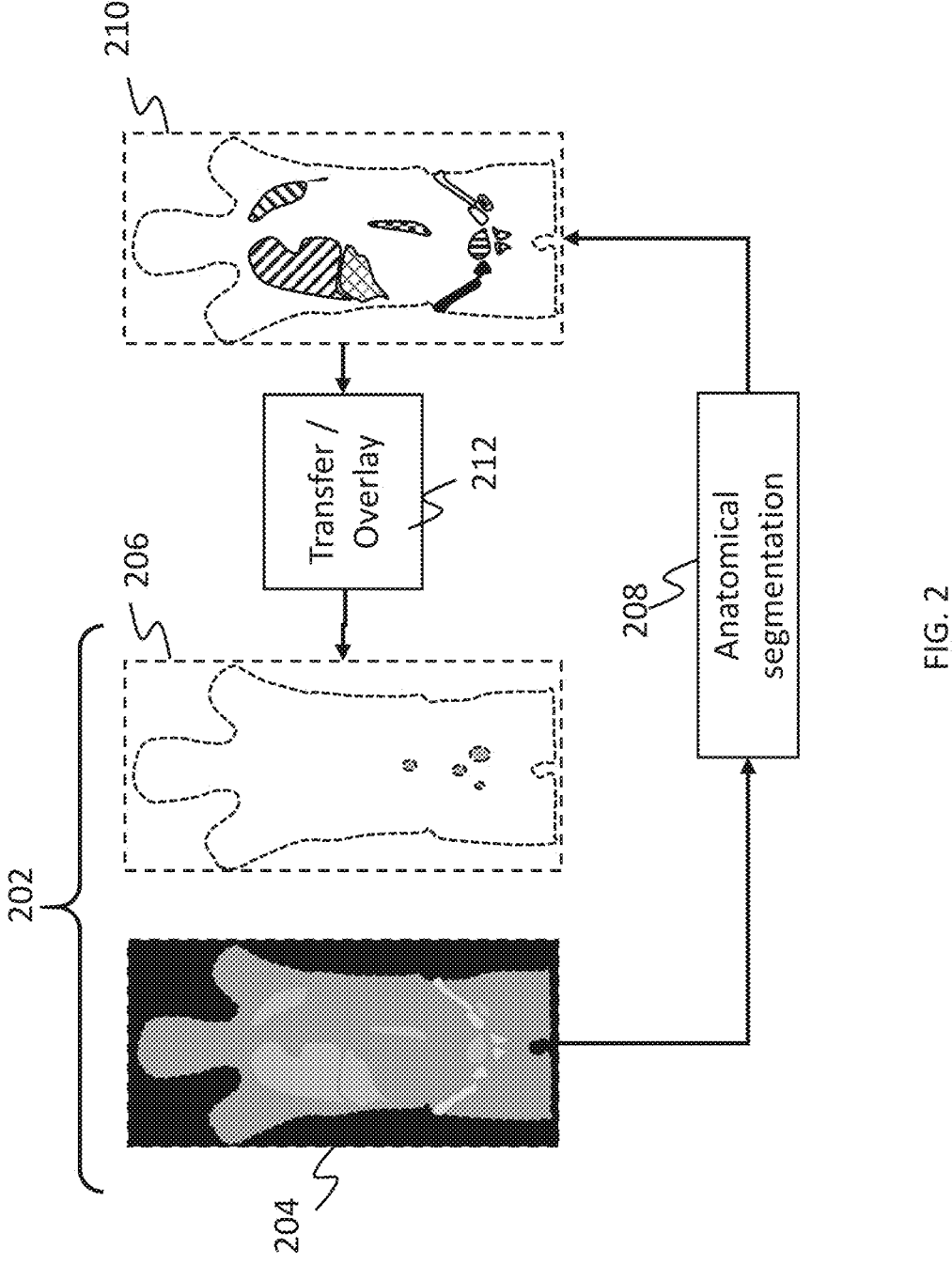
FIG. 2 is a diagram illustrating an example process for segmentation of an anatomical image and identification of anatomical boundaries in a co-aligned functional image, according to an illustrative embodiment.

In certain embodiments, as illustrated FIG. 2, an anatomical image 204 (e.g., a 3D anatomical image, such as a CT image) and a functional image 206 (e.g., a 3D functional image, such as a PET or SPECT image) may be aligned with (e.g., co-registered to) each other, for example as in a composite image such as a PET/CT image. Anatomical image 204 may be segmented to create a segmentation map 210 (e.g., a 3D segmentation map) that distinguishably identifies one or more tissue regions and/or sub-regions of interest, such as one or more particular organs and/or bones. Segmentation map 210, having been created from anatomical image 204 is aligned with anatomical image 204, which, in turn, is aligned with functional image 206. Accordingly, boundaries of particular regions (e.g., segmentation masks), such as particular organs and/or bones, identified via segmentation map 210 can be transferred to and/or overlaid upon functional image 206 to identify volumes within functional image 206 for purposes of classifying hotspots, and determining useful indices that serve as measures and/or predictions of cancer status, progression, and response to treatment. Segmentation maps and masks may also be displayed, for example as a graphical representation overlaid on a medical image to guide physicians and other medical practitioners.

C. Lesion Detection and Characterization

In certain embodiments, approaches described herein allow hotspots identified in 3D functional images, which represent potential lesions to be classified in detailed fashion, based on their spatial relationship with certain pelvic lymph regions. As described herein, in certain embodiments, hotspots are localized (e.g., contiguous) regions of high intensity, relative to their surroundings, within images, such as 3D functional images and may be indicative of a potential cancerous lesion present within a subject.

A variety of approaches may be used for detecting, segmenting, and classifying hotspots. In certain embodiments, hotspots are detected and segmented using analytical methods, such as filtering techniques including, but not limited to, a difference of Gaussians (DoG) filter and a Laplacian of Gaussians (LoG) filter. In certain embodiments, hotspots are segmented using a machine learning module that receives, as input, a 3D functional image, such as a PET image, and generates, as output a hotspot segmentation map (a "hotspot map") that differentiates boundaries of identified hotspots from background. In certain embodiments, each segmented hotspot within a hotspot map is individually identifiable (e.g., individually labelled). In certain embodiments, a machine learning module used for segmenting hotspots may take as input, in addition to a 3D functional image, one or both of a 3D anatomical image (e.g., a CT image) and a 3D anatomical segmentation map. The 3D anatomical segmentation map may generated via automated segmentation (e.g., as described herein) of the 3D anatomical image.

In certain embodiments, segmented hotspots may be classified according to an anatomical region in which they are located. For example, in certain embodiments, locations of individual segmented hotspots within a hotspot map (representing and identifying segmented hotspots) may be compared with 3D boundaries of segmented tissue regions, such as various organs and bones, within a 3D anatomical segmentation map and labeled according to their location, e.g., based on proximity to and/or overlap with particular organs. In certain embodiments, a machine learning module may be used to classify hotspots. For example, in certain embodiments, a machine learning module may generate, as output, a hotspot map in which segmented hotspots are not only individually labeled and identifiable (e.g., distinguishable from each other), but are also labeled, for example, as corresponding to one of a bone, lymph, or prostate lesion. In certain embodiments, one or more machine learning modules may be combined with each other, as well as with analytical segmentation (e.g., thresholding) techniques to perform various tasks in parallel and in sequence to create a final labeled hotspot map.

Various approaches for performing detailed segmentation of 3D anatomical images and identification of hotspots representing lesions in 3D functional images, which may be used with various approaches described herein, are described in PCT publication WO/2020/144134, entitled "Systems and Methods for Platform Agnostic Whole Body Segmentation," and published Jul. 16, 2020, U.S. Patent Publication No. US 2021/0334974 A1, entitled "Systems and Methods for Deep-Learning-Based Segmentation of Composite Images," and published Oct. 28, 2021, and PCT publication WO/2022/008374, entitled "Systems and Methods for Artificial Intelligence-Based Image Analysis for Detection and Characterization of Lesions," and published Jan. 13, 2022, the contents of each of which is incorporated herein in its entirety.

Figure 3:
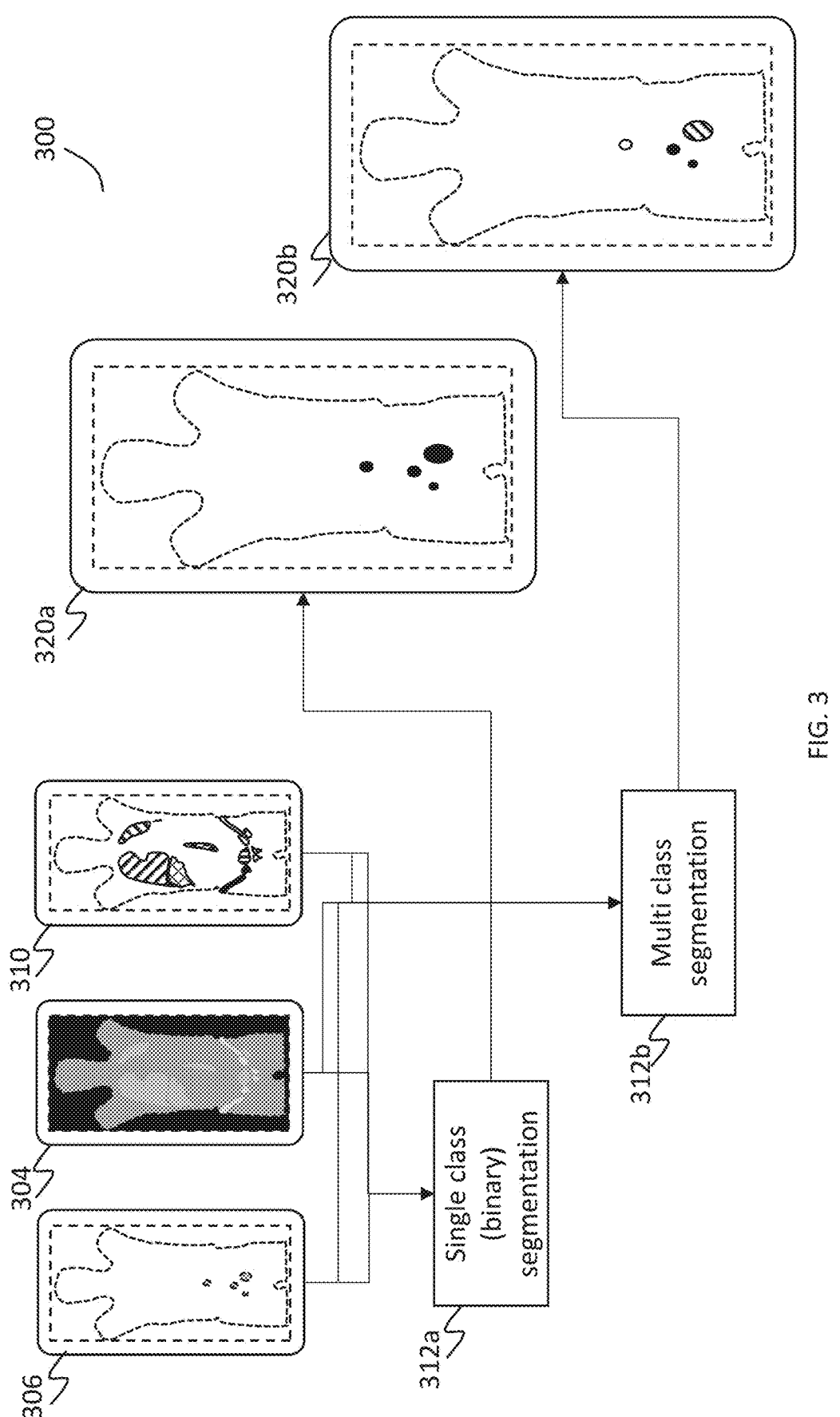
FIG. 3 is a diagram illustrating an example process for segmenting and classifying hotspots, according to an illustrative embodiment.

FIG. 3 shows an example process 300 for segmenting and classifying hotspots, based on an example approach described in further detail in PCT publication WO/2022/008374, entitled "Systems and Methods for Artificial Intelligence-Based Image Analysis for Detection and Characterization of Lesions," and published Jan. 13, 2022. The approach illustrated in FIG. 3 uses two machine learning modules, each of which receives, as input, 3D functional image 306, 3D anatomical image 304, and 3D anatomical segmentation map 310. Machine learning module 312a is a binary classifier, that generates a single-class hotspot map 320a, by labeling voxels as hotspot or background (not a hotspot). Machine learning module 312b performs multiclass segmentation, and generates multi-class hotspot map 320b, in which hotspots are both segmented and labeled as one of three classes—prostate, lymph, or bone. Among other things, classifying hotspots in this manner—via a machine learning module 312b (e.g., as opposed to directly comparing hotspot locations with segmented boundaries from segmentation map 310)—obviates a need to segment certain regions. For example, in certain embodiments, machine learning module 312b may classify hotspots as belonging to prostate, lymph, or bone, without a prostate region having be identified and segmented from 3D anatomical image 304 (e.g., in certain embodiments, 3D anatomical segmentation map 310 does not comprise a prostate region). In certain embodiments, hotspot maps 320a and 320b are merged, for example by transferring labels from multi-class hotspot map 320b to the hotspot segmentations identified in single-class hotspot map 320a (e.g., based on overlap). Without wishing to be bound to any particular theory, it is believed that this approach combines improved segmentation and detection of hotspots from single class machine learning module 312a with classification results from multi-class machine learning module 312b. In certain embodiments, hotspot regions identified via this final, merged, hotspot map are further refined, using an analytical technique such as an adaptive thresholding technique described in PCT publication WO/2022/008374, entitled "Systems and Methods for Artificial Intelligence-Based Image Analysis for Detection and Characterization of Lesions," and published Jan. 13, 2022.

D. Detailed Identification of Pelvic Lymph Regions

Figure 4:
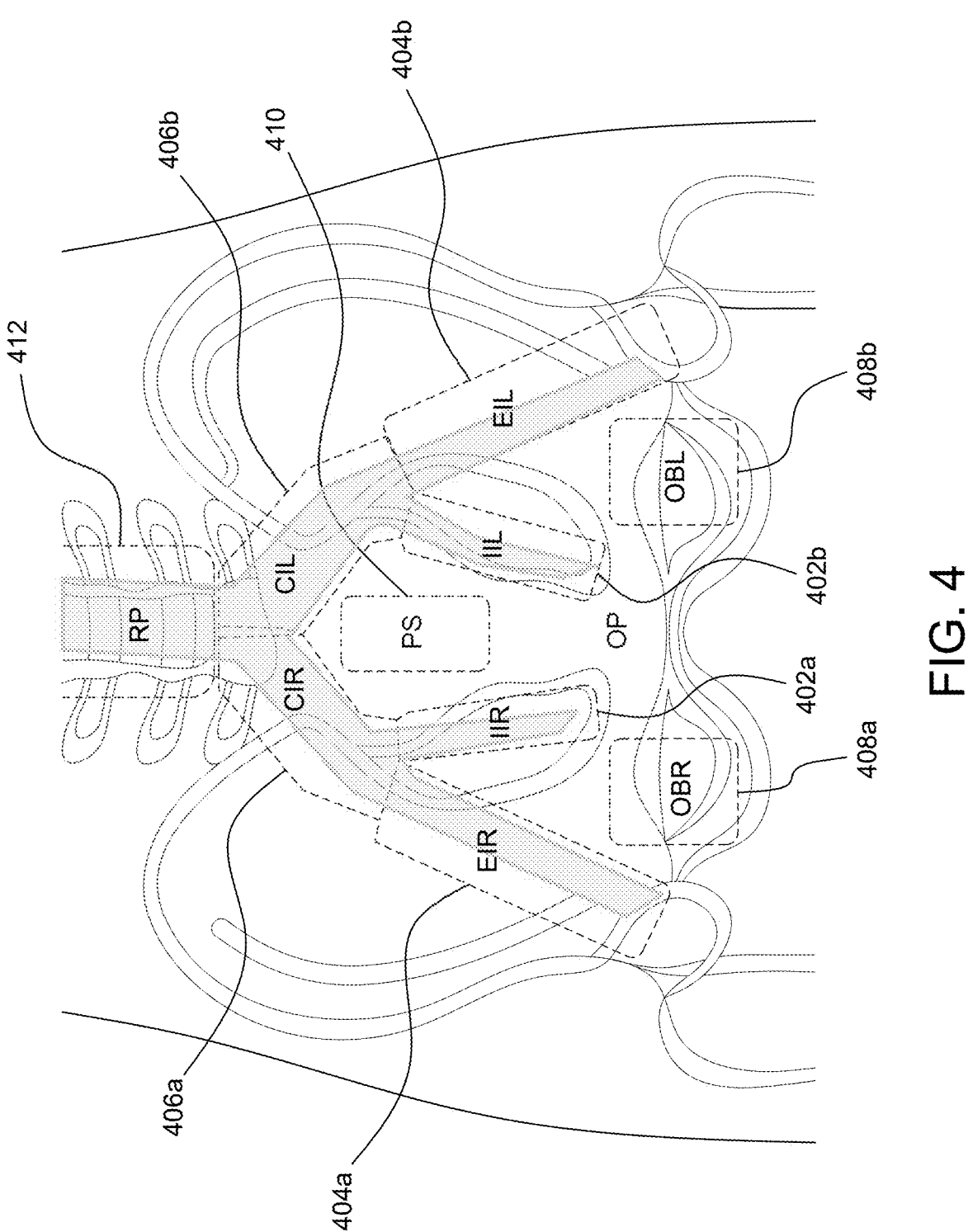
FIG. 4 is a diagram illustrating certain pelvic lymph sub-regions, according to an illustrative embodiment.
Figure 5:
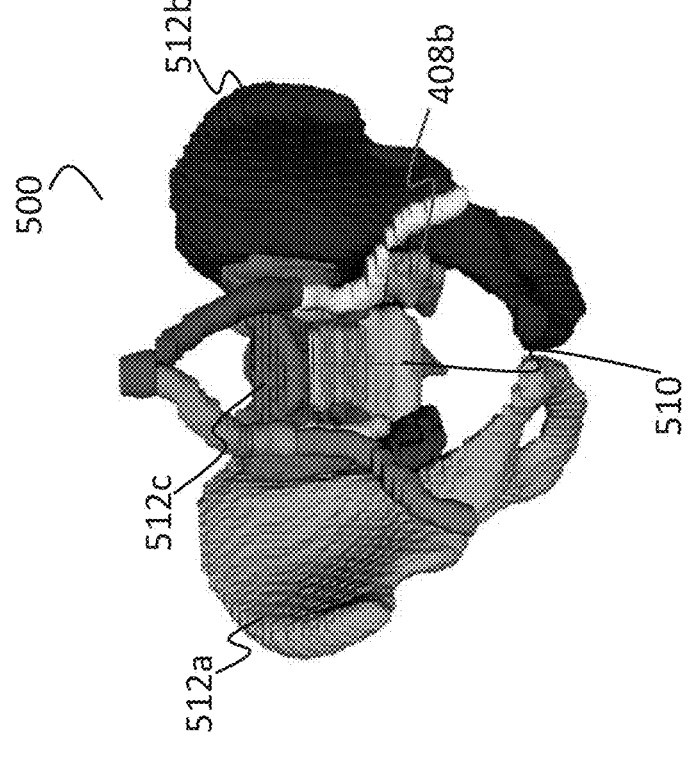
FIG. 5 is a set of two views of a 3D pelvic atlas images, according to an illustrative embodiment.
Figure 5:
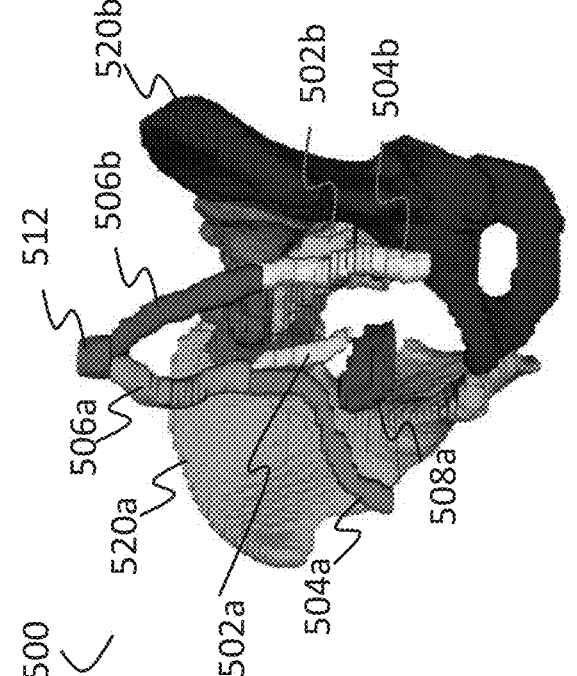

Turning to FIGS. 4, 5, and 6, in certain embodiments, techniques described herein provide for identification of anatomical structures, such as pelvic lymph nodes, and, additionally or alternatively, sub-regions associated with them, that may be challenging to segment accurately based on direct analysis of an anatomical image, alone or in combination with a functional image (e.g., a co-aligned functional image).

FIG. 4 shows schematic of certain pelvic lymph sub-regions, based on and used, in certain embodiments, in connection with a metastases classification framework referred to as "miTNM," and described in Eiber et al., J. Nucl. Med. 2018; 59:469-478, the contents of which in hereby incorporated by reference in its entirety. In particular, FIG. 4 shows pelvic lymph sub-regions, each corresponding to a particular pelvic lymph node, including a right 402a and a left internal iliac 402b (labeled "IIR and "IIL," respectively), a right 404a and a left external iliac 404b (labeled "EIR" and "EIL," respectively), a right 406a and a left common iliac 406b (labeled "CIR" and "CIL," respectively), a right 408a and a left obturator 408b (labeled "OBR" and "OBL," respectively), and a presacral region 410 (labeled "PS"). A portion of a retroperitoneal 412 extra-pelvic region is also shown.

FIG. 5 shows two views of a representation of a 3D segmentation map 500 identifying certain pelvic lymph nodes and bones within a pelvic region. Segmentation map 500 includes representations of pelvic lymph nodes corresponding to the sub-regions described above with respect to FIG. 4—in particular, a right 502a and a left internal iliac 502b, a right 504a and a left external iliac 504b, a right 506a and a left common iliac 506b, a right 508a and a left obturator 508b, and a presacral node 510, along with a portion of retroperitoneal 512 extra-pelvic node. FIG. 5 also includes representations of a right hip bone 512a, a left hip bone 512b, and a sacrum 512c.

Figure 6B:
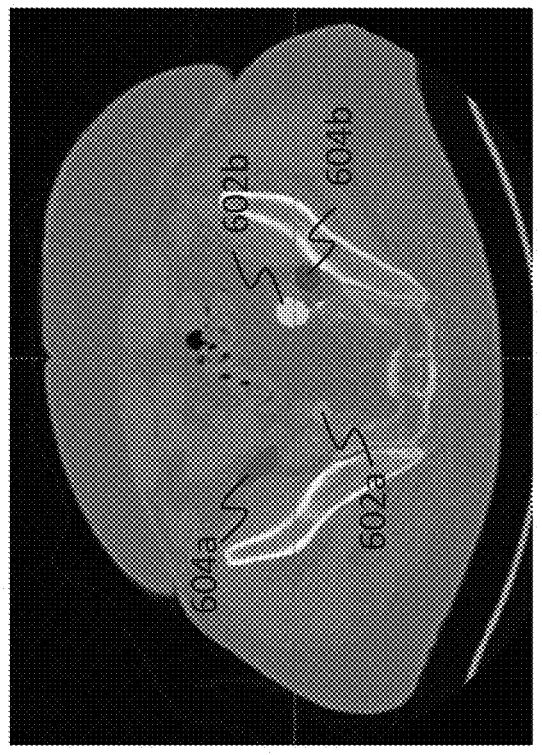
FIG. 6B shows the view of the CT image of FIG. 6A, with identifications of certain iliac arteries shown, according to an illustrative embodiment.
Figure 6A:
FIG. 6A is a view of a CT image, according to an illustrative embodiment.

FIG. 6A shows an axial slice of a low-dose CT image, within a pelvic region of a subject. FIG. 6B shows a same slice, but with segmentations of iliac arteries (in particular, a right internal iliac 602a, a left internal iliac 602b, a right external iliac 604a, and a left external iliac 604b) overlaid. Comparing FIB. 6A with FIG. 6B, illustrates challenges associated with identifying pelvic lymph nodes and corresponding sub-regions, such as various iliac arteries and others described herein, within the pelvic region directly from (e.g., via segmentation of) a low dose CT image. As can be seen from FIG. 6A and FIG. 6B, these lymph node structures have limited contrast with respect to surrounding regions and are difficult to identify (compare, e.g., with the brighter pelvic bones visible in the images). Difficulties in performing direct segmentation of pelvic lymph nodes from anatomical images, such as a CT image is, accordingly, limit the ability of decision support systems to provide a user with anatomical context relating to pelvic lymph nodes and/or pre-select or pre-classify hotspots within functional images as belonging to—i.e., representing a potential cancerous lesion within—a particular pelvic lymph node. Systems and methods that overcome these obstacles and provide for identification of pelvic lymph sub-regions within functional images such as nuclear medicine images (e.g., PET images), in an automated or semi-automated fashion, offer advantages over previous techniques. In particular, among other things, they allow for more detailed automated analysis and reporting via decision support systems (e.g., via miTNM classification) and improved ability to finely distinguish, for example, between local tumors and grades of regional metastases, such those involving single or multiple lymph nodes.

In certain embodiments, approaches described herein address this challenge and provide capabilities for detailed lymph node classification of hotspots by combining automated segmentation of various bone and soft-tissue within an anatomical image, as described herein (e.g., in Section B, above) with an atlas image technique. In particular, in certain embodiments, systems and methods described herein create and/or utilize one or more pelvic atlas image(s) that include identifications—such as reference markers, segmented anatomical regions, and extended sub-volumes, etc., and register them with a segmentation map created via automated segmentation of a target CT image. In particular, by first performing anatomical segmentation of a target CT image to identify those bone and soft tissue regions that can be accurately segmented and then using them as landmarks with which to co-register one or more atlas image(s) with the anatomical segmentation map, approaches described herein provide for accurate identification of pelvic lymph sub-regions.

Figure 7:
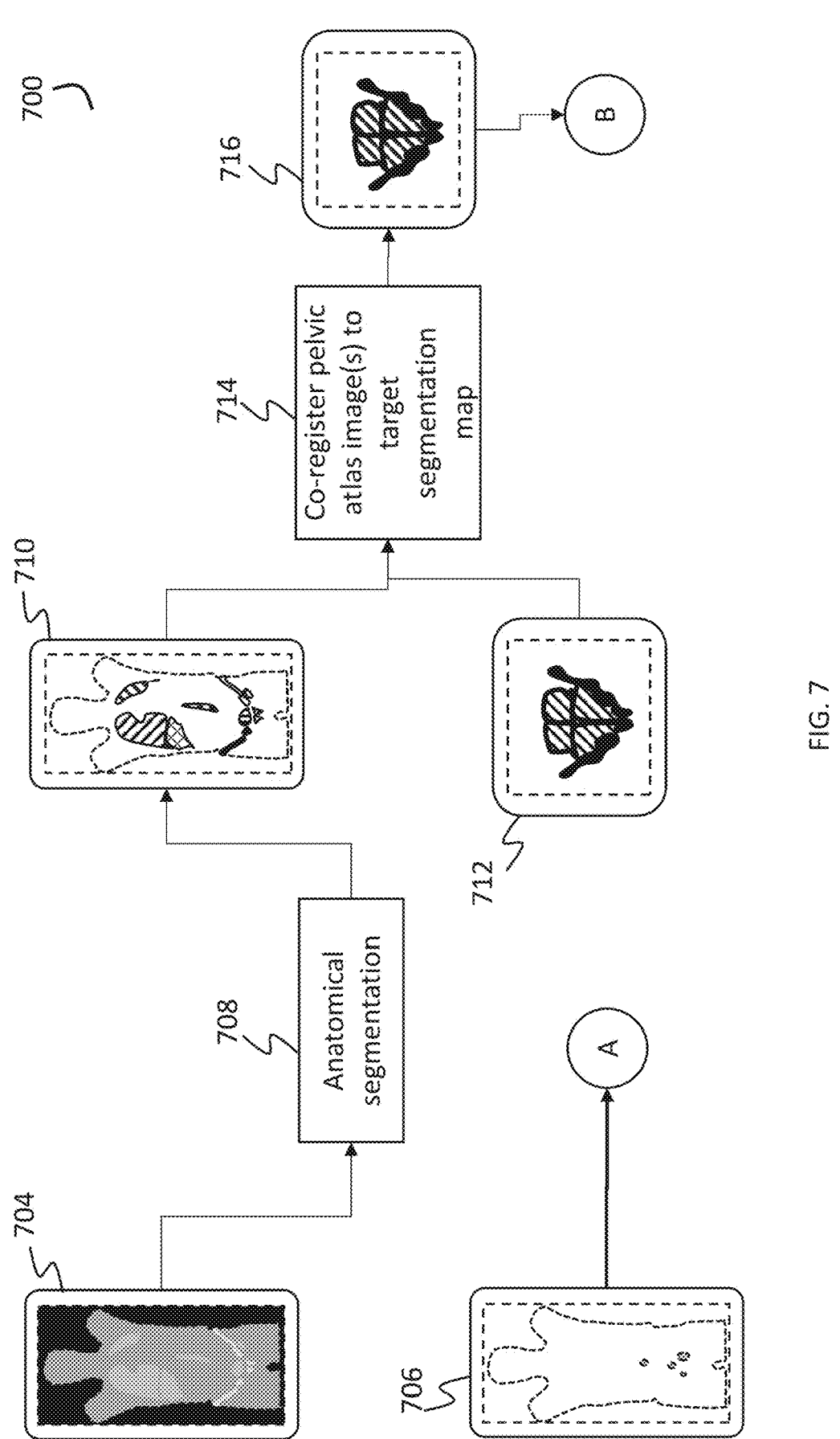
FIG. 7 is a diagram showing an example process for registering a pelvic atlas image with a target segmentation map, so as to align it with corresponding target anatomical and/or target functional images, according to an illustrative embodiment.

FIG. 7 shows an example process 700 for transforming pelvic atlas images in accordance with the technologies described herein in order to, for example, align them with an anatomical image and/or functional image of a composite image pair. In certain embodiments, an anatomical image 704, such as a CT image, and a functional image 706, such as a PET image, are received. As described herein, in certain embodiments the received functional 706 and anatomical 704 images are members of a composite image, such as a PET/CT image, for example obtained using a multimodal imaging instrument, and, accordingly, are aligned with each other. In certain embodiments, anatomical image 704 and functional image 706 are obtained separately and subsequently co-registered. The received anatomical image 704 may be a 3D anatomical image, such as a CT image. The received functional image 706 may be a 3D functional image, such as a PET or SPECT image.

Anatomical image 704 may be segmented 708 to create a segmentation map 710 that is aligned with anatomical image 704 and identifies regions corresponding to various anatomical structures of interest, such as particular organs, organ sub-regions, other soft-tissue, and bone. In certain embodiments, anatomical image 704 is a 3D anatomical image and segmentation map 710 is a 3D segmentation map. Segmentation 708 of a 3D anatomical image may be performed using any approaches described herein, for example in Section B, above. For example, in certain embodiments, segmentation 708 of anatomical image 704 is performed using one or more CNNs, via approaches such as those described in further detail in PCT publication WO/2020/144134, entitled "Systems and Methods for Platform Agnostic Whole Body Segmentation," and published Jul. 16, 2020, the content of which is incorporated herein by reference in its entirety.

In certain embodiments, segmentation map 710 includes one or more pelvic bone regions, such as left and right hip bone regions, a sacrum region, and a coccyx region. In certain embodiments, sacrum and coccyx regions are grouped together, such that one of the pelvic bone regions is a sacrum and coccyx region. As explained in further detail herein, pelvic bone regions of segmentation map 710 can be used as landmarks with which to transform one or more atlas image(s) 712 in order to co-register them 714 with segmentation map 710.

D.i. Pelvic Atlas Images

Figure 8:
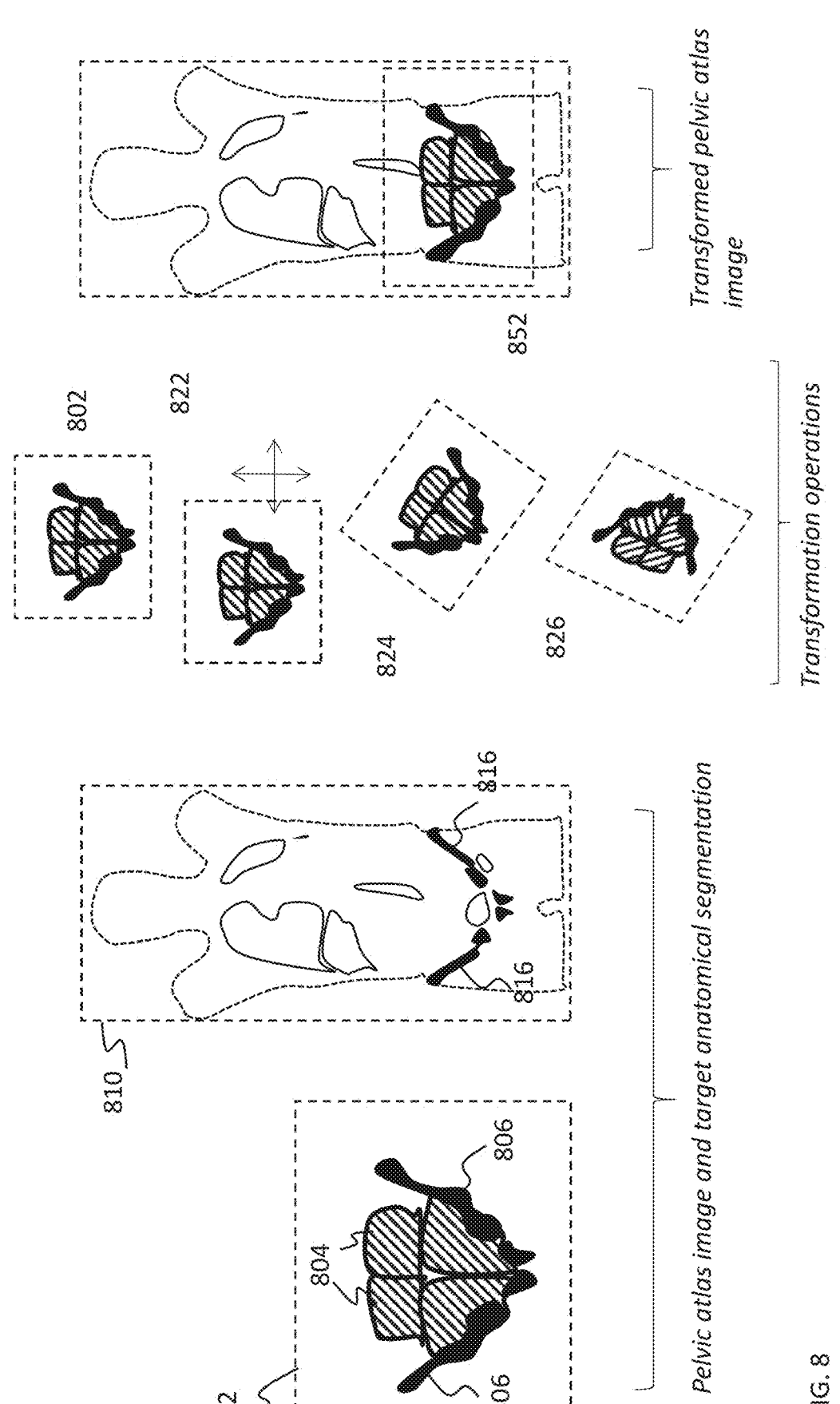
FIG. 8 is a schematic showing an example approach for transforming a pelvic atlas image to register it with a target anatomical segmentation.

In certain embodiments, one or more pelvic atlas images 712 are received and/or accessed. Turning to FIG. 8, in certain embodiments, a pelvic atlas image 802 is reference image that comprises (i) an identification of one or more pelvic lymph sub-regions 804 and (ii) an identification of one or more reference pelvic bone regions 806. The identification of pelvic lymph sub-regions 804 within atlas image 802 may be, or comprise, one or more regions of interest and/or reference markers that identify particular sub-volumes within pelvic atlas image 802 and/or sub-divide atlas image 802 into particular sub-volumes, each particular sub-volume associated with a particular pelvic lymph sub-region. In certain embodiments, the one or more pelvic atlas image(s) 712 is a/are 3D image(s)—i.e., a 3D pelvic atlas image(s).

Identifications of Pelvic Lymph Sub-Regions within Pelvic Atlas Images

A variety of approaches and implementations may be used to identify pelvic lymph sub-regions 804 within a pelvic atlas image 802.

Figures 9A, 9B, 9C, 9D:
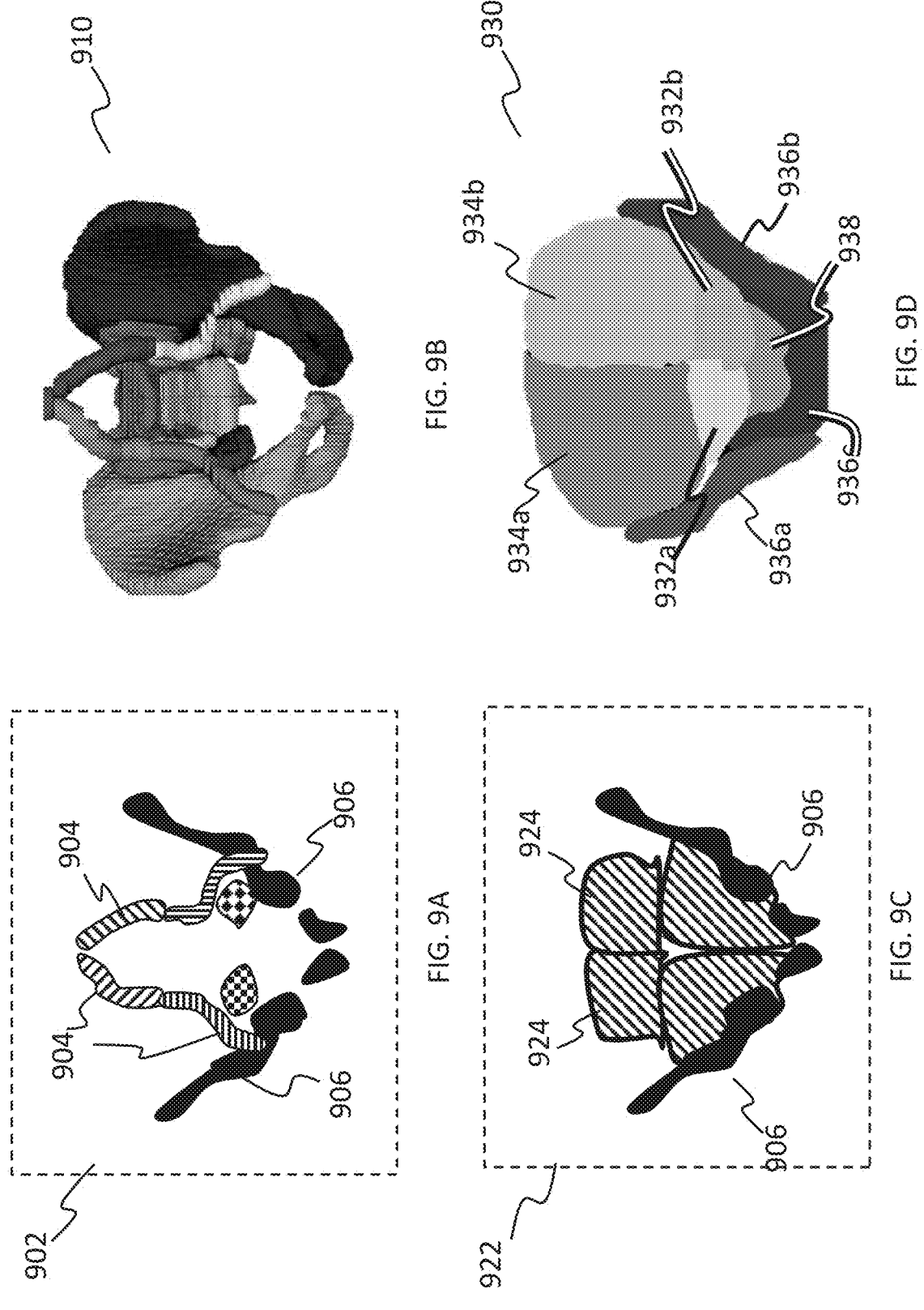
FIG. 9A is a schematic showing an example pelvic atlas image, according to an illustrative embodiment.
FIG. 9B is an example implementation of a pelvic atlas image according to the schematic shown in FIG. 9A, according to an illustrative embodiment.
FIG. 9C is a schematic showing another example pelvic atlas image, according to an illustrative embodiment.
FIG. 9D is an example implementation of a pelvic atlas image according to the schematic shown in FIG. 9C, according to an illustrative embodiment.

For example, turning to FIG. 9A, in certain embodiments, a pelvic atlas image 902 comprises (as an identification of one or more pelvic lymph sub-regions) a segmentation map 904 that identifies pelvic lymph node structures such as various iliac arteries, obturator nodes, and a presacral node. In certain embodiments, as shown in FIG. 9A, pelvic atlas image 902 may also comprise an identification of one or more reference pelvic bone regions 906. For example, pelvic atlas image 902 may comprise a second segmentation map that identifies the one or more reference pelvic bone regions. In certain embodiments, a single segmentation map may comprise identifications of pelvic lymph node structures 904 together with reference pelvic bone regions 906 in a manner that allows for differentiation between them. A pelvic atlas image such as pelvic atlas image 902 may, accordingly, be, or comprise, a segmentation map. FIG. 9B shows a corresponding example 3D atlas image that comprises a 3D segmentation map 910 that identifies pelvic lymph sub-regions [namely, iliac arteries, obturators (left and right), and a presacral region] along with pelvic reference bones. Accordingly, in certain embodiments, segmentations of anatomical structures—namely, one or more pelvic lymph nodes—are used directly as the identification of one or more pelvic lymph sub-regions within a pelvic atlas image, with each of the one or more pelvic lymph sub-regions corresponding to and identified by a segmented pelvic lymph node.

In certain embodiments, identifications of pelvic lymph sub-regions within pelvic atlas images such as those shown in FIGS. 9A and 9B may be created via segmentation of a reference image, such as a 3D anatomical image like a CT image. In certain embodiments, segmentation of a reference image in order to create a pelvic atlas image is performed manually and/or in a semi-automated fashion, for example based on input from an expert nuclear medicine physicist, a radiologist, a technician, and the like.

Turning to FIG. 9C, in certain embodiments, additionally or alternatively, a pelvic atlas image 922 identifies, e.g., as pelvic lymph sub-regions, one or more extended sub-volumes 924 each located about, and encompassing a local vicinity of, a corresponding particular anatomical structure, such as a particular pelvic lymph node. Such extended sub-volumes may be volumes that substantially encompass corresponding pelvic lymph nodes and their surrounding vicinity within a pelvic region. Each extended sub-region may correspond to a particular pelvic lymph node and substantially encompass a representation of that pelvic lymph node (e.g., within an anatomical image from which the pelvic atlas is derived). FIG. 9D shows an example implementation of one such atlas image 930 (the view shown in FIG. 9D is in a transverse plane, different from that in FIG. 9C, which illustrates an example pelvic atlas image in a coronal plane). Pelvic atlas image 930 of FIG. 9D comprises an identification of five pelvic lymph sub-regions, where each pelvic lymph sub-region is identified by an extended sub-volume corresponding to a local region substantially surrounding a particular corresponding pelvic lymph node. In particular, pelvic atlas image 930 comprises a right external iliac sub-volume 934a, a left external iliac sub-volume 934b, a right internal iliac sub-volume 932a, a left internal iliac sub-volume 932b, and presacral sub-volume 938. Pelvic atlas 930 also includes an identification of three reference pelvic bone regions, namely, a segmented right hip bone 936a, a segmented left hip bone 936b, and a sacrum and coccyx region 936c.

Figure 9F:
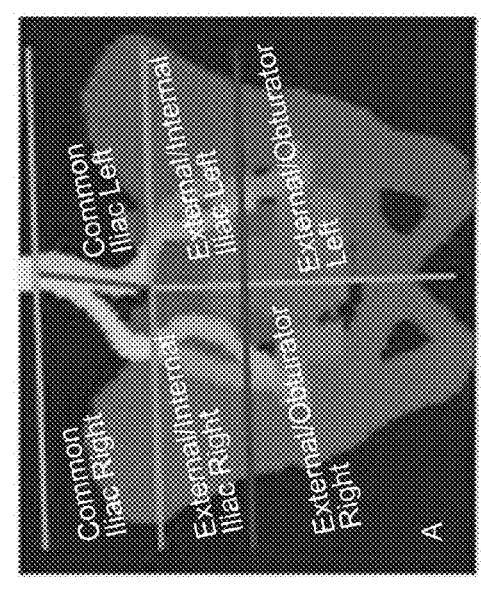
FIG. 9F is an example implementation of a pelvic atlas image according to the schematic shown in FIG. 9E, according to an illustrative embodiment.
Figure 9H:
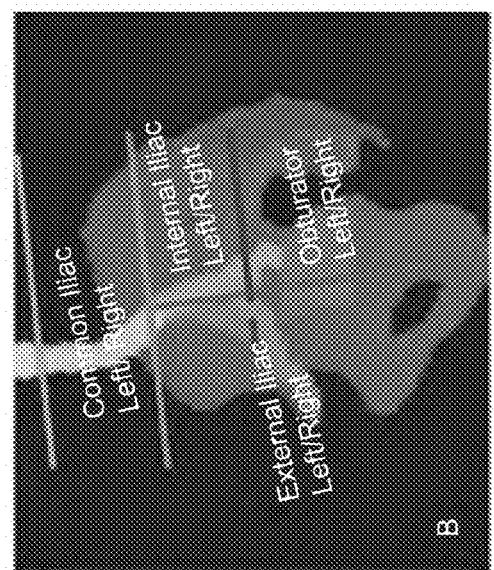
FIG. 9H is another view (in a sagittal plane) of the example implementation of a pelvic atlas image shown in FIG. 9F, according to an illustrative embodiment.
Figure 9E:
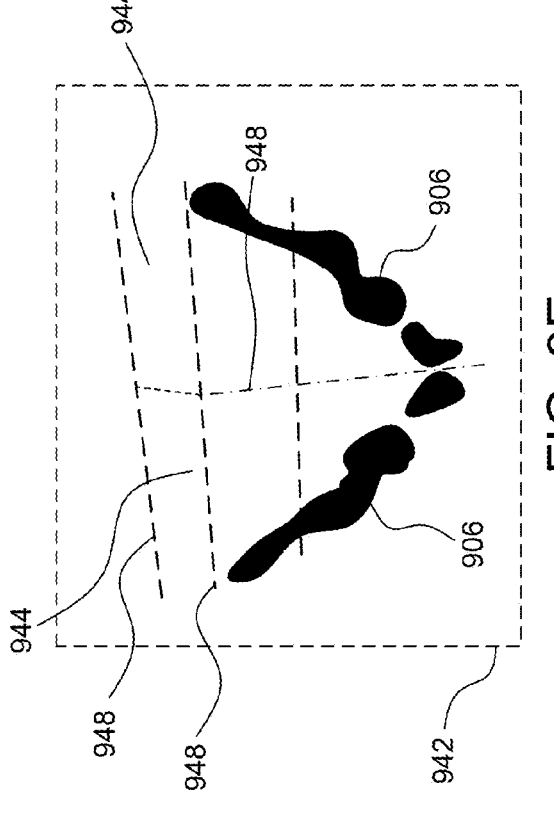
FIG. 9E is a schematic showing another example pelvic atlas image, according to an illustrative embodiment.

Turning to FIG. 9E, in certain embodiments, additionally or alternatively, identification of one or more pelvic lymph sub-regions within a pelvic atlas image 942 may be implemented via use of one or more reference markers 948. Such reference markers may, for example, be 2D surfaces, located within a 3D pelvic atlas image and which demark boundaries and/or portions thereof between two or more pelvic lymph sub-regions 944. Two dimensional surfaces used as reference markers in this manner may be planar surfaces or curved surfaces. Such surfaces may be infinite in one or more dimensions and/or finite in or more dimensions.

Figure 9G:
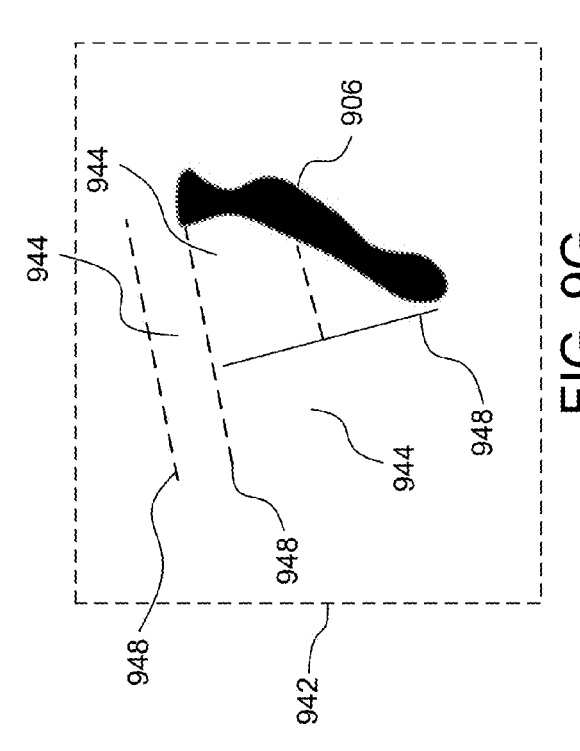
FIG. 9G is a schematic showing a different view (in a sagittal plane) of the schematic in FIG. 9E, according to an illustrative embodiment.

For example, FIG. 9E shows an example schematic (similar layout to those of FIGS. 9A and 9C) of a pelvic atlas image 942 that comprises several planar surfaces 948 that demark boundaries of pelvic lymph sub-regions 944. FIG. 9F shows an example implementation of one such pelvic atlas, with planar surfaces lying approximately parallel to a sagittal plane separating right and left hand portions of pelvic lymph sub-regions, and approximately axial planar surfaces separating regions such as a common iliac, external iliac, internal iliac, and obturator. FIG. 9G and FIG. 9H show a view of pelvic atlases shown in FIGS. 9E and 9F facing a sagittal plane, and show an additional planar marker located approximately parallel to a coronal plane and separating an external iliac sub-region, which lies to a front of the subject, from an internal iliac and obturator, both of which are toward a back of a subject.

Identifications of Reference Pelvic Bone Regions within Pelvic Atlas Images

In certain embodiments, a pelvic atlas image also includes an identification of one or more reference pelvic bone regions 906. Identification of a reference pelvic bone region within a pelvic atlas image may be a region obtained via segmentation of a particular pelvic bone, such as a left or right hip bone, a sacrum, a coccyx, or a group of two or more particular pelvic bones, such as a (e.g., combined) sacrum and coccyx region. Segmentations of particular pelvic bones and/or groups of pelvic bones may be represented via multiple separate segmentation masks and/or a segmentation map that distinguishably identifies particular pelvic bones and/or groups thereof. For example, as shown in FIG. 9D, pelvic atlas image 930 comprises a 3D segmentation map that includes a segmented right hip bone 936*a*, a segmented left hip bone 936*b*, and a sacrum and coccyx region 936*c*. FIG. 9B shows another example pelvic atlas 910, including segmented left and right hip (iliac) bones and a sacrum. In certain embodiments, an identification of one or more reference pelvic bones, such as a reference pelvic bone map (e.g., a segmentation map), may be obtained/created via automated segmentation of a reference CT image.

D.ii Registering Pelvic Atlas Images to Target Anatomical (e.g., CT) Images

Turning again to FIG. 7, in certain embodiments, in order to align pelvic atlas image 712 with, for example, a particular functional image and/or anatomical image of interest, pelvic atlas image 712 is transformed to co-register it with anatomical segmentation map 710. In certain embodiments, co-registering pelvic atlas image 712 to segmentation map 710 utilizes one or more identified reference pelvic bone regions within pelvic atlas image 712 together with corresponding pelvic bone regions in segmentation map 710.

Turning to FIG. 8, a registration transformation that aligns reference pelvic bone regions 806 of a pelvic atlas image 802 with corresponding pelvic bone regions 816 (shown in black) of a target segmentation map 810 can be determined and then applied to pelvic atlas image 802, including, and thereby transforming identifications of pelvic lymph sub-regions therein, to co-register pelvic atlas image 802 with target segmentation map 810. Accordingly, pelvic bones segmented within a target anatomical image, such as a CT image, and represented via a target segmentation map 810, can be used as landmarks in connection with matching reference pelvic bone segmentations 806 within a pelvic atlas image 802 to align and transform a pelvic atlas image 802 to a segmentation map 810 created from a particular anatomical image 704. In this manner, pelvic lymph sub-regions of a pelvic atlas image are aligned to an anatomical image 704 from which a target segmentation is created, and, by virtue thereof, also aligned to functional image 706, which is aligned to anatomical image 704.

In certain embodiments, co-registering pelvic atlas image 802 with a segmentation map 810 (e.g., created directly from a target CT image) may include transforming 820 pelvic atlas image 802 via one or more of operations including, but not limited to, translation 822, rigid registration 824, and an affine registration 826. Such transformations may be determined (e.g., computed) using pelvic bone regions 816 of segmentation map 810 and reference pelvic bone regions 806 within a pelvic atlas image 802. For example, in certain embodiments, a transformation (e.g., comprising one or more operations as described herein) may be computed using, for example, a version and/or portion of pelvic atlas image 802 comprising (e.g., only) reference pelvic bone regions 806.

In certain embodiments, all reference pelvic bone regions identified within a pelvic atlas image are used. In certain embodiments, a portion (e.g., a subset) of the reference pelvic bone regions of the pelvic atlas image are used together with a corresponding portion (e.g., subset) of the pelvic bone regions of the target segmentation map, for example omitting pelvic bones that may be abnormal, poorly segmented, or otherwise outliers that could undesirably influence registration.

For example, a transformation that co-registers pelvic atlas image 802 with segmentation map 810 may be determined as a set of one or more operations that optimize alignment between reference pelvic bone regions 806 of a pelvic atlas image 804 and corresponding pelvic bone regions 816 of a target segmentation map 810. Such transformation operations may be determined, for example, via one or more optimization routines, using one or more measures of alignment as performance metrics to maximize (or minimize, depending on e.g., the particular measure). For example, performance may be evaluated using Dice score, defined as:

$$\text{Dice }(A, B) = \frac{2|A \cap B|}{|A| + |B|}$$

which measures overlap between regions A, and B, in a normalized fashion, on a scale from 0 to 1. For example, A may be the one or more reference pelvic bone regions within a pelvic atlas image and B the corresponding pelvic bone regions within the target segmentation map.

Turning to FIGS. 7 and 8, once registration transformation is determined using pelvic bone landmarks as described herein, it can be applied to a whole pelvic atlas image—i.e., including the identifications of pelvic lymph sub-regions, thereby creating a transformed pelvic atlas image 716, 852 that is registered with the target segmentation map 710, 810. Since the target segmentation map 710, 810 is aligned with the anatomical image 704 from which it is created, this approach aligns pelvic lymph sub-regions with the anatomical image 704 and, in turn, functional image 706 aligned thereto.

Multi-Step Pelvic Atlas Registration

In certain embodiments, a pelvic atlas image may be registered with a segmentation map using one or more multi-step approaches.

For example, in certain embodiments, whereby multiple preliminary transformations, each of which aligns a particular subset of the one or more reference pelvic regions identified within the pelvic atlas to a corresponding subset of pelvic bone regions of the target segmentation map, may be determined and, then, combined to determine a final overall transformation.

For example, in certain embodiments, a two-step registration approach may be used to determine a transformation that co-registers a pelvic atlas image with a segmentation map. In certain embodiments, a first transformation that aligns (i) a first subset of the one or more reference pelvic regions identified within the pelvic atlas image to (ii) a corresponding first subset of the one or more pelvic bone regions of the segmentation map is determined, and a second transformation that aligns (i) a second subset of the one or more reference pelvic regions identified within the pelvic atlas image to (ii) a corresponding second subset of the one or more pelvic bone regions of the segmentation map is determined. In certain embodiments, the first subset of the one or more pelvic reference regions, as well as the corresponding first subset of the one or more pelvic bone regions of the segmentation map, represent pelvic bones and/or groups thereof on a left side of a subject. In certain embodiments, the second subset of the one or more pelvic reference regions, as well as the corresponding second subset of the one or more pelvic bone regions of the segmentation map, represent pelvic bones and/or groups thereof on a right side of the subject. Accordingly, a first transformation may be optimized to align a left portion of a pelvic atlas image with a corresponding left-hand portion of a segmentation map and a second transformations may be optimized to align a right-hand portion of a pelvic atlas image with a corresponding right-hand portions of the target segmentation map, respectively.

In certain embodiments, a final overall transformation is determined based on the multiple preliminary transformations, for example a first and second transformations that align left and right hand portions of a pelvic atlas image with a target segmentation map. A final, overall, transformation may be determined, for example, as a weighted average of two or more (e.g., a subset of or all of) preliminary transformations, such as a weighted average of a first and second transformation. In certain embodiments, a voxel-dependent weighting factor is used, where each voxel is transformed according to a weighted average of two or more preliminary transforms, each preliminary transform's respective weight varying from voxel to voxel. In certain embodiments, a weight for a particular transform at a particular voxel is determined based on a distance of that particular voxel from the particular subset of pelvic reference regions that were used to compute the particular transform. Once determined, a final overall transformation determined in this manner may be applied to register the pelvic atlas to the segmentation map.

Additionally or alternatively, in certain embodiments, multiple registration transformations may be determined, and performed, in sequence. For example, a first, coarse registration transformation is determined, then applied (e.g., to create a first transformed pelvic atlas image), followed by a second, fine, registration transformation that further optimizes alignment. In certain embodiments, both the first (e.g., coarse) and second (e.g., fine) registration transformations are determined using the same one or more reference pelvic bone regions within the pelvic atlas image (together with their corresponding pelvic bone regions in the target segmentation map) (e.g., the entire set of one or more reference pelvic bone regions; e.g., a same subset of the one or more reference pelvic bone regions). In certain embodiments, the first registration transformation is determined using a first subset of the one or more reference pelvic bone regions, together with a corresponding subset of the one or more pelvic bone regions of a target segmentation map, (e.g., left and right hip bones and a sacrum and coccyx region) and the second registration transformation is determined using a second subset of the one or more reference pelvic bone regions together with a corresponding second subset of the one or more pelvic bone regions of the segmentation map (e.g., left and right hip bones).

In certain embodiments, the one or more reference pelvic bone regions of the pelvic atlas image are used, together with the corresponding one or more pelvic bone regions of a target segmentation map to determine a first transformation that performs a coarse co-registration of the pelvic atlas image to the target segmentation map. In certain embodiments, the pelvic atlas image may comprise one or more, additional, secondary reference tissue regions that correspond (i.e., represent a same one or more physical anatomical structures) to one or more (e.g., automatically segmented) secondary tissue regions in the target segmentation map. In certain embodiments, the one or more secondary tissue regions comprise soft-tissue regions, such as certain organs or organ sub-regions (e.g., a urinary bladder, a ureter, a rectum, a prostate, a left/right gluteus maximus, etc.). In certain embodiments, the second (e.g., fine) registration transformation is determined using the one or more secondary reference tissue regions and the corresponding secondary tissue regions in the target segmentation map.

Additionally or alternatively, in certain embodiments, the first (e.g., coarse) registration transformation comprises (e.g., is restricted to) a first set of transformation operations (e.g., a first combination of operations, such as one or more of translation, rigid registration, affine transformation) and the second (e.g., fine) registration transformation comprises (e.g., is restricted to) a second set of transformation operations (e.g., a first combination of operations, such as one or more of translation, rigid registration, affine transformation). In certain embodiments, the first registration transformation is restricted to translation and rigid registration operations and the second registration transformation is or comprises affine transformation. In certain embodiments, the second registration transformation is itself determined using a multi-step approach, such as two-step approach that determines two co-registration transformations based on left and then right hip bone regions, individually, and then combines them into a final overall transformation using a distance dependent voxel weighting, as described herein. In this manner, for example, the second registration is non-rigid.

Additionally or alternatively, in certain embodiments, a first, e.g., coarse, registration transformation is determined using a first resolution and a second, e.g., fine, registration transformation is determined using a second resolution.

Additionally or alternatively, in certain embodiments, a first, e.g., coarse, registration transformation is determined for a plurality of initial, prospective pelvic atlas images to create a plurality of transformed prospective pelvic atlas images from which a 'best-fit' transformed pelvic atlas image is selected. In certain embodiments, the 'best-fit' transformed pelvic atlas image is selected from the plurality of transformed prospective pelvic atlas images based on one or more metrics that evaluate overlap between at least a portion of (e.g., up to all) the one or more reference pelvic bone regions of the pelvic atlas image and a corresponding portion of the one or more pelvic bone regions of the target segmentation map. In certain embodiments, a second, e.g., fine, registration transformation is then determined for the selected 'best-fit' transformed pelvic atlas image, to further refine alignment of the 'best-fit' pelvic atlas image to the target segmentation map. A final, overall transformation may be determined as the combination (e.g., in sequence) of the first transformation followed by the second transformation, and applied to the entire 'best-fit' pelvic atlas image to create a final transformed pelvic atlas image.

In certain embodiments, portions of a first, initial registration may be combined with a second, fine registration, for example to create a combined transformed pelvic atlas. For example, in certain embodiments a first, coarse registration may be used to transform portions of a pelvic atlas image, e.g., corresponding to a presacral region, and a second, fine, registration may be used to transform other portions of the pelvic atlas image.

Multiple Atlas Image Registration

Turning to FIG. 7 in certain embodiments, step 714 is repeated for multiple pelvic atlas images—that is, multiple pelvic atlas images 712 may be co-registered with segmentation map 710. In certain embodiments, multiple pelvic atlases may be used, for example to capture a variety of different body sizes and types for subjects. For example, obese patients may have more fatty tissue and, accordingly, be best analyzed using a different pelvic atlas than, e.g., a pelvic atlas used for a patient of average or below average body-mass index.

In certain embodiments, multiple prospective pelvic atlas images are transformed and evaluated using a performance metric that gauges registration performance, such as a Dice score as described above. In certain embodiments, other performance metrics, such as similarity measures (e.g., measuring similarity between sets of voxels in the two images), including, but not limited, to Tversky indices (e.g., Dice score is a Tversky index) may be used. In certain embodiments, one or more highest performing pelvic atlases are selected and transformed versions thereof used for downstream processing. In certain embodiments, other criteria (for example, not necessarily based on alignment of pelvic bones following the registration transformation) may be used.

Accordingly, in this manner, a particular 'best-fit' pelvic atlas may be selected out of a set of one or more (e.g., pre-defined) prospective pelvic atlas images.

E. Classifying Hotspots Accordingly to Local Pelvic Lymph

Figure 10:
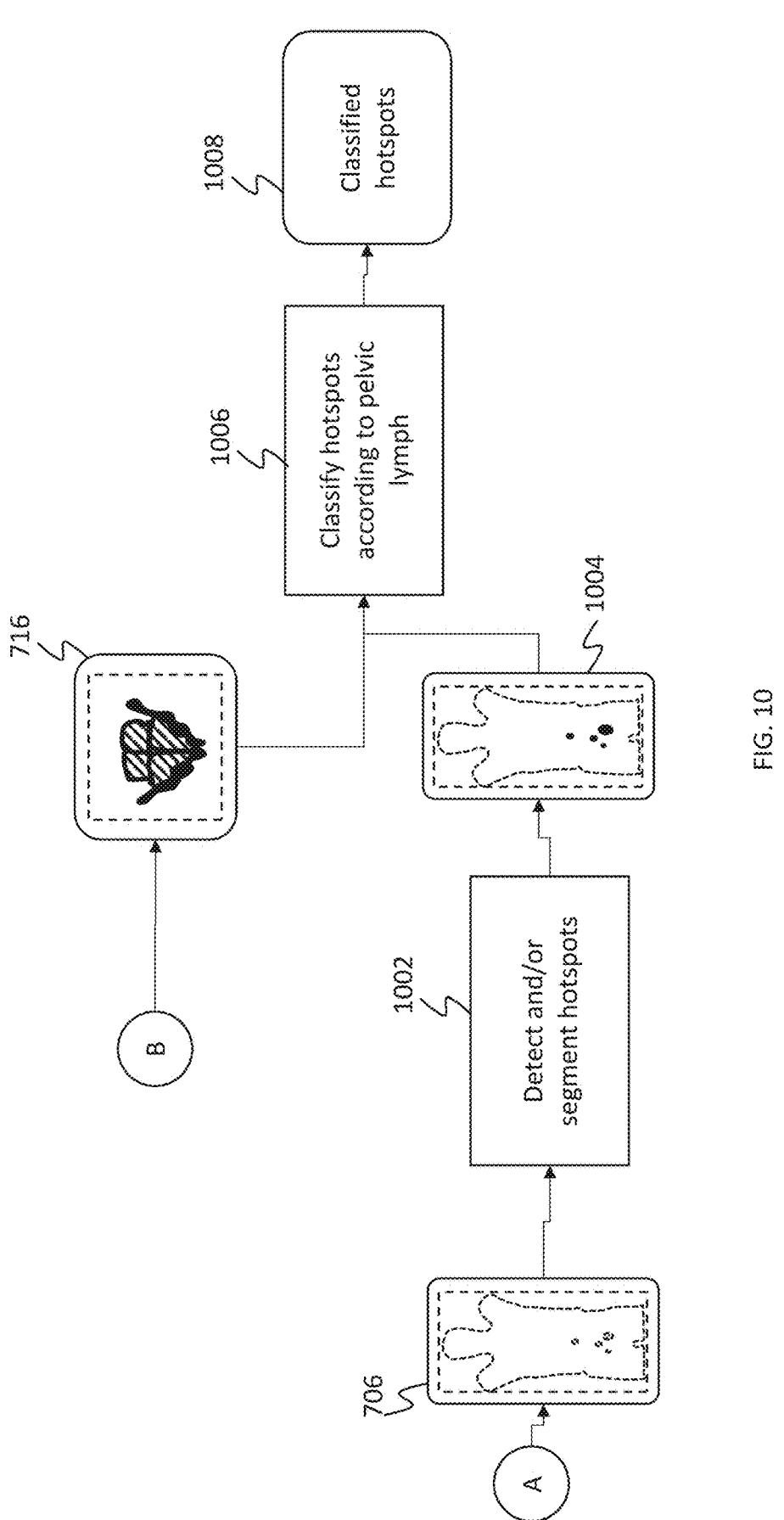
FIG. 10 is a diagram showing an example process for classifying hotspots according to pelvic lymph sub-regions, according to an illustrative embodiment.

Turning to FIG. 10, in certain embodiments, a transformed pelvic atlas image 716, having been co-registered to segmentation map 710 can be used to identify regions and boundaries (e.g., 3D regions and boundaries) within anatomical image 702 from which segmentation map 710 was created and/or a functional image 704 aligned to anatomical image 704. In certain embodiments, this approach may be used to classify hotspots within a functional image (e.g., a nuclear medicine image) that represent potential lesions, according to their location with respect to one or more pelvic lymph sub-regions.

For example, as described herein, in order to evaluate radiopharmaceutical uptake and characterize lesions within a subject, 3D anatomical images, such as CT images, may be acquired along with a corresponding 3D functional image, such as a PET or SPECT image. This approach allows anatomical/structural information of a, e.g., CT image to be correlated with the functional information of the corresponding PET or SPECT image. Anatomical and functional images may be acquired using a single multimodal imaging system (e.g., a PET/CT system; e.g., a SPECT/CT system), such that the subject is a substantially fixed position while scans to acquire the anatomical and functional images are performed. In this manner, the two (anatomical and functional) images are aligned, and volumes identified within the anatomical image as corresponding to specific organs and/or tissue regions can be used to identify those voxels the functional image that correspond to those same specific organs/and or tissue regions. Additionally or alternatively, in certain embodiments, an anatomical and a functional image may be acquired separately, and subsequently co-registered to each other to align them.

A functional image 706 may include one or more hotspots corresponding to localized regions of elevated intensity (e.g., with respect to their surroundings) that represent potential cancerous lesions within the subject. In certain embodiments, hotspots within functional image 706 may be detected and/or segmented 1002 to create a hotspot map 1004 that identifies (e.g., distinguishably) regions within functional image 706 corresponding to hotspots. Hotspots may be detected, segmented, and classified using analytical techniques (e.g., thresholding), machine learning (e.g., neural network-based segmentation and/or classification) and combinations thereof. Examples of various techniques for identifying and classifying hotspots, and their use in, for example, evaluating disease status, progression, and response to treatment are explained herein, for example at Section C, above, and described in further detail in PCT publication WO/2020/144134, entitled "Systems and Methods for Platform Agnostic Whole Body Segmentation," and published Jul. 16, 2020, U.S. Patent Publication No. US 2021/0334974 A1, entitled "Systems and Methods for Deep-Learning-Based Segmentation of Composite Images," and published Oct. 28, 2021, and PCT publication WO/2022/008374, entitled "Systems and Methods for Artificial Intelligence-Based Image Analysis for Detection and Characterization of Lesions," and published Jan. 13, 2022, the contents of each of which are incorporated by reference herein in their entirety.

In certain embodiments, hotspots located within a pelvic region can be classified according to their location in relation to one or more of the pelvic lymph sub-regions of a transformed pelvic atlas image 716 which, e.g., by virtue of being co-registered with a target segmentation map 710, is also co-aligned with functional image 706. That is, since anatomical image 704 and functional image 706 are aligned, co-registering pelvic atlas image 716 with segmentation map (which is created via segmentation of, and, accordingly, aligned with, anatomical image 704) aligns pelvic lymph sub-regions of pelvic atlas image 716 with functional image 706, such that they can be overlaid on functional image 706 and/or used to identify corresponding volumes within functional image 706. For example, in certain embodiments, a particular hotspot may be identified as belonging to—that is, representing a potential lesion located within—a particular one of the one or more pelvic lymph sub-regions identified in the pelvic atlas image. Classification of hotspots in this manner may be accomplished using, for example, hotspot map 1004 together with transformed pelvic atlas image 716. Classifying hotspots according to their pelvic lymph sub-region may be used to create a set of classified hotspots 1008, wherein each hotspot (e.g., of hotspot map 1004) is labeled according to a particular pelvic lymph node that it is determined to belong to (i.e., represent a lesion located within).

Figure 11:
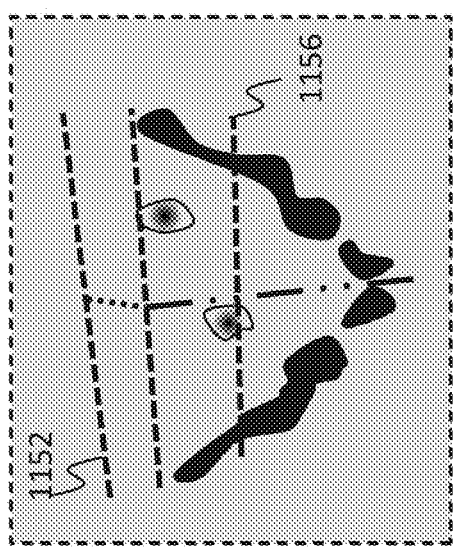
FIG. 11 is an example schematic showing classification of hotspots via a pelvic atlas image aligned to a PET image, according to an illustrative embodiment.
Figure 11:
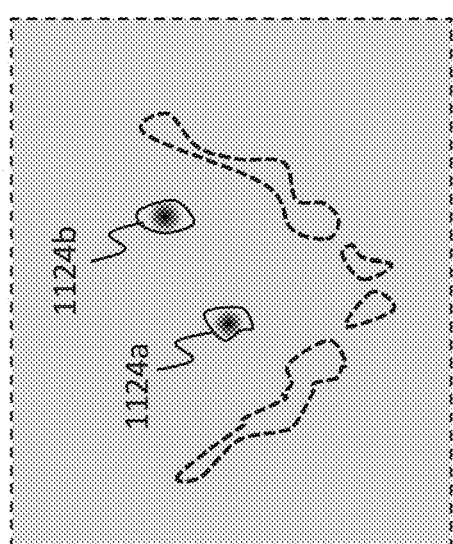
Figure 11:
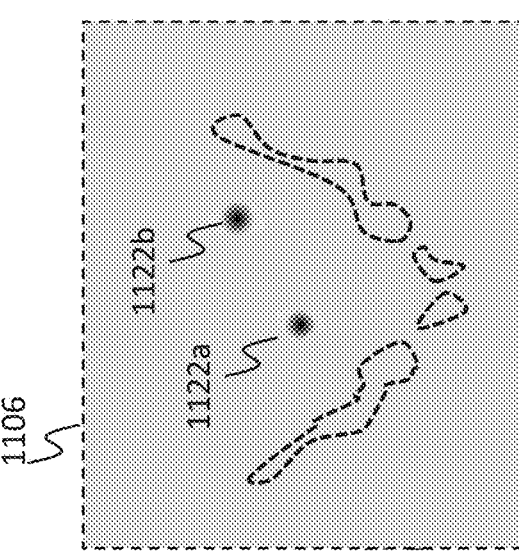

Turning to FIG. 11, in certain embodiments, such a classification may be based on a determination that a particular hotspot falls within a particular pelvic lymph sub-region of an aligned pelvic atlas image, or overlaps (e.g., most) with a particular pelvic lymph sub-region. As illustrated in FIG. 11, hotspots 1122*a*, 1122*b* present in a 3D functional image 1106, such as a PET image may be detected and segmented such that their boundaries are identified (e.g., via a hotspot map). Hotspots may then be classified according to a particular pelvic lymph sub-region based, for example, of a measure of proximity and/or overlap of a hotspot volume with a particular pelvic lymph sub-region, e.g., as identified by a segmented lymph node region, extended sub-volume, and/or planar reference marker 1152, 1156.

In this manner, in certain embodiments, each of one or more individual hotspots located within a pelvic region may be further classified as belonging to, and therefore representing a potential lesion within, a particular pelvic lymph node region, such as a left or right common iliac, a left or right external iliac, a left or right internal iliac, a left or right obturator, and a presacral node.

In certain embodiments, an additional category may be used for hotspots that are not, for example, sufficiently overlapping with and/or in sufficient proximity to a particular pelvic lymph sub-region. Such hotspots may be, for example, classified as "other pelvic," (e.g., a catch all category), identified as not belonging to a pelvic lymph node, and/or flagged for further review, for example by a radiologist.

In certain embodiments, approaches described in this section are applied to a particular subset of hotspots within a hotspot map generated, e.g., using one or more machine learning modules. For example, as described in Section C, above, pelvic lymph classification approaches described herein may be applied to a particular category of hotspots of a multi-class hotspot map, such as a subset of hotspots having been labeled as corresponding to potential lymph lesions (e.g., and not applied to those hotspots labeled as bone and/or prostate).

In certain embodiments, based on classifications of individual hotspots as belonging to pelvic lymph regions, an overall classification of a patient's regional nodes can be determined (e.g., automatically), for example according to the miTNM classification scheme described in Eiber et al., J. Nucl. Med. 2018; 59:469-478, as shown in Table 1, below. In certain embodiments, hotspots are initially classified as local tumor (e.g., labeled "T"), a distant metastases (e.g., outside the pelvic region) (e.g., labeled "M" type) or a regional, pelvic lymph node metastases (e.g., labeled "N"). In certain embodiments, hotspots labeled "N" are further classified according to the particular pelvic lymph sub-region (e.g., lymph node) they are located within—e.g., each N-type hotspot labeled as belonging to one or more of a left internal iliac, a right internal iliac, a left external iliac, a right external iliac, a left common iliac, a right common iliac, a left obturator, a right obturator and a presacral node.

TABLE 1

Example classifications of regional nodes according to a
miTNM-based framework

| Classification | Description/Criteria |
|---|---|
| miN0 | No positive regional lymph nodes (e.g., no hotspots classified as belonging to a pelvic lymph sub-region) |
| miN1a | Single lymph node region with metastases (e.g., one or more hotspots all classified as belonging to one particular pelvic lymph sub-region) |
| miN1b | Multiple (e.g., two or more) lymph node regions with metastases (e.g., two or more hotspots classified as belonging to two or more different pelvic lymph sub-regions) |

F. Example Pelvic Atlas Registration and Pelvic Lymph Classification Approaches

Presented herein are three example implementations of pelvic atlas images and approaches for registering them with target segmentations in order to classify hotspots of (co-aligned), corresponding PET images according to local pelvic lymph sub-region.

Example 1

In this example, a pelvic atlas image that identifies pelvic lymph sub-regions as extended volumes is created, registered with a target segmentation, and overlaid on a corresponding PET image in order to classify hotspots.

Figure 12C:
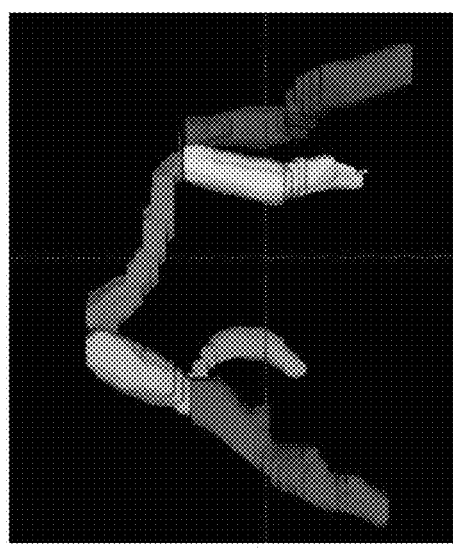
FIG. 12C is another view of the 3D rendering shown in FIG. 12B, according to an illustrative embodiment.
Figure 12B:
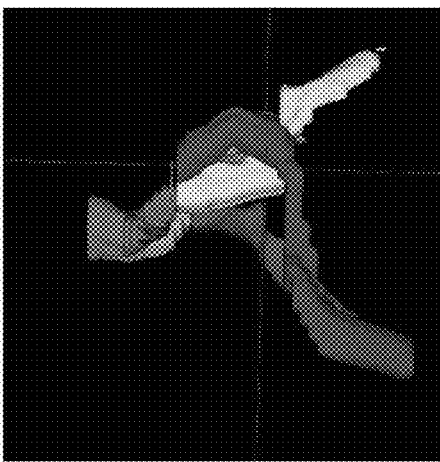
FIG. 12B is a 3D rendering of a segmentation map identifying iliac arteries, according to an illustrative embodiment.
Figure 12A:
FIG. 12A is a slice of a CT image with segmentations of iliac arteries overlaid, according to an illustrative embodiment.

FIG. 12A shows a slice of a 3D CT image with segmented iliac arteries overlaid. Three dimensional views of the segmented iliac arteries, created via manual annotations of a nuclear medicine physicist, are shown in FIGS. 12B and 12C.

Figure 13:
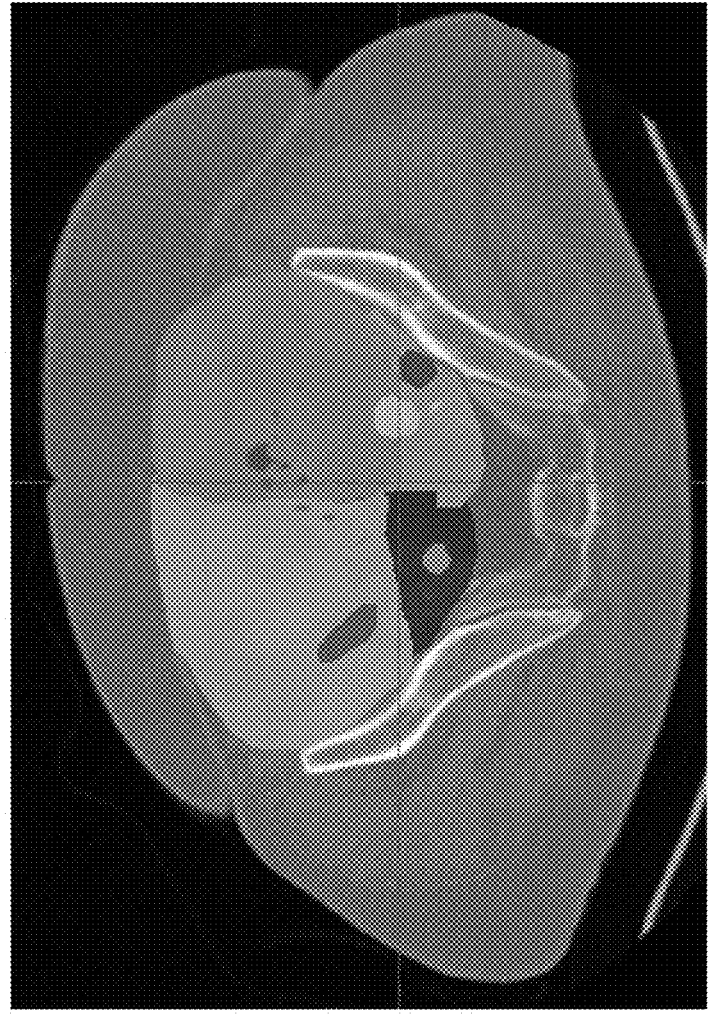
FIG. 13 is a CT image slice overlaid with iliac artery segmentations and corresponding extended sub-volumes that identify local regions about each iliac artery, according to an illustrative embodiment.

Turning to FIG. 13, to create a pelvic atlas image, regions surrounding the segmented iliac arteries are extended to create corresponding extended sub-volumes about each segmented structure. As shown in FIG. 13, for each segmented structure (e.g., iliac artery), the corresponding extended sub-volume may substantially, but need not entirely, encompass the segmented structure.

Figure 14B:
FIG. 14B is a CT image slice overlaid with a segmented pelvic bone region, according to an illustrative embodiment.
Figure 14A:
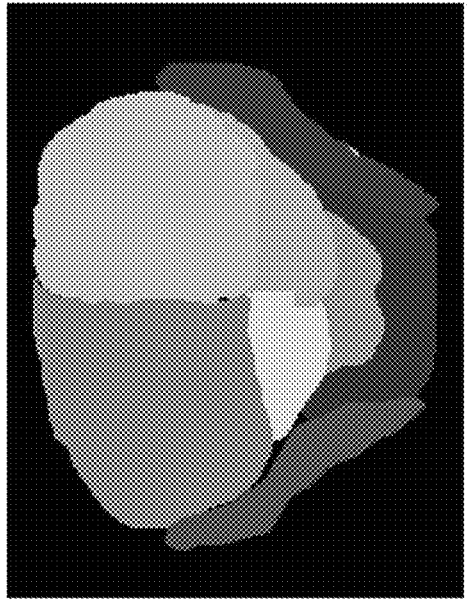
FIG. 14A is an image of a pelvic atlas image, according to an illustrative embodiment.

FIG. 14A shows a resultant pelvic atlas image, including both the identifications of pelvic lymph sub-regions as well as segmentations of pelvic bones, for example left and right hip bones, a sacrum and coccyx, which are to be used as landmarks for registering the pelvic atlas image to a target segmentation map. The particular target segmentation map 1452 is shown in FIG. 14B, overlaid on the CT image 1454 from which it was created.

Figures 15A, 15B:
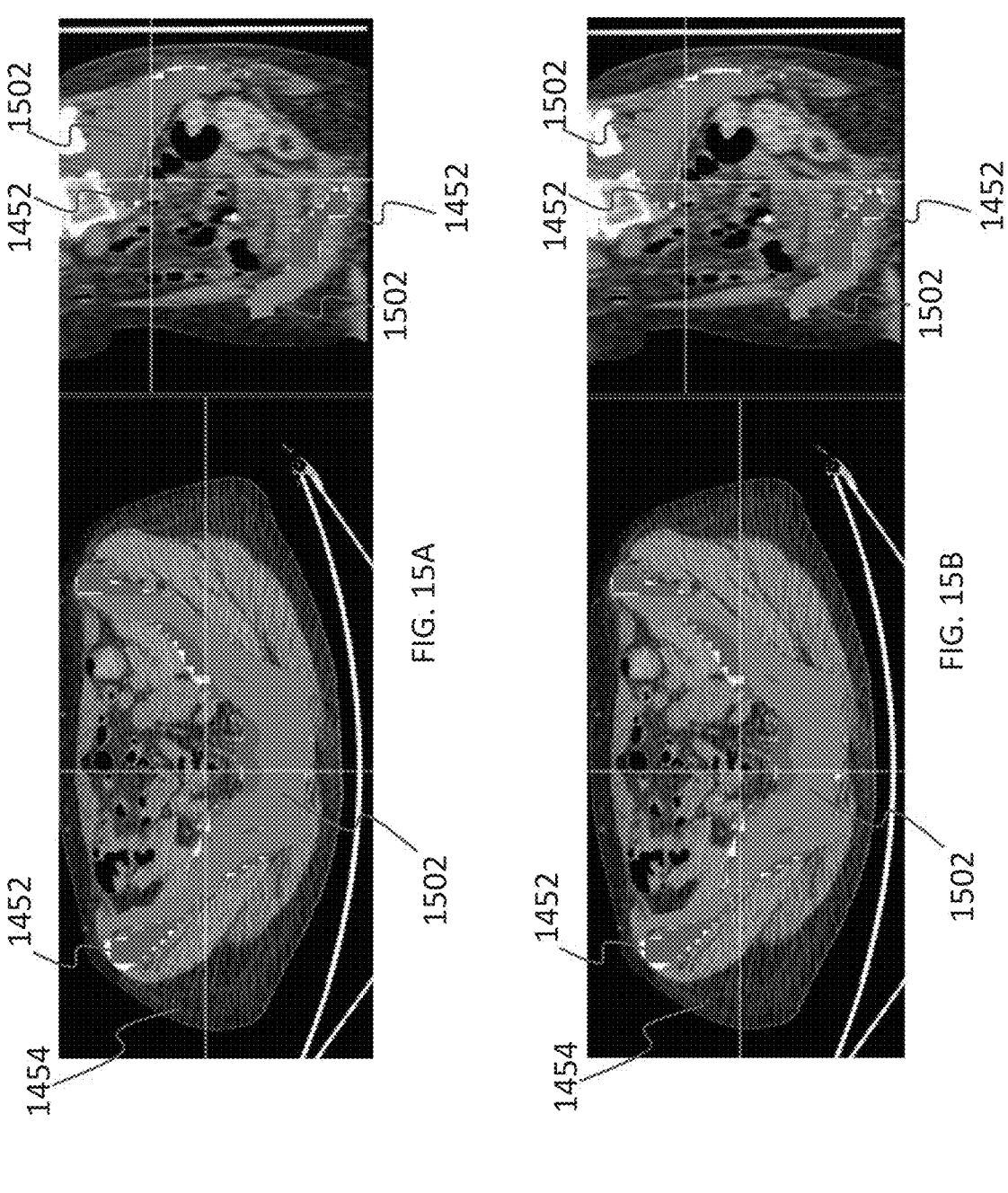
FIG. 15A is a CT image slice overlaid with a segmented pelvic bone region generated via automated segmentation of the CT image, together with a reference pelvic bone region of a pelvic atlas image having been aligned thereto via a translation operation, according to an illustrative embodiment.
FIG. 15B is a CT image slice overlaid with a segmented pelvic bone region generated via automated segmentation of the CT image, together with a reference pelvic bone region of a pelvic atlas image having been aligned thereto via a rigid registration operation, according to an illustrative embodiment.
Figure 15C:
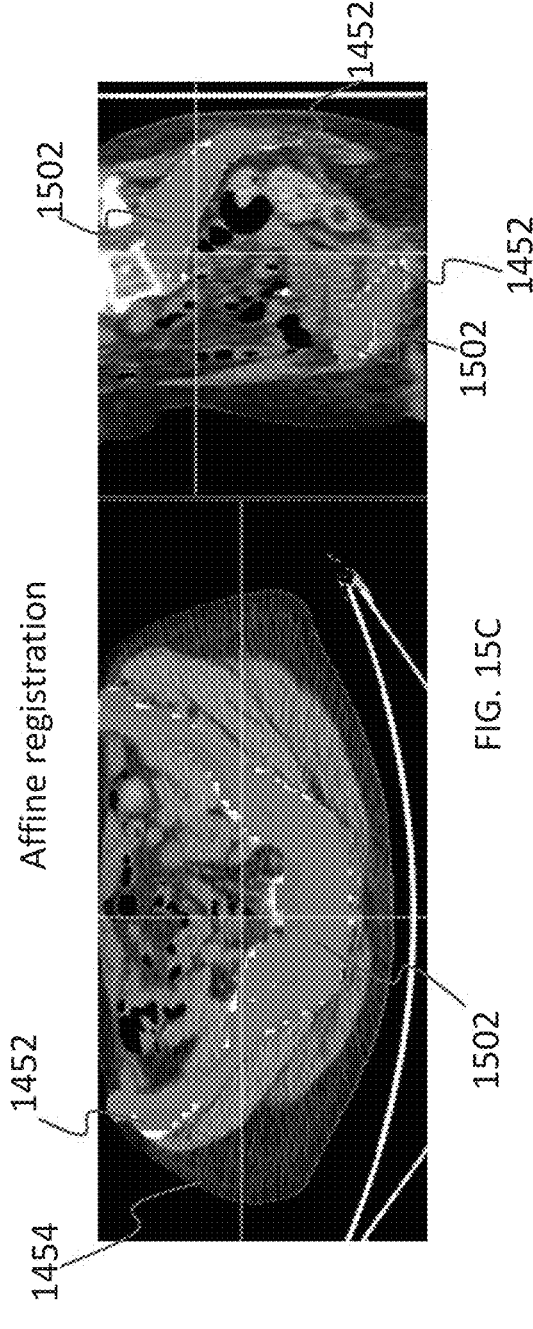
FIG. 15C is a CT image slice overlaid with a segmented pelvic bone region generated via automated segmentation of the CT image, together with a reference pelvic bone region of a pelvic atlas image having been aligned thereto via an affine transformation operation, according to an illustrative embodiment.

FIGS. 15A-C show results of various image transformations used to register the pelvic atlas image to the target segmentation map. Each of FIGS. 15A-C shows the reference pelvic bone region 1502 from the atlas image (following transformation), overlaid on the target segmentation map 1452 and CT image 1454. FIG. 15A shows results of a translation operation, FIG. 15B shows results of a rigid registration operation, and FIG. 15C shows results of an affine transformation.

Figure 16:
FIG. 16 is a CT image slice overlaid with a pelvic atlas image, according to an illustrative embodiment.

Following determining the registration transformation using the pelvic bones, e.g., as shown in FIGS. 15A-C, the transformation was applied to the entire pelvic atlas image (including pelvic lymph sub-regions). The resultant transformed pelvic atlas image was thereby aligned to the target CT image and, in turn, the PET corresponding PET image. FIG. 16 shows the transformed pelvic atlas image overlaid on the target CT image.

Figure 17:
FIG. 17 is a CT image slice overlaid with a pelvic atlas image and a PET image, according to an illustrative embodiment.

FIG. 17 shows the transformed pelvic atlas overlaid on a fusion of the target CT and the target PET image, showing two hotspots in relation to the aligned pelvic lymph sub-regions of the transformed atlas image. Based on the overlap between the hotspots and the pelvic lymph sub-regions, an internal (right hand) iliac was suggested as a location for the smaller hotspots and an external (left hand) iliac was suggested as a location for the larger hotspot.

Figure 18:
FIG. 18 is a CT image slice overlaid with a pelvic atlas image and a PET image, according to an illustrative embodiment.

FIG. 18 illustrates an observed effect showing that certain atlas images may be, for example, better suited to patients of different body weights. For example, as shown in FIG. 18, a portion 1802 of the pelvic atlas image appears to extend beyond the stomach of the subject imaged in the CT image, indicating that, for example, an approach whereby multiple versions of pelvic atlas images (e.g., based on differing patient body weights or BMIs) might offer improved performance.

Example 2

This example demonstrates an embodiment whereby a pelvic atlas that identifies pelvic-lymph sub-regions using segmentations of particular lymph node structures is used. This example also demonstrates use of a multi-step registration approach.

Figure 19:
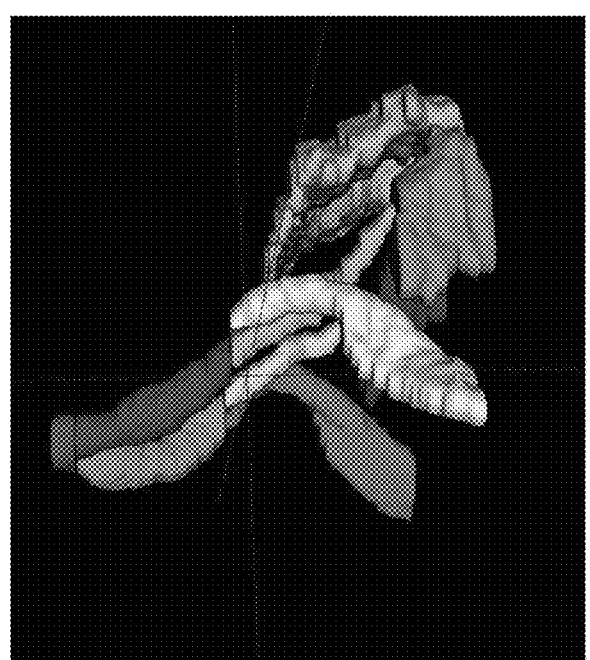
FIG. 19 is a 3D rendering of a 3D segmentation map identifying certain pelvic lymph node structures, according to an illustrative embodiment.
Figure 20:
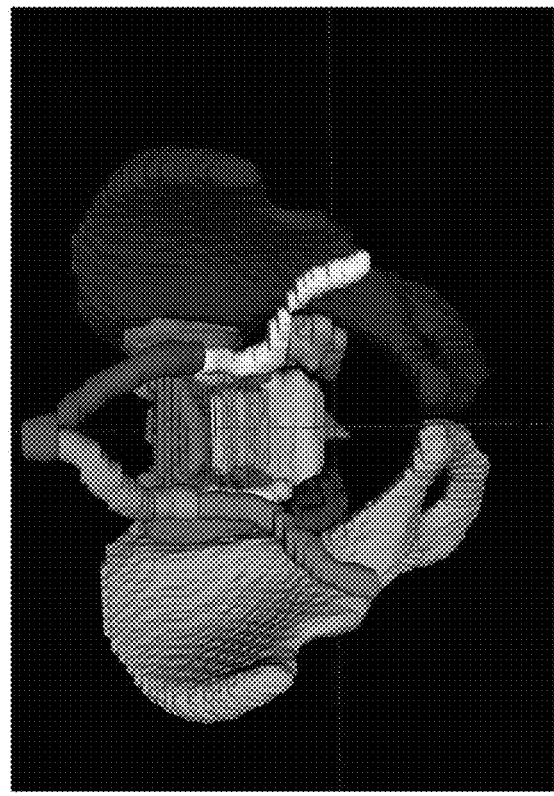
FIG. 20 is two views of a 3D rendering of 3D segmentation map identifying certain pelvic lymph node structures and pelvic bones, according to an illustrative embodiment.
Figure 20:
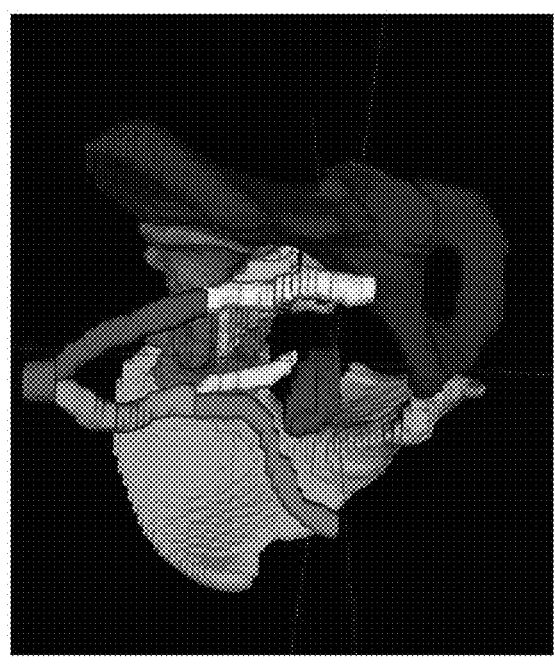
Figure 21A:
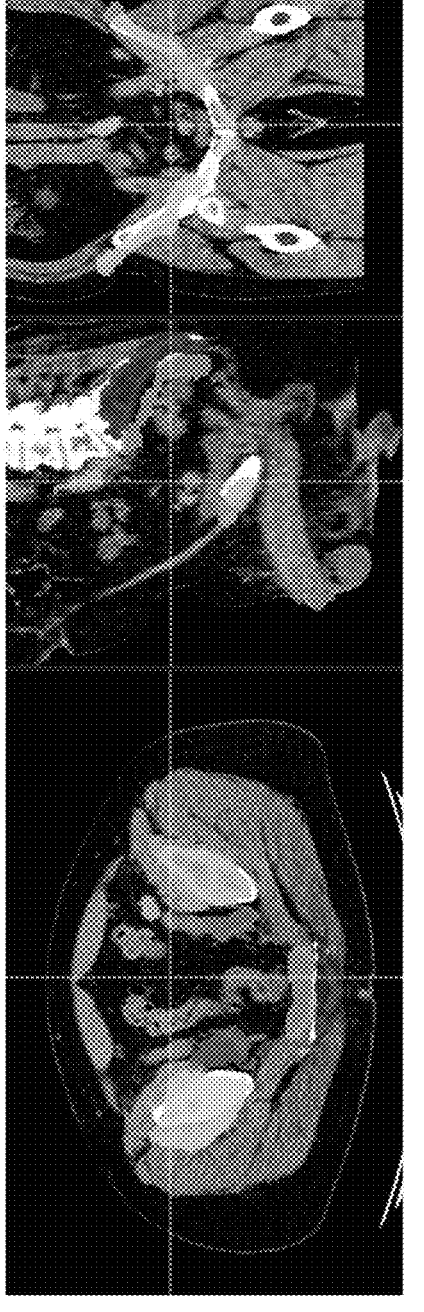
FIG. 21A is a set of three views of a CT image, overlaid with a pelvic atlas image, according to an illustrative embodiment.
Figure 21B:
FIG. 21B is a set of three views of a CT image, overlaid with a pelvic atlas image, according to an illustrative embodiment.
Figure 21C:
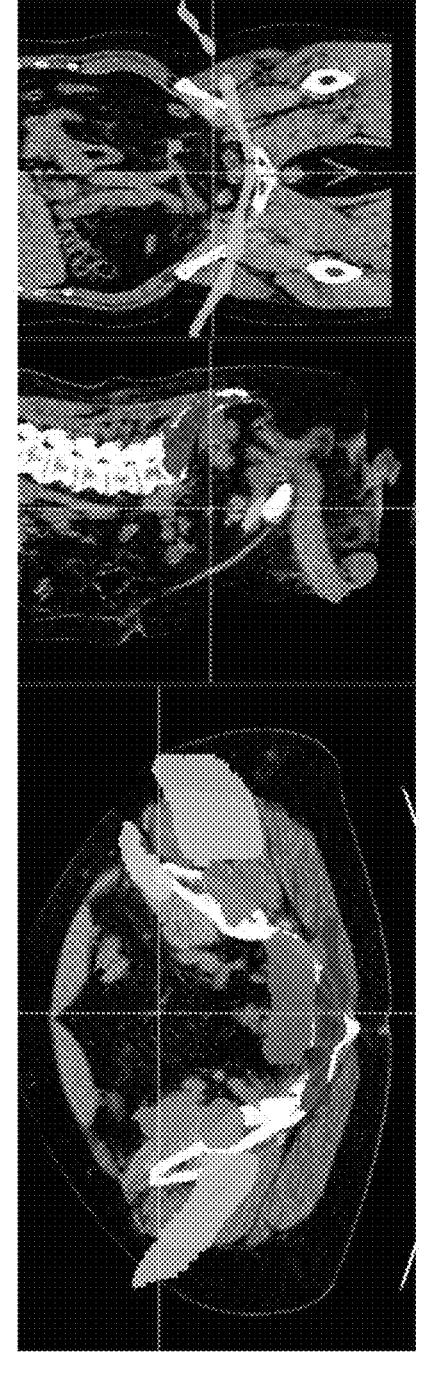
FIG. 21C is a set of three views of a CT image, overlaid with a pelvic atlas image, according to an illustrative embodiment.
Figure 21D:
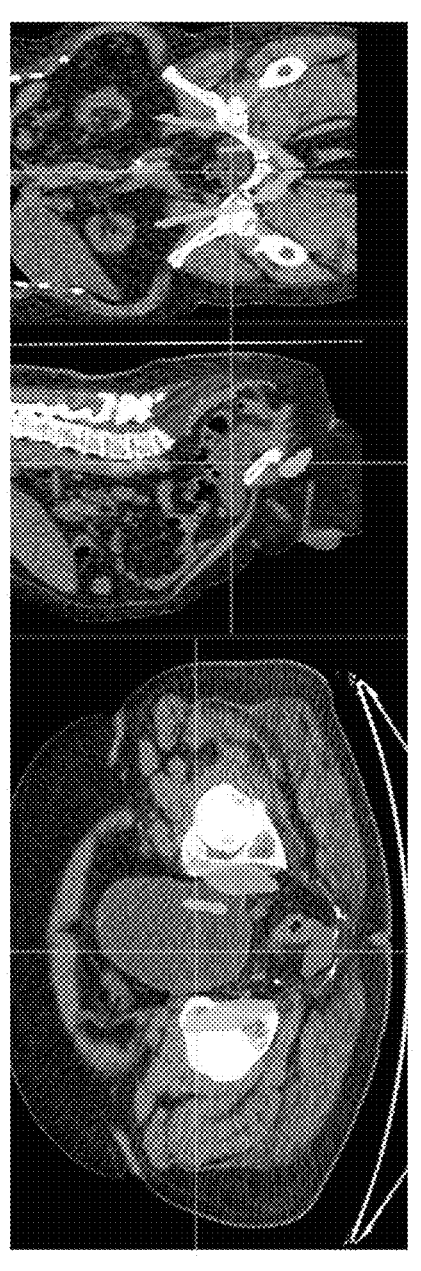
FIG. 21D is a set of three views of a CT image, overlaid with a pelvic atlas image, according to an illustrative embodiment.
Figure 21E:
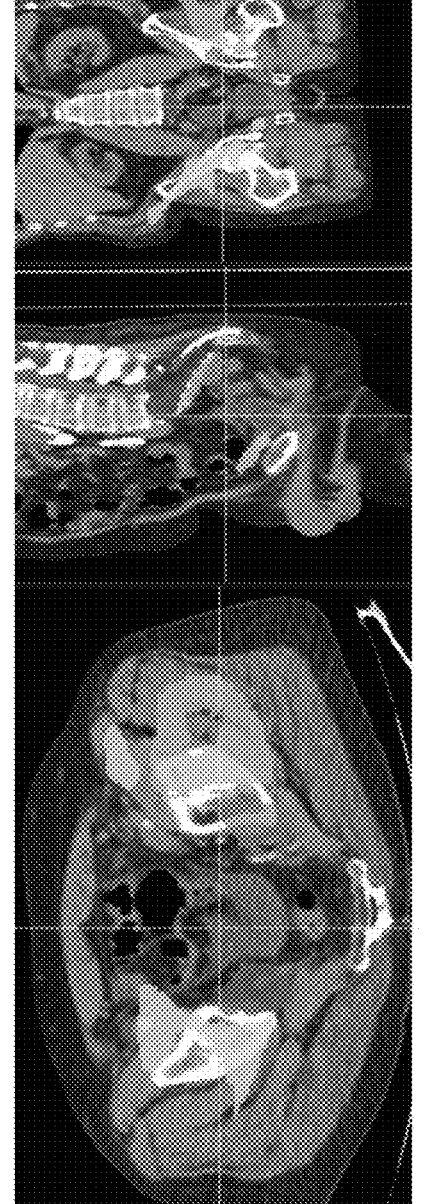
FIG. 21E is a set of three views of a CT image, overlaid with a pelvic atlas image, according to an illustrative embodiment.
Figure 21F:
FIG. 21F is a set of three views of a CT image, overlaid with a pelvic atlas image, according to an illustrative embodiment.

FIG. 19 shows a 3D segmentation map identifying iliac arteries, obturators, and a presacral region. These pelvic lymph node structures were segmented via a manual annotation by a nuclear medicine physicist (e.g., based on review of a CT image). CT images of three different subjects were used in this example. For each image, pelvic lymph node structures were segmented via a manual (expert) approach and pelvic bones identified via automated segmentation as described herein, to create three different atlas images. FIG. 20 shows two views of an atlas image created for one of the cases in this manner, showing both the segmented pelvic lymph structures and the segmented reference pelvic bones.

Figure 22:
FIG. 22 is a set of three views of a CT image, overlaid with a pelvic atlas image, according to an illustrative embodiment.

FIGS. 21A-F show six example registration transformations, performed to register, for each of the three cases, the pelvic atlas image obtained from that case with each of the anatomical segmentations of the other two cases. FIG. 22 shows results of registration of atlas image from case 1 with segmentation map from case 3. Based on the results, e.g., shown in FIG. 22, in certain cases, an approach that either uses non-rigid registration and/or a multi-step approach may offer improved performance.

Figure 23A:
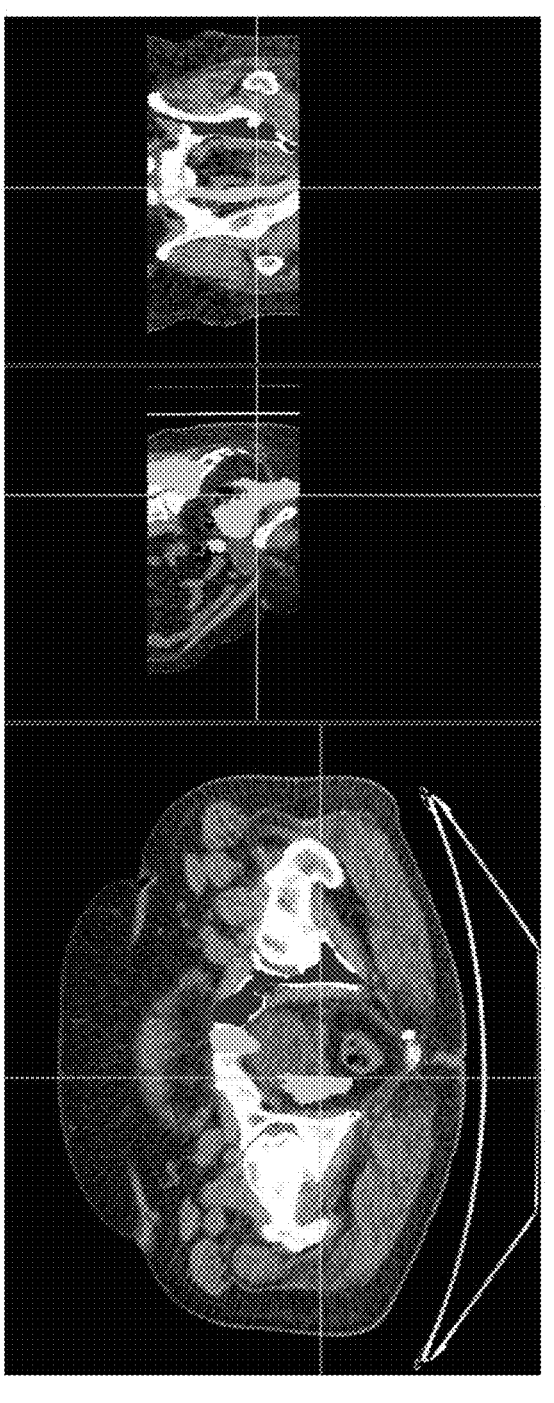
FIG. 23A is a set of three views of a CT image, overlaid with a pelvic atlas image, according to an illustrative embodiment.
Figure 23B:
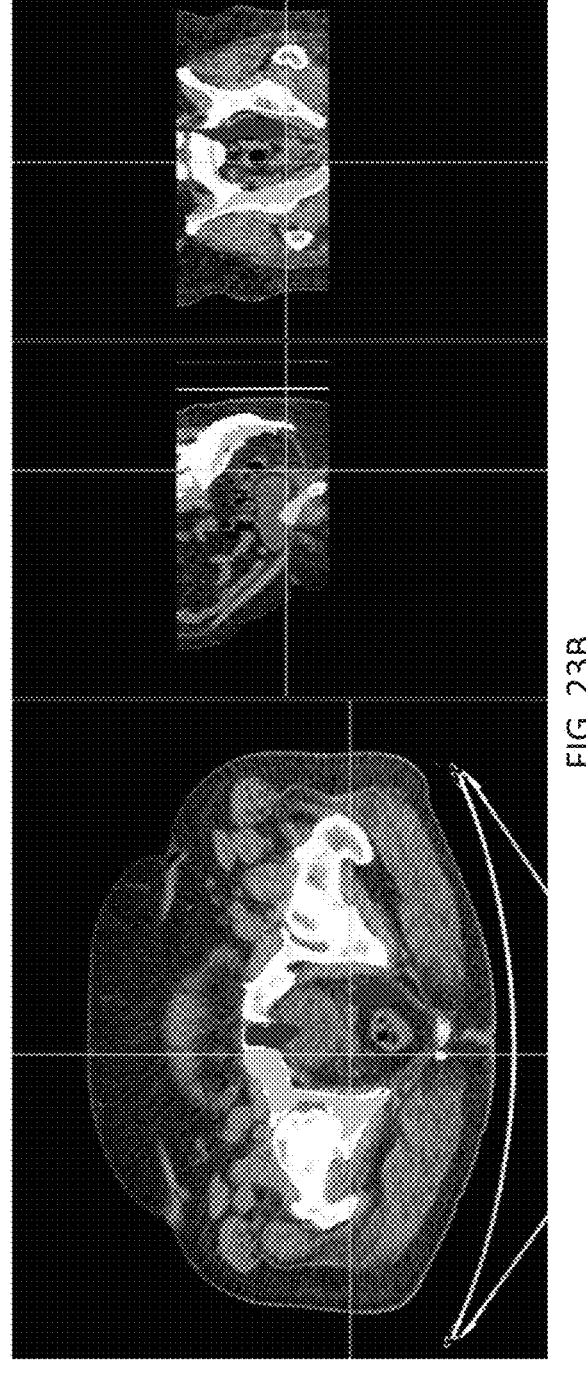
FIG. 23B is a set of three views of a CT image, overlaid with a pelvic atlas image, according to an illustrative embodiment.
Figure 23C:
FIG. 23C is a set of three views of a CT image, overlaid with a pelvic atlas image, according to an illustrative embodiment.
Figure 23C:
Figure 23C:
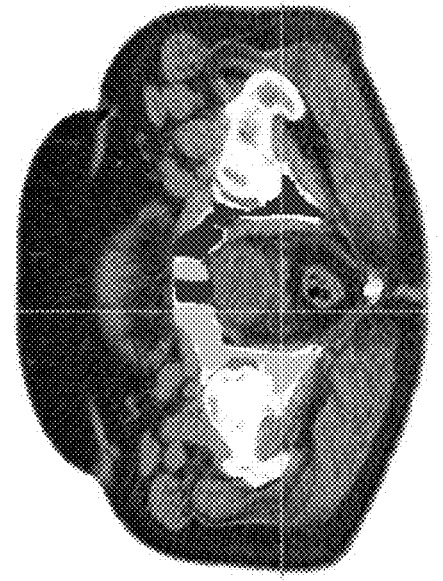
Figure 23D:
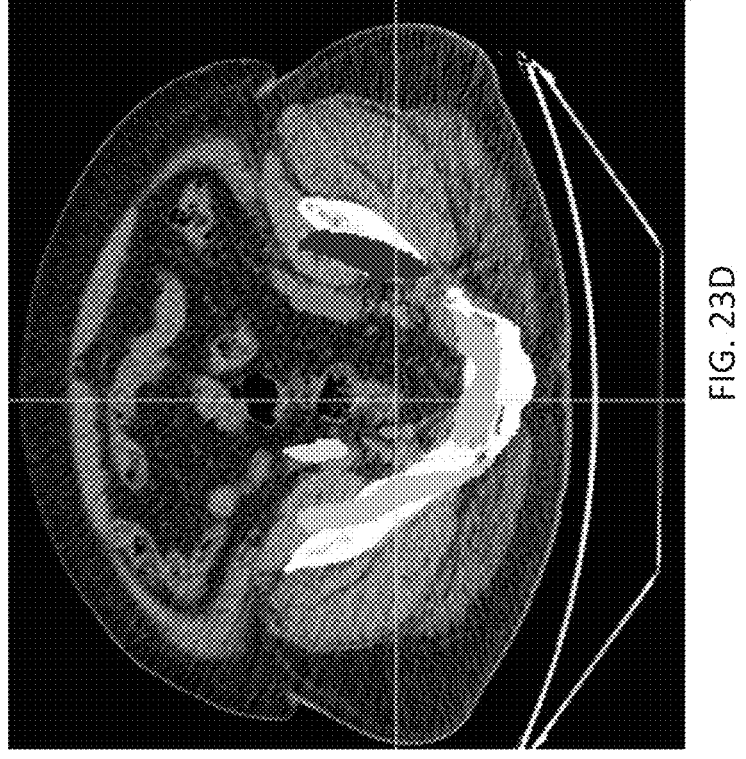
FIG. 23D is a view of a CT image, overlaid with a pelvic atlas image, according to an illustrative embodiment.
Figure 24A:
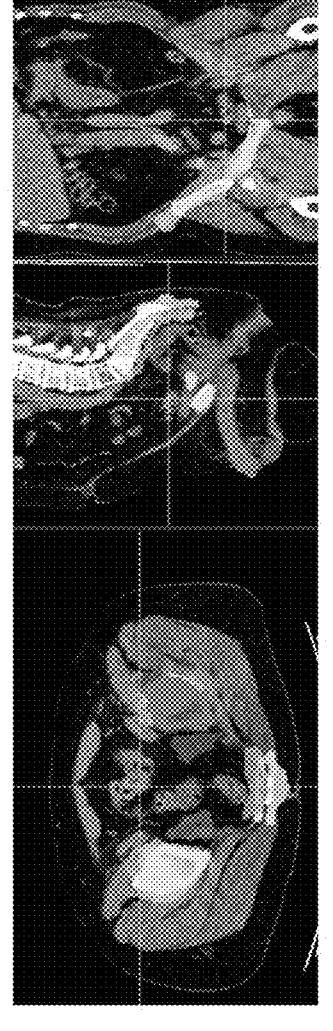
FIG. 24A is a set of three views of a CT image, overlaid with a pelvic atlas image, according to an illustrative embodiment.
Figure 24B:
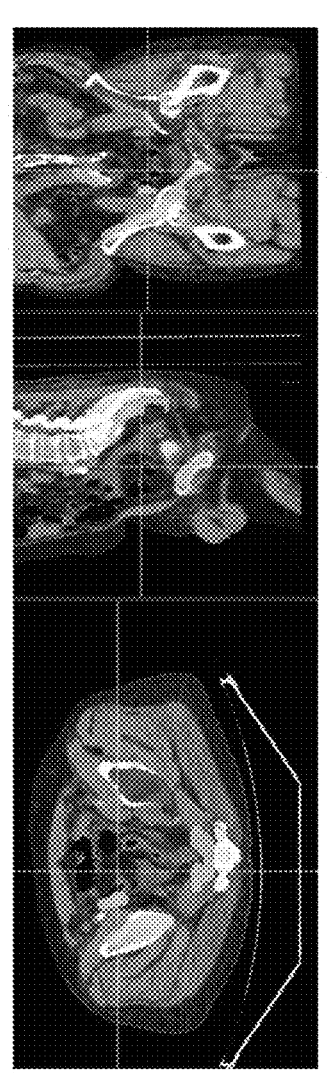
FIG. 24B is a set of three views of a CT image, overlaid with a pelvic atlas image, according to an illustrative embodiment.
Figure 24C:
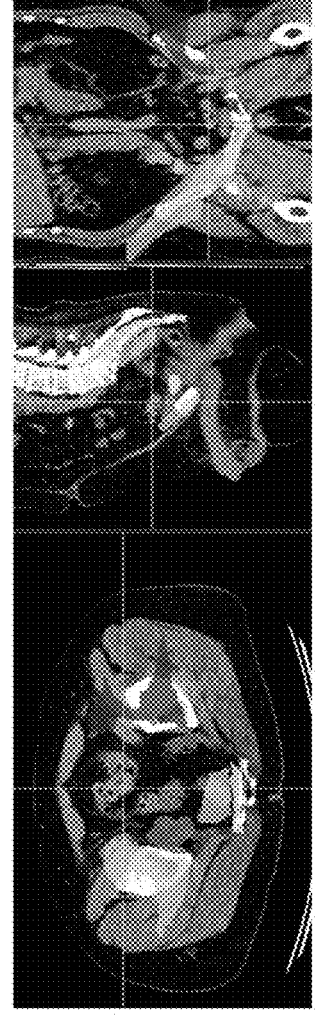
FIG. 24C is a set of three views of a CT image, overlaid with a pelvic atlas image, according to an illustrative embodiment.
Figure 24D:
FIG. 24D is a set of three views of a CT image, overlaid with a pelvic atlas image, according to an illustrative embodiment.
Figure 24E:
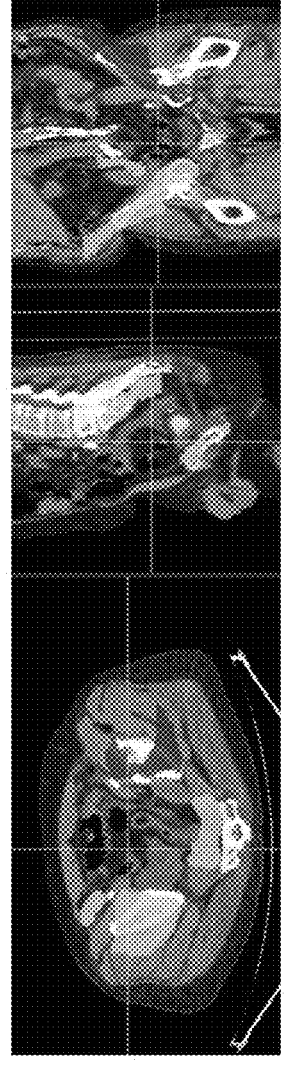
FIG. 24E is a set of three views of a CT image, overlaid with a pelvic atlas image, according to an illustrative embodiment.
Figure 24F:
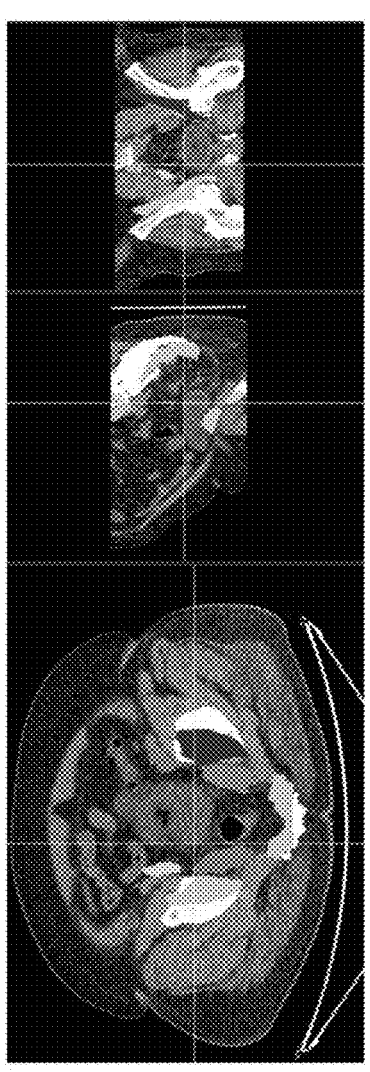
FIG. 24F is a set of three views of a CT image, overlaid with a pelvic atlas image, according to an illustrative embodiment.

FIGS. 23A-D demonstrate an example approach whereby affine registration is used in a multi-step fashion, wherein a first registration is performed using pelvic bone landmarks on a left side (FIG. 23A), and a second registration is performed using pelvic bone landmarks on a right side (FIG. 23B). A final deformation (e.g., transformation) was be determined based on the first and second registration transformations, in this example, as a weighted average with weights based on a distance between each pixel and a hip bone region. The result of the final registration, showing the right and left hip bones of the transformed atlas image overlaid on the target CT image is shown in FIG. 23C. FIG. 23D shows an axial view with the external and internal iliac regions of the transformed pelvic atlas image in close proximity to the corresponding regions in the target CT image.

FIGS. 24A-F show results analogous to those shown in FIGS. 23A-D, but for the multi-step registration approach.

Example 3

This example demonstrates an embodiment whereby multiple pelvic atlases that identify pelvic-lymph sub-regions using planar reference markers are used to suggest a pelvic lymph classification for segmented hotspots.
Pelvic Atlas Image Creation In this example, ten pelvic atlas images were created from a set of ten low dose CT scans for ten patients. The following regions, corresponding to locations of certain pelvic lymph nodes, were annotated in the low dose CT scans by a nuclear medicine specialist: left and right common iliac arteries, left and right external iliac arteries, left and right internal iliac arteries, regions where lymph nodes would be considered as obturator nodes (both left and right side), and a region where lymph nodes would be considered presacral nodes. Each of the (left and right) obturator regions were extended to also include certain portions of nearby tissue in their vicinity, such as the obturator muscles. The presacral region was extended to encompass a portion of a rectum and adjacent muscles.

The ten low does CT images were also segmented automatically (e.g., as described in Section B, herein) to identify regions corresponding to 3D representations of pelvic bones. In particular, a left hip bone, a right hip bone and a (combined) sacrum and coccyx region (i.e., a single region identified as comprising representations of a sacrum and coccyx) were identified.

Figures 26A, 26B:
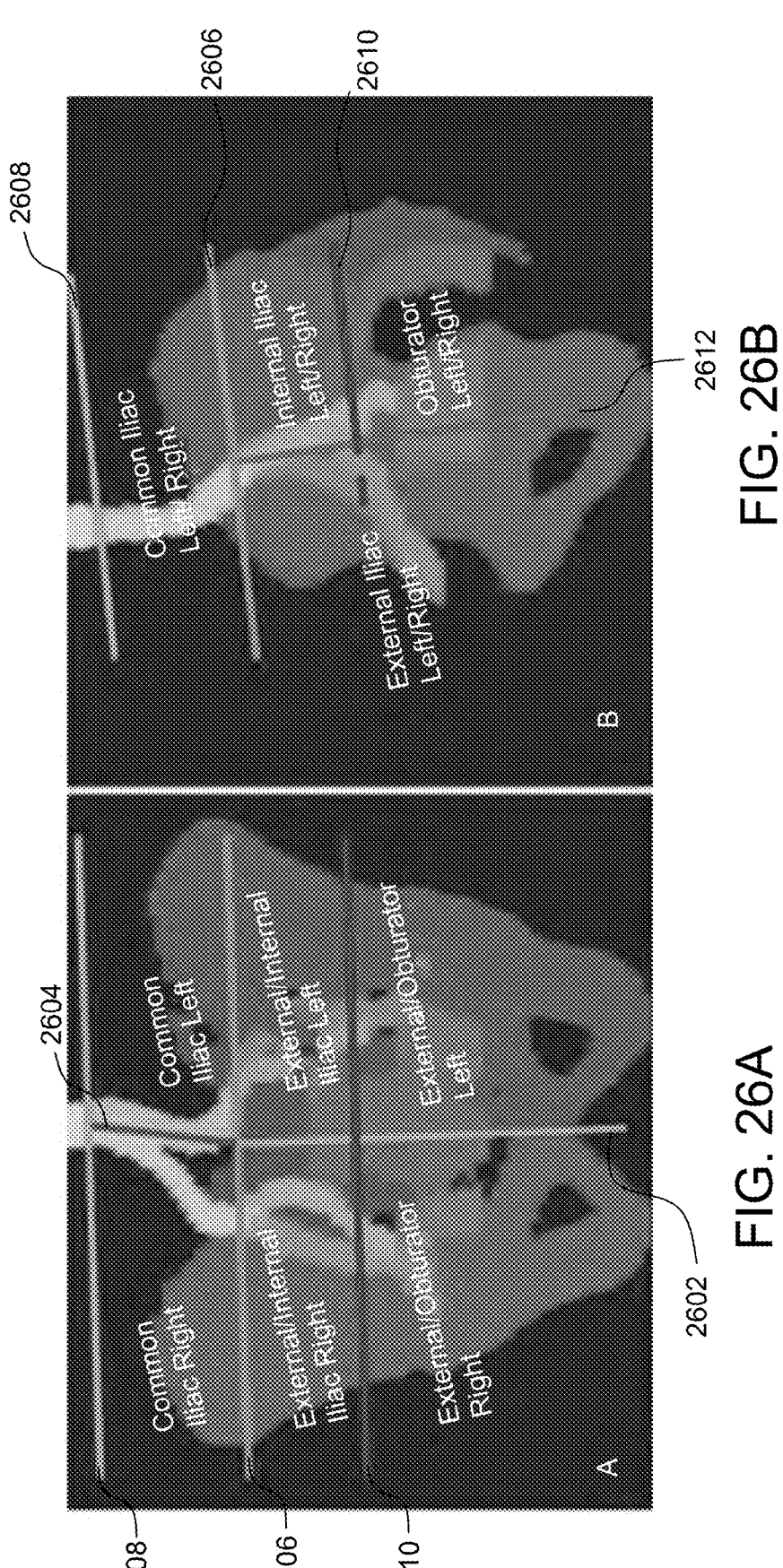
FIG. 26A is an illustration of a pelvic region separated by six planes, according to an illustrative embodiment.
FIG. 26B is another view of the illustration of the pelvic region, separated by six planes, from FIG. 26A, according to an illustrative embodiment.

The above-described annotations of iliac artery regions were then used together with the segmented pelvic bones to create six planar reference markers in each pelvic atlas image, to subdivide the pelvic volume into various pelvic lymph regions of interest, as shown in FIGS. 26A and 26B.

In particular, a first planar reference marker 2602 was created to separate internal and external iliac arteries on a left hand side from those on a right hand side—e.g., a median plane for the subject. To define this plane, three points—$P_1$, $P_2$, and $P_4$—described in Table 2, below, were manually placed in the pelvic atlas image volume.

TABLE 2

| Points used to define planar reference markers in example pelvic atlas images shown in FIGS. 26A and 26B. | |
| --- | --- |
| $P_1$ | Aorta bifurcation |
| $P_2$ | A left-right midpoint of common iliac bifurcations at a height of a lower point of a $5^{th}$ lumbar vertebrae. |
| $P_3$ | The most dorsal point of a spine of the subject, in a same image slice as $P_2$. |
| $P_4$ | A point where left and right pubic bones meet. |
| $P_5$, $P_6$, & $P_7$- | Points placed in a plane that separates the internal from the external iliac arteries. |
| $P_8$ | A most proximal point of one of the femoral heads. |

A second planar reference marker 2604 was created to separate a left side common iliac from a right side common iliac. Similar to first planar marker 2602, this, second, planar marker 2604 was designed to be perpendicular to a coronal plane, but slightly tilted, passing through points $P_2$ and $P_3$. This was to account for the aorta commonly running slightly to the patient's left-hand side and the aorta bifurcation being placed at the left-hand side of the median plane. Second planar reference marker 2604 also passes through a third point, $P_1$, placed at the aorta bifurcation as described in Table 2, above.

A third planar reference marker 2606 was created to be transversal with respect to the patient and placed where lumbar vertebra 5 meets the sacrum. To do so, a plane (i) perpendicular to first planar reference marker 2602 and (ii) perpendicular to a vector running from $P_1$ to $P_2$ and (iii) passing through $P_2$ was created as this third planar marker 2606.

A fourth planar reference marker 2608 was created to be parallel to third planar reference marker 2606, but passing through $P_1$ (as opposed to $P_2$). Fourth planar reference marker 2608 separates common iliac hotspots from distant lymph hotspots (e.g., with distant lymph hotspots located above fourth planar reference marker 2608).

A fifth planar reference marker 2610 was created to (also) be parallel to third planar reference marker 2606, but passing through $P_8$ (as opposed to $P_2$). Fifth planar reference marker 2610 separates internal iliac regions from obturator regions as shown in FIG. 26A and FIG. 26B.

A sixth planar reference marker 2612 was created to separate external iliac arteries from internal iliac arteries. Sixth planar reference marker 2612 was created by defining points at bifurcations of the left and right side common iliac arteries—$P_5$ and $P_6$, respectively—and a third point, $P_7$, located at a middle of external and internal iliac arteries in a sagittal plane.

All ten pelvic atlas images created were co-registered to each other using translation, followed by affine registration. These registrations were then evaluated by computing Dice scores. Two pelvic atlas images that performed best—i.e., had the highest Dice score(s)—were chosen to be two prospective pelvic atlas images to be used, and selected from (as described below), for registration with target anatomical segmentation maps and co-aligned PET images for purposes of identifying and classifying hotspots. This approach of using multiple pelvic atlas images was believed to account for variations in body type (e.g., weight, hip width, etc.) between different types of patients. Two particular pelvic atlas images were selected from the ten initial pelvic atlas images to reduce a number of prospective pelvic atlas images for which transformations to co-register with target segmentation map generated from a PET/CT imaging study (e.g., in the interest of computational efficiency) in the particular implementation described in this example. The particular approach—co-registering the initial set of pelvic atlas images with each other and selecting a subset (in this example, two) of pelvic atlas images that had highest overall Dice scores—used in this example was believed to identify the two most generally applicable pelvic atlas images out of the set. Other numbers of initial pelvic atlas images and other approaches for selecting a final set of prospective pelvic atlas images are contemplated.

Pelvic Atlas Image Registration

Figure 25:
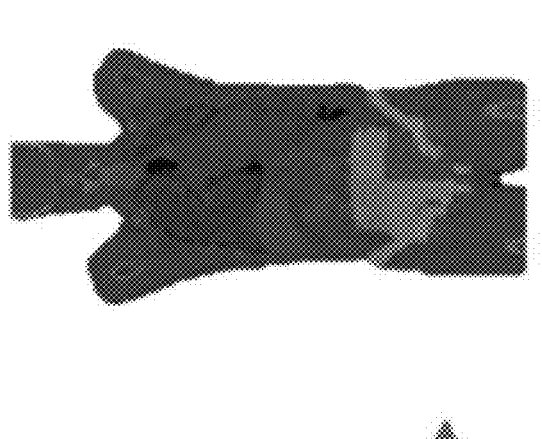
FIG. 25 is a schematic showing an overview of atlas registration, according to an illustrative embodiment.
Figure 25:
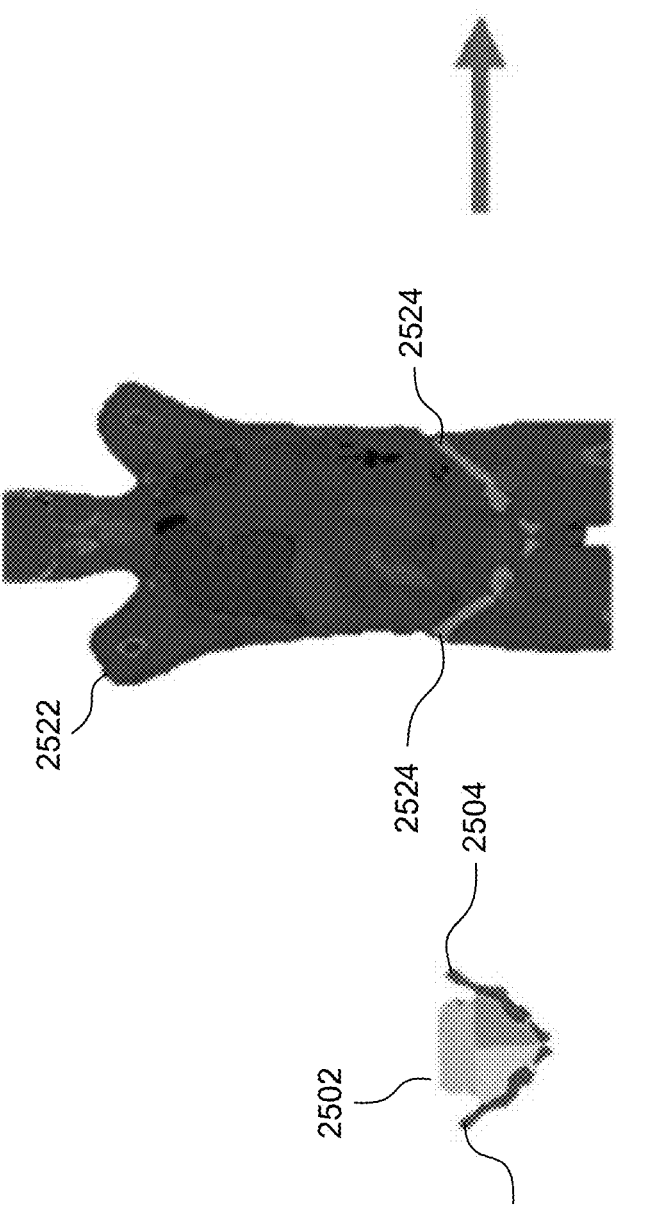

PET/CT imaging studies were analyzed using the two prospective pelvic atlas images created and selected, as described herein. FIG. 25 shows a schematic illustrating a pelvic atlas image 2502 and target 3D anatomical segmentation map 2522 to which the pelvic atlas image 2502 is co-registered. For a particular target PET/CT composite image, comprising a co-aligned target PET and target CT image, the target CT image was segmented to create the target 3D anatomical segmentation map 2522 that included identifications of pelvic bones, including a left and right hip bone, and a (single combined) sacrum and coccyx region. Hotspots were detected and segmented in the target PET image.

A pelvic atlas image of the two prospective pelvic atlas images was co-registered to the target 3D anatomical segmentation map 2522 in order to, in turn, align it with the target PET image so it could be used to classify hotspots in the target PET image as belonging to particular pelvic lymph sub-regions (e.g., nodes). A multi-step approach that included an initial atlas selection step in which a particular one 2502 of the two prospective pelvic atlas images was selected based on performance in a coarse registration with the pelvic bone regions 2524 identified within the target 3D anatomical segmentation map 2522, followed by a fine registration step in which the selected pelvic atlas was further transformed align individual reference pelvic bone regions 2504 to their corresponding regions 2524 within the target 3D segmentation map.

Atlas Selection (Coarse Registration). In a first, atlas selection, step, each of the two prospective pelvic atlas images was co-registered to the target 3D anatomical segmentation map via a coarse registration approach. Coarse registration was performed using 3×3×3 mm/voxel resolution for images and masks/maps created therefrom. As described herein, each of the two prospective pelvic atlas images comprised identifications of three reference pelvic bone regions—a left hip bone, a right hip bone, and a sacrum and coccyx region. Corresponding pelvic bone regions were also in the target segmentation map, having been segmented in the CT image. To transform each particular one of the prospective pelvic atlas images to co-register it to the target 3D anatomical segmentation map, a reference pelvic bone mask that comprised the three reference pelvic bone regions (left and right hip bones, and sacrum and coccyx region). A reference bone distance map was then created from the reference pelvic bone mask by assigning voxels lying outside of the masked pelvic bone regions a value of zero and assigning each particular voxel within the masked pelvic bone region a value computed based on a distance from the particular voxel to an edge of the masked pelvic bone region. A corresponding target pelvic bone mask and target bone distance map was created from the target 3D anatomical segmentation map. For each pelvic atlas image, the reference bone distance map was co-registered to the target pelvic bone distance map using translation followed by affine transformation and the resulting overall transformation applied to the reference pelvic bone mask to create a transformed pelvic bone mask. For each prospective pelvic atlas image, a Dice score was computed between the transformed pelvic bone mask and the target pelvic bone mask. The prospective pelvic atlas image with the highest Dice score was selected as a best-fit pelvic atlas image for further registration and use in classifying hotspots.

Atlas Registration (Fine Registration). The best-fit pelvic atlas image was then further registered (e.g., transformed) to optimize fit to the current PET/CT imaging study via a fine registration approach. The fine registration was a multi-step approach, in which preliminary transformations were computed using left and right hip bone regions and then combined to create a final, overall transformation. Fine registration was performed using 3×3×3 mm/voxel resolution for images and masks/maps created therefrom.

In particular, a left hip bone reference region of the best-fit pelvic atlas image was used to create a left hip bone reference mask and a corresponding, target left hip bone mask was created from the left hip bone region of the target 3D anatomical segmentation map. Distance maps were created (e.g., similar to as described in respect to the coarse registration step, above) for these masks and co-registered using translation followed by affine registration operations. This procedure was repeated, using a right hip bone reference region of the best-fit pelvic atlas image (e.g., to create a right hip bone reference mask) and a corresponding right hip bone region (e.g., and target left hip bone mask was created from) of the target 3D anatomical segmentation map. In this manner, two transformation operations were determined, one based on left-side hip bones of and another based on right-side hip bones. These left and right side transformations were represented via two distortion fields, $D_{hip-left}$ and $D_{hip-right}$, having 3×1×1 mm/voxel resolution. The distortion fields are situated in voxel space of the target 3D segmentation map, with each voxel of a distortion field comprising a 3D vector that points to (e.g., identifies) a particular voxel in the best-fit pelvic atlas image from which it should fetch its value.

To combine the left and right hip distortion fields, two distance maps—$d_{hip-left}$ and $d_{hip-right}$—were generated based on distances to the left and right hip bone regions, respectively, within the target 3D segmentation map. In particular, $d_{hip-left}$, was generated as a 3D matrix, with (i) each voxel outside the left hip bone region of the target 3D segmentation map assigned a value based on a (e.g., equal to a) distance from that voxel to the left hip bone region and (ii) voxels inside the left hip bone region assigned a zero value. Likewise, $d_{hip-right}$, was generated as a 3D matrix, with (i) each voxel outside the right hip bone region of the target 3D segmentation map assigned a value based on a (e.g., equal to a) distance from that voxel to the right hip bone region and (ii) voxels inside the right hip bone region assigned a zero value. A weighted distortion field, $D_w$, was created via a voxel-wise weighting of $D_{hip-left}$ and $D_{hip-right}$ according to the $d_{hip-left}$ and $d_{hip-right}$ distance maps, as shown in Equation (1), below:

$$D_w = \frac{d_{hip-right}}{d_{hip-right} + d_{hip-left}} D_{hip-left} + \frac{d_{hip-left}}{d_{hip-right} + d_{hip-left}} D_{hip-right} \qquad (1)$$

This operation allows for creation of, $D_w$, as a non-rigid distortion field.

The best-fit pelvic atlas image, A, was then transformed to displace it into the coordinate space of the target coordinate space (i.e., the coordinate space of target 3D segmentation map) using $D_e$ to create a transformed pelvic atlas image, $P_w$—i.e., $P_w=D_w(A)$.

Since the weighted distortion field, $D_w$, is calculated using left and right hip bones, but not the combined sacrum and coccyx region, a final transformation was created to incorporate the initial, coarse registration transformation used to select the best-fit pelvic atlas image, which was calculated using the combined sacrum and coccyx region, to map the presacral node sub-region from the pelvic atlas image to the target image space. In particular, referring to the distortion field determined using the coarse registration approach described above, used to select the best-fit pelvic atlas image, as $D_{best-fit}$, a second transformed pelvic atlas image, $P_{best-atlas}$ was created as $P_{best-fit}=D_{best-fit}(A)$.

A final, combined transformed atlas, $P_{comb}$, was then constructed according to Equation (2), below, thereby using the atlas transformed according to the left-right hip weighted distortion field for the iliac and obturator regions, and the best-fit selection transformation, which considers positioning of the sacrum and coccyx region, to transfer the presacral region to the target coordinate space.

$$P_{comb} = \begin{cases} P_w & \text{if } P_{best-fit} \neq \text{presacral} \\ \text{presacral} & \text{if } P_{best-fit} = \text{presacral} \end{cases} \qquad (2)$$

The final resultant transformed pelvic atlas was then resampled to match the original resolution of the target 3D anatomical segmentation map, and pasted into a coordinate system corresponding to a full volume of the target CT scan. This result was then resampled to match the coordinate system and resolution of the target PET image, where it could then be used to classify hotspot locations according to the locations shown in FIGS. 26A and 26B.

G. Classifying Distant Lymph Metastases

Figure 27:
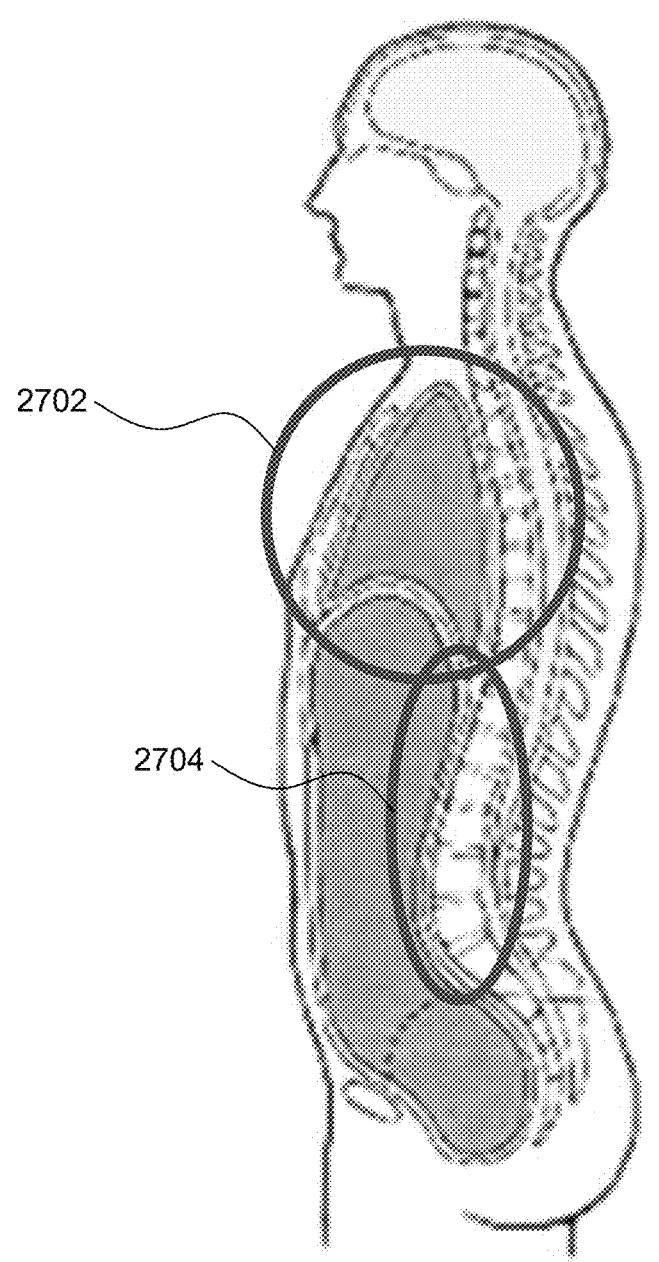
FIG. 27 is a diagram showing certain regions relevant for classification of metastases in distant lymph, according to an illustrative embodiment.

In certain embodiments, hotspots corresponding to lesions that are located outside a pelvic region, such as in distant lymph may be classified. For example, as shown in FIG. 27, in certain embodiments hotspots may be classified based whether they correspond to lesions in locations above a subject's diaphragm (e.g., supradiaphragmatic) 2702 and/or behind an abdominal cavity (e.g., retroperitoneal) 2704.

Figure 28:
FIG. 28 is a diagram illustrating an example process for classifying hotspots representing potential distant metastases, according to an illustrative embodiment.
Figure 29:
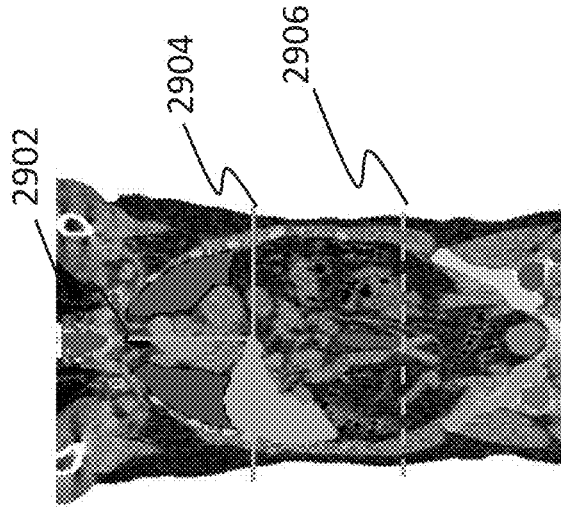
FIG. 29 is a set of images showing markers for classifying distant lymph, according to an illustrative embodiment.
Figure 29:
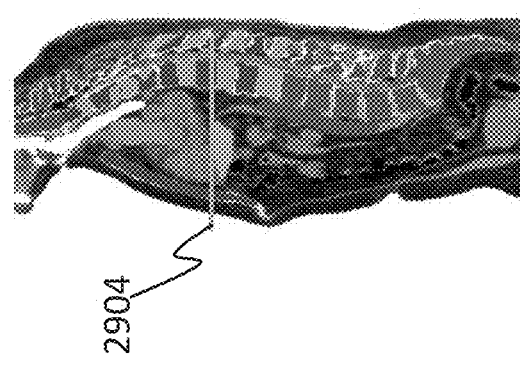
Figure 29:
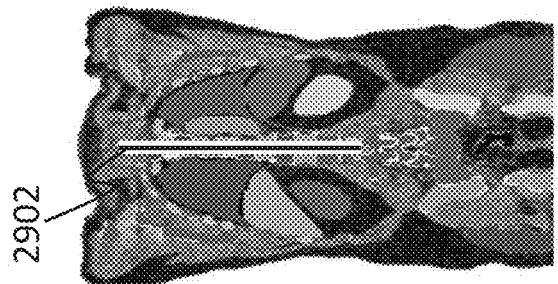

FIG. 28 illustrates an example process 2800 for classifying hotspots in this manner, based on various landmarks identified, e.g., within a CT image. Landmarks may be identified, in certain embodiments, based on analysis of a segmentation map created from segmentation of an anatomical image. Segmentation of an anatomical image for use in classifying distant metastases can be accomplished via various approaches as described herein and in further detail in PCT publication WO/2020/144134, entitled "Systems and Methods for Platform Agnostic Whole Body Segmentation," and published Jul. 16, 2020, U.S. Patent Publication No. US 2021/0334974 A1, entitled "Systems and Methods for Deep-Learning-Based Segmentation of Composite Images," and published Oct. 28, 2021, and PCT publication WO/2022/

008374, entitled "Systems and Methods for Artificial Intelligence-Based Image Analysis for Detection and Characterization of Lesions," and published Jan. 13, 2022, the content of each of which is incorporated herein by reference in its entirety.

For example, as shown in FIG. 28, an anatomical segmentation map can be used to identify a medial line 2902 of a thoracic spine within a coronal plane, and an axial plane 2904 located at a superior point of a liver in a corresponding sagittal plane. Plane 2906 separates the pelvic region from the retroperitoneal region. In certain embodiments, hotspots are classified according to these whole-body landmarks. In particular, in certain embodiments, hotspots lying beneath plane 2906 are identified as located within a pelvic region, and may be further classified according to, for example, approaches for classifying pelvic lymph sub-regions as described herein. Hotspots located above axial plane 2906 but below axial plane 2904 are classified as representing potential retroperitoneal metastases. Hotspots located above axial plane are classified as supradiaphragmatic, with plane 2902 used to distinguish right hand versus left hand supradiaphragmatic lesions. In this manner, one or more whole body landmarks can be determined from an anatomical segmentation map computed by segmenting an anatomical image, and used to classify distant metastases.

H. Imaging Agents

As described herein, a variety of radionuclide labelled PSMA binding agents may be used as radiopharmaceutical imaging agents for nuclear medicine imaging to detect and evaluate prostate cancer. In certain embodiments, certain radionuclide labelled PSMA binding agents are appropriate for PET imaging, while others are suited for SPECT imaging.

i. PET Imaging Radionuclide Labelled PSMA Binding Agents

In certain embodiments, a radionuclide labelled PSMA binding agent is a radionuclide labelled PSMA binding agent appropriate for PET imaging.

In certain embodiments, a radionuclide labelled PSMA binding agent comprises [18F]DCFPyL (also referred to as PyL™; also referred to as DCFPyL-18F):

[18F]DCFPyL or a pharmaceutically acceptable salt thereof.

In certain embodiments, a radionuclide labelled PSMA binding agent comprises [18F]DCFBC:

[18F]DCFBC or a pharmaceutically acceptable salt thereof.

In certain embodiments, a radionuclide labelled PSMA binding agent comprises $^{68}$Ga-PSMA-HBED-CC (also referred to as $^{68}$Ga-PSMA-11):

[68]Ga-PSMA-HBED-CC or a pharmaceutically acceptable salt thereof.

In certain embodiments, a radionuclide labelled PSMA binding agent comprises PSMA-617:

PSMS-617 or a pharmaceutically acceptable salt thereof. In certain embodiments, the radionuclide labelled PSMA binding agent comprises $^{68}$Ga-PSMA-617, which is PSMA-617 labelled with $^{68}$Ga, or a pharmaceutically acceptable salt thereof. In certain embodiments, a radionuclide labelled PSMA binding agent comprises $^{177}$Lu-PSMA-617, which is PSMA-617 labelled with $^{177}$Lu, or a pharmaceutically acceptable salt thereof.

In certain embodiments, a radionuclide labelled PSMA binding agent comprises PSMA-I&T:

PSMS-I&T or a pharmaceutically acceptable salt thereof. In certain
embodiments, a radionuclide labelled PSMA binding
agent comprises ⁶⁸Ga-PSMA-I&T, which is PSMA-
I&T labelled with ⁶⁸Ga, or a pharmaceutically accept-
able salt thereof.

In certain embodiments, a radionuclide labelled PSMA
binding agent comprises PSMA-1007:

PSMA-1007 or a pharmaceutically acceptable salt thereof. In certain embodiments, a radionuclide labelled PSMA binding agent comprises $^{18}$F-PSMA-1007, which is PSMA-1007 labelled with $^{18}$F, or a pharmaceutically acceptable salt thereof.

In certain embodiments, a radionuclide labeled PSMA binding agent comprises 18F-JK-PSMA-7:

18F-JK-PSMA-7 or a pharmaceutically acceptable salt thereof.

ii. SPECT Imaging Radionuclide Labelled PSMA Binding Agents

In certain embodiments, a radionuclide labelled PSMA binding agent is a radionuclide labelled PSMA binding agent appropriate for SPECT imaging.

In certain embodiments, a radionuclide labelled PSMA binding agent comprises 1404 (also referred to as MIP-1404):

1404 or a pharmaceutically acceptable salt thereof.

In certain embodiments, a radionuclide labelled PSMA binding agent comprises 1405 (also referred to as MIP-1405):

1405 or a pharmaceutically acceptable salt thereof.

In certain embodiments, a radionuclide labelled PSMA binding agent comprises 1427 (also referred to as MIP-1427):

1427 or a pharmaceutically acceptable salt thereof.

In certain embodiments, a radionuclide labelled PSMA binding agent comprises 1428 (also referred to as MIP-1428):

1428 or a pharmaceutically acceptable salt thereof.

In certain embodiments, a PSMA binding agent is labelled with a radionuclide by chelating it to a radioisotope of a metal [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)].

In certain embodiments, 1404 is labelled with a radionuclide (e.g., chelated to a radioisotope of a metal). In certain embodiments, a radionuclide labelled PSMA binding agent comprises $^{99m}$Tc-MIP-1404, which is 1404 labelled with (e.g., chelated to) $^{99m}$Tc:

$^{99m}$Tc-MIP-1404 or a pharmaceutically acceptable salt thereof. In certain embodiments, 1404 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radio-isotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1404, with the other metal radioisotope substituted for $^{99m}$Tc.

In certain embodiments, 1405 is labelled with a radionu-clide (e.g., chelated to a radioisotope of a metal). In certain embodiments, a radionuclide labelled PSMA binding agent comprises $^{99m}$Tc-MIP-1405, which is 1405 labelled with (e.g., chelated to) $^{99m}$Tc:

$^{99m}$Tc-MIP-1405 or a pharmaceutically acceptable salt thereof. In certain embodiments, 1405 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radio-isotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1405, with the other metal radioisotope substituted for $^{99m}$Tc.

In certain embodiments, 1427 is labelled with (e.g., chelated to) a radioisotope of a metal, to form a compound according to the formula below:

1427 chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1427 is labelled.

In certain embodiments, 1428 is labelled with (e.g., chelated to) a radioisotope of a metal, to form a compound according to the formula below:

1428 chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1428 is labelled.

In certain embodiments, a radionuclide labelled PSMA binding agent comprises PSMA I&S:

PSMA I&S or a pharmaceutically acceptable salt thereof. In certain embodiments, a radionuclide labelled PSMA binding agent comprises $^{99m}$Tc-PSMA I&S, which is PSMA I&S labelled with $^{99m}$Tc, or a pharmaceutically acceptable salt thereof.

I. Computer System and Network Architecture

Figure 30:
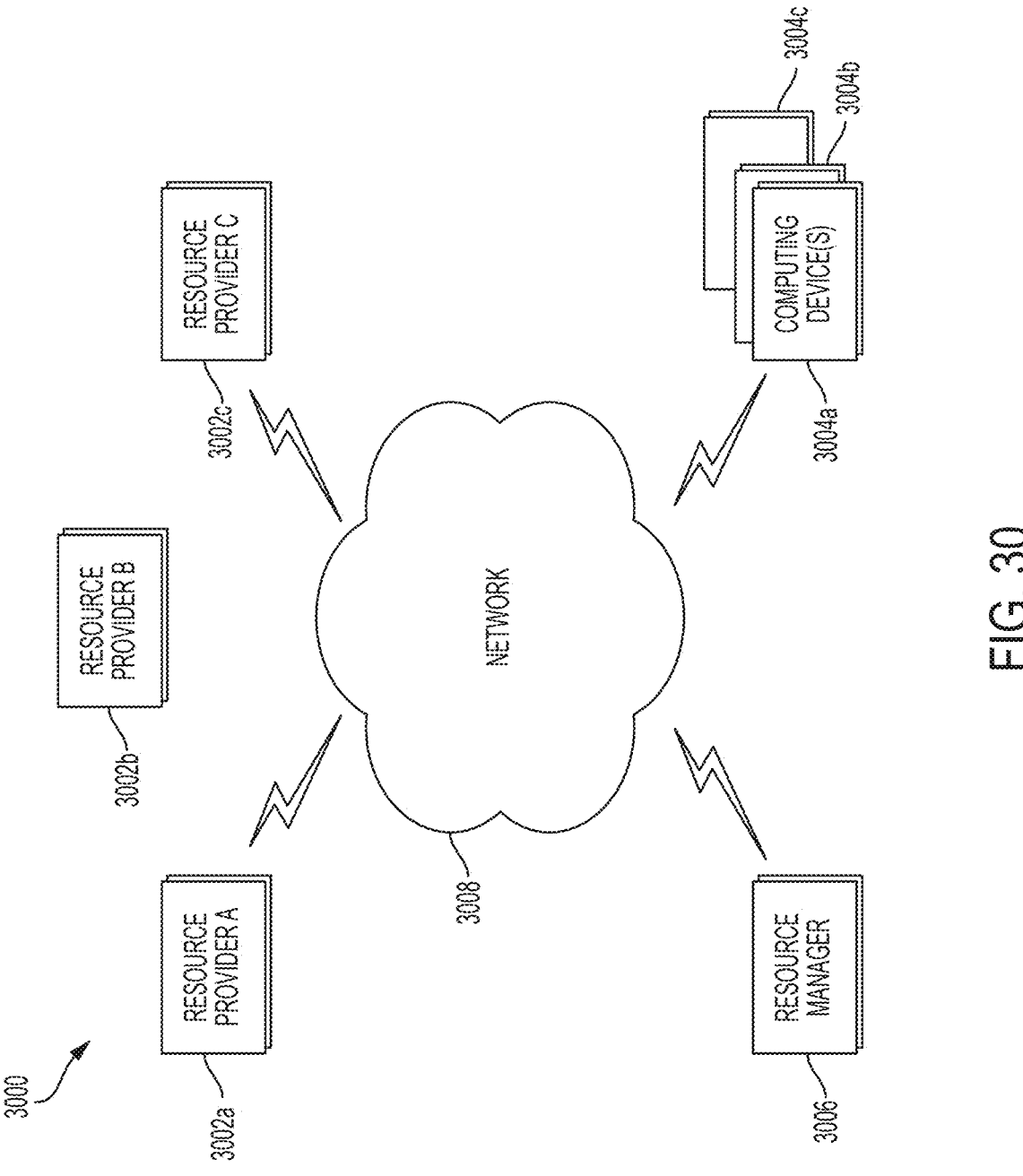
FIG. 30 is a block diagram of an exemplary cloud computing environment, used in certain embodiments.

As shown in FIG. 30, an implementation of a network environment 3000 for use in providing systems, methods, and architectures described herein is shown and described. In brief overview, referring now to FIG. 30, a block diagram of an exemplary cloud computing environment 3000 is shown and described. The cloud computing environment 3000 may include one or more resource providers 3002a, 3002b, 3002c (collectively, 3002). Each resource provider 3002 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 3002 may be connected to any other resource provider 3002 in the cloud computing environment 3000. In some implementations, the resource providers 3002 may be connected over a computer network 3008. Each resource provider 3002 may be connected to one or more computing device 3004a, 3004b, 3004c (collectively, 3004), over the computer network 3008.

The cloud computing environment 3000 may include a resource manager 3006. The resource manager 3006 may be connected to the resource providers 3002 and the computing devices 3004 over the computer network 3008. In some implementations, the resource manager 3006 may facilitate the provision of computing resources by one or more resource providers 3002 to one or more computing devices 3004. The resource manager 3006 may receive a request for a computing resource from a particular computing device 3004. The resource manager 3006 may identify one or more resource providers 3002 capable of providing the computing resource requested by the computing device 3004. The resource manager 3006 may select a resource provider 3002 to provide the computing resource. The resource manager 3006 may facilitate a connection between the resource provider 3002 and a particular computing device 3004. In some implementations, the resource manager 3006 may establish a connection between a particular resource provider 3002 and a particular computing device 3004. In some implementations, the resource manager 3006 may redirect a particular computing device 3004 to a particular resource provider 3002 with the requested computing resource.

Figure 31:
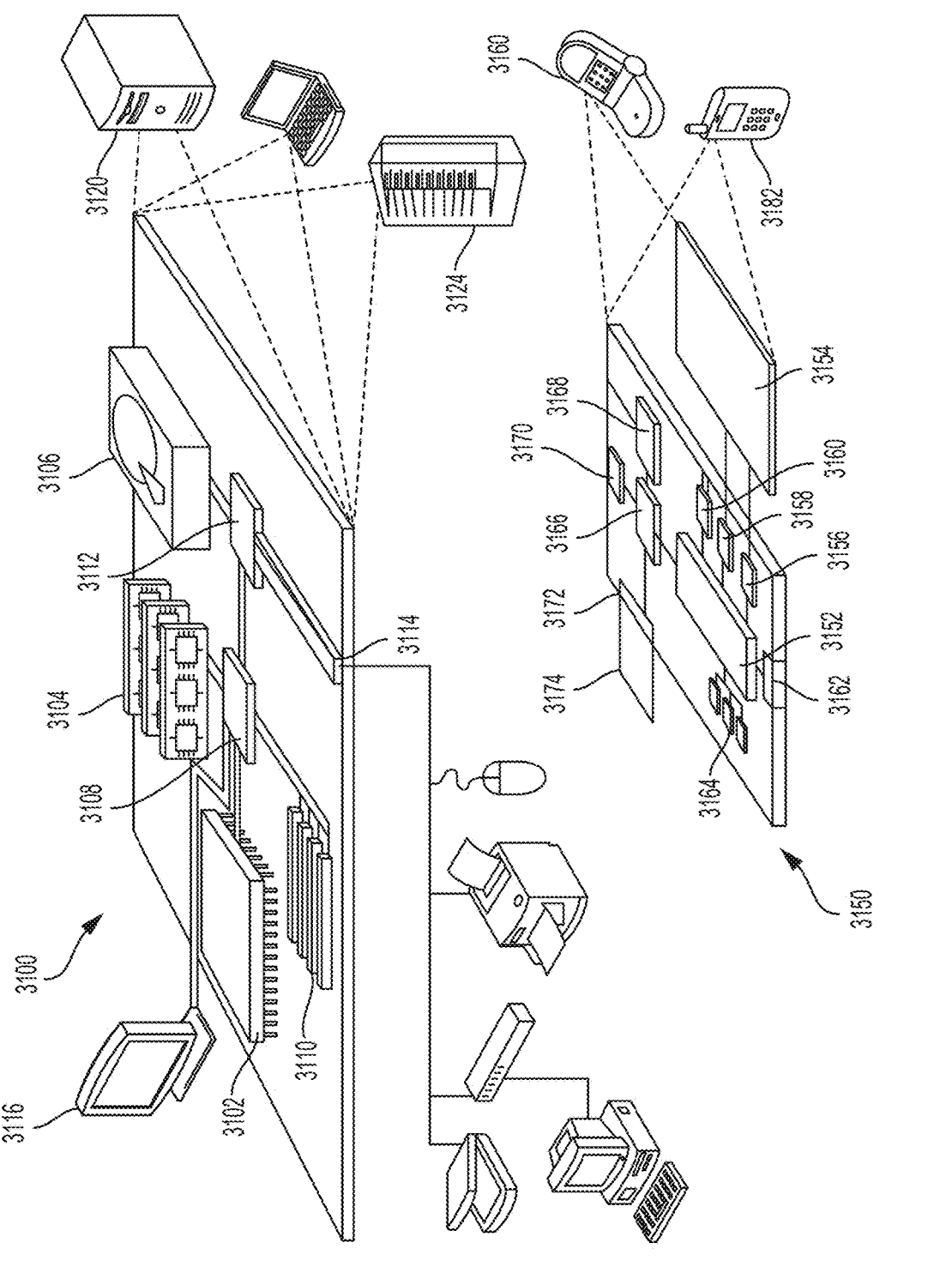
FIG. 31 is a block diagram of an example computing device and an example mobile computing device used in certain embodiments.

FIG. 31 shows an example of a computing device 3100 and a mobile computing device 3150 that can be used to implement the techniques described in this disclosure. The computing device 3100 is intended to represent various forms of digital computers, such as laptops, desktops, workstations, personal digital assistants, servers, blade servers, mainframes, and other appropriate computers. The mobile computing device 3150 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 3100 includes a processor 3102, a memory 3104, a storage device 3106, a high-speed interface 3108 connecting to the memory 3104 and multiple high-speed expansion ports 3110, and a low-speed interface 3112 connecting to a low-speed expansion port 3114 and the storage device 3106. Each of the processor 3102, the memory 3104, the storage device 3106, the high-speed interface 3108, the high-speed expansion ports 3110, and the low-speed interface 3112, are interconnected using various busses, and may be mounted on a common motherboard or in other manners as appropriate. The processor 3102 can process instructions for execution within the computing device 3100, including instructions stored in the memory 3104 or on the storage device 3106 to display graphical information for a GUI on an external input/output device, such as a display 3116 coupled to the high-speed interface 3108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 3104 stores information within the computing device 3100. In some implementations, the memory 3104 is a volatile memory unit or units. In some implementations, the memory 3104 is a non-volatile memory unit or units. The memory 3104 may also be another form of computer-readable medium, such as a magnetic or optical disk.

The storage device 3106 is capable of providing mass storage for the computing device 3100. In some implementations, the storage device 3106 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 3102), perform one or more methods, such as those described above. The instructions can also be stored by one or more storage devices such as computer- or machine-readable mediums (for example, the memory 3104, the storage device 3106, or memory on the processor 3102).

The high-speed interface 3108 manages bandwidth-intensive operations for the computing device 3100, while the low-speed interface 3112 manages lower bandwidth-intensive operations. Such allocation of functions is an example only. In some implementations, the high-speed interface 3108 is coupled to the memory 3104, the display 3116 (e.g., through a graphics processor or accelerator), and to the high-speed expansion ports 3110, which may accept various expansion cards (not shown). In the implementation, the low-speed interface 3112 is coupled to the storage device 3106 and the low-speed expansion port 3114. The low-speed expansion port 3114, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 3100 may be implemented in a number of different forms, as shown in the figure. For example, it may be implemented as a standard server 3120, or multiple times in a group of such servers. In addition, it may be implemented in a personal computer such as a laptop computer 3122. It may also be implemented as part of a rack server system 3124. Alternatively, components from the computing device 3100 may be combined with other components in a mobile device (not shown), such as a mobile computing device 3150. Each of such devices may contain one or more of the computing device 3100 and the mobile computing device 3150, and an entire system may be made up of multiple computing devices communicating with each other.

The mobile computing device 3150 includes a processor 3152, a memory 3164, an input/output device such as a display 3154, a communication interface 3166, and a transceiver 3168, among other components. The mobile computing device 3150 may also be provided with a storage device, such as a micro-drive or other device, to provide additional storage. Each of the processor 3152, the memory 3164, the display 3154, the communication interface 3166, and the transceiver 3168, are interconnected using various buses, and several of the components may be mounted on a common motherboard or in other manners as appropriate.

The processor 3152 can execute instructions within the mobile computing device 3150, including instructions stored in the memory 3164. The processor 3152 may be implemented as a chipset of chips that include separate and multiple analog and digital processors. The processor 3152 may provide, for example, for coordination of the other components of the mobile computing device 3150, such as control of user interfaces, applications run by the mobile computing device 3150, and wireless communication by the mobile computing device 3150.

The processor 3152 may communicate with a user through a control interface 3158 and a display interface 3156 coupled to the display 3154. The display 3154 may be, for example, a TFT (Thin-Film-Transistor Liquid Crystal Display) display or an OLED (Organic Light Emitting Diode) display, or other appropriate display technology. The display interface 3156 may comprise appropriate circuitry for driving the display 3154 to present graphical and other information to a user. The control interface 3158 may receive commands from a user and convert them for submission to the processor 3152. In addition, an external interface 3162 may provide communication with the processor 3152, so as to enable near area communication of the mobile computing device 3150 with other devices. The external interface 3162 may provide, for example, for wired communication in some implementations, or for wireless communication in other implementations, and multiple interfaces may also be used.

The memory 3164 stores information within the mobile computing device 3150. The memory 3164 can be implemented as one or more of a computer-readable medium or media, a volatile memory unit or units, or a non-volatile memory unit or units. An expansion memory 3174 may also be provided and connected to the mobile computing device 3150 through an expansion interface 3172, which may include, for example, a SIMM (Single In Line Memory Module) card interface. The expansion memory 3174 may provide extra storage space for the mobile computing device 3150, or may also store applications or other information for the mobile computing device 3150. Specifically, the expansion memory 3174 may include instructions to carry out or supplement the processes described above, and may include secure information also. Thus, for example, the expansion memory 3174 may be provide as a security module for the mobile computing device 3150, and may be programmed with instructions that permit secure use of the mobile computing device 3150. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 3152), perform one or more methods, such as those described above. The instructions can also be stored by one or more storage devices, such as one or more computer- or machine-readable mediums (for example, the memory 3164, the expansion memory 3174, or memory on the processor 3152). In some implementations, the instructions can be received in a propagated signal, for example, over the transceiver 3168 or the external interface 3162.

The mobile computing device 3150 may communicate wirelessly through the communication interface 3166, which may include digital signal processing circuitry where necessary. The communication interface 3166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 3168 using a radio-frequency. In addition, short-range communication may occur, such as using a Bluetooth®, Wi-Fi™, or other such transceiver (not shown). In addition, a GPS (Global Positioning System) receiver module 3170 may provide additional navigation- and location-related wireless data to the mobile computing device 3150, which may be used as appropriate by applications running on the mobile computing device 3150.

The mobile computing device 3150 may also communicate audibly using an audio codec 3160, which may receive spoken information from a user and convert it to usable digital information. The audio codec 3160 may likewise generate audible sound for a user, such as through a speaker, e.g., in a handset of the mobile computing device 3150. Such sound may include sound from voice telephone calls, may include recorded sound (e.g., voice messages, music files, etc.) and may also include sound generated by applications operating on the mobile computing device 3150.

The mobile computing device 3150 may be implemented in a number of different forms, as shown in the figure. For example, it may be implemented as a cellular telephone 3180. It may also be implemented as part of a smart-phone 3182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the various modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

The various described embodiments of the invention may be used in conjunction with one or more other embodiments unless technically incompatible. It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automatically processing 3D images of a subject to identify and/or characterize cancerous lesions within the subject, the method comprising:

(a) receiving, by a processor of a computing device, (i) a 3D functional image of the subject obtained using a functional imaging modality and (ii) a 3D anatomical image of the subject obtained using an anatomical imaging modality, wherein the 3D functional image and the 3D anatomical image are aligned and include a representation of a pelvic region of the subject, and wherein the 3D functional image includes one or more hotspots representing potential lesions within the pelvic region of the subject;

(b) segmenting, by the processor, the 3D anatomical image of the subject to identify representations of one or more pelvic bones within the 3D anatomical image of the subject, thereby creating a 3D segmentation map aligned with the 3D anatomical image of the subject and comprising one or more pelvic bone regions, wherein each pelvic bone region corresponds to a particular pelvic bone and/or group of one or more pelvic bones and identifies a representation of the particular pelvic bone and/or group of one or more pelvic bones within the 3D anatomical image;

(c) receiving, by the processor, a 3D pelvic atlas image comprising:

(A) an identification of one or more pelvic lymph sub-regions in the 3D pelvic atlas image; and (B) an identification of one or more reference pelvic bone regions in the 3D pelvic atlas image, wherein at least a portion of the one or more reference pelvic bone regions in the 3D pelvic atlas image corresponds to one or more of the pelvic bone regions of the 3D segmentation map;

(d) transforming, by the processor, the 3D pelvic atlas image to co-register it with the 3D segmentation map using (i) the one or more reference pelvic bone regions identified within the 3D pelvic atlas image and (ii) the one or more pelvic bone regions of the 3D segmentation map, thereby creating a transformed 3D pelvic atlas image comprising the identified one or more pelvic lymph sub-regions thereby aligned to the 3D anatomical image and segmentation thereof; and (e) determining, by the processor, for each of the one or more hotspots of the 3D functional image, a pelvic lymph classification using the identification of the one or more pelvic lymph sub-regions within the transformed 3D pelvic atlas image, wherein step (d) comprises:

determining a first transformation that aligns (i) a first subset of the one or more reference pelvic bone regions identified within the 3D pelvic atlas image to (ii) a corresponding first subset of the one or more pelvic bone regions of the 3D segmentation map;

determining a second transformation that aligns (i) a second subset of the one or more reference pelvic bone regions identified within the 3D pelvic atlas image to (ii) a corresponding second subset of the one or more pelvic bone regions of the 3D segmentation map; and determining a final overall transformation based on the first transformation and the second transformation and using the final overall transformation to transform the 3D pelvic atlas image.

2. The method of claim 1, wherein the 3D functional image is a positron emission tomography (PET) image obtained following administration, to the subject, of a radiopharmaceutical.

3. The method of claim 2, wherein the radiopharmaceutical comprises a Prostate Specific Membrane Antigen (PSMA) binding agent.

4. The method of claim 2, wherein the 3D anatomical image is a CT image.

5. The method of claim 1, wherein the 3D pelvic atlas image received at step (c) is selected from a set of multiple prospective 3D pelvic atlas images.

6. The method of claim 1, wherein the 3D pelvic atlas image comprises one or more reference markers, each of which demarks a boundary between two or more of the pelvic lymph sub-regions, thereby identifying the one or more pelvic lymph sub-regions within the 3D pelvic atlas image.

7. The method of claim 1, wherein the 3D pelvic atlas image comprises one or more representations of extended sub-volumes, each extended sub-volume corresponding to a particular one of the one or more pelvic lymph sub-regions and representing a local volume about a particular pelvic lymph node, thereby identifying the one or more pelvic lymph sub-regions within the 3D pelvic atlas image.

8. The method of claim 1, wherein the 3D pelvic atlas image comprises a 3D pelvic lymph segmentation map that identifies one or more pelvic lymph nodes.

9. The method of claim 1, comprising:

performing steps (c) and (d) for a plurality of prospective 3D pelvic atlas images to determine, for each of the prospective 3D pelvic atlas images, a corresponding transformed version and selecting, by the processor, a particular one of the prospective 3D pelvic atlas images as a best-fit 3D pelvic atlas image; and using the transformed version of the best-fit 3D pelvic atlas image as the transformed 3D pelvic atlas image to determine, at step (e), the pelvic lymph classification for each of the one or more hotspots.

10. The method of claim 1, wherein step (d) comprises:

performing coarse registration to co-register the 3D pelvic atlas image with the 3D segmentation map using (i) the one or more reference pelvic bone regions identified within the 3D pelvic atlas image and (ii) the one or more pelvic bone regions of the 3D segmentation map; and refining the 3D pelvic atlas image to create the transformed 3D pelvic atlas image using one or more reference organ regions identified within the 3D pelvic atlas image and one or more corresponding organ regions of the 3D segmentation map.

11. The method of claim 1, comprising:

receiving, at step (c), a plurality of prospective 3D pelvic atlas images;

at step (d):

for each particular one of the plurality of prospective 3D pelvic atlas images, determining a first registration transformation to co-register the particular prospective 3D pelvic atlas image with the 3D segmentation map using (i) the one or more reference pelvic bone regions identified within the particular prospective 3D pelvic atlas image and (ii) the one or more pelvic bone regions of the 3D segmentation map and transforming the particular prospective 3D pelvic atlas image according to the first registration transformation, thereby creating a plurality of transformed prospective pelvic atlas images;

selecting a particular one of the transformed prospective pelvic atlas images as an initial best-fit pelvic atlas image; and determining, for the initial best-fit pelvic atlas image, a second registration transformation to refine the co-registration of the initial best-fit pelvic atlas image with the 3D segmentation map using (i) the one or more reference pelvic bone regions identified within the initial best-fit pelvic atlas image and (ii) the one or more pelvic bone regions of the 3D segmentation map and transforming the initial best-fit pelvic atlas image according to the second registration transformation, thereby creating a final transformed pelvic atlas image; and using the final transformed pelvic atlas image as the transformed 3D pelvic atlas image to determine, at step (e), the pelvic lymph classification for each of the one or more hotspots.

12. The method of claim 1, wherein the one or more reference pelvic bone regions identified within the 3D pelvic atlas image comprise one or more members selected from the group consisting of a right hip bone region, a left hip bone region, a sacrum region, a coccyx region, and a sacrum and coccyx region.

13. The method of claim 1, wherein the one or more pelvic lymph sub-regions comprise one or more members selected from the group consisting of: a left internal iliac region, a right internal iliac region, a left external iliac region, a right external iliac region, a left common iliac region, a right common iliac region, a left obturator region, a right obturator region, and a presacral region.

14. The method of claim 1, wherein the one or more pelvic bone regions of the 3D segmentation map comprise one or more members selected from the group consisting of a right hip bone region, a left hip bone region, a sacrum region, a coccyx region, and a sacrum and coccyx region.

15. A system for automatically processing 3D images of a subject to identify and/or characterize cancerous lesions within the subject, the system comprising:

a processor of a computing device; and a memory having instructions stored thereon, wherein the instructions, when executed by the processor, cause the processor to:

(a) receive (i) a 3D functional image of the subject obtained using a functional imaging modality and (ii) a 3D anatomical image of the subject obtained using an anatomical imaging modality, wherein the 3D functional image and the 3D anatomical image are aligned and include a representation of a pelvic region of the subject, and wherein the 3D functional image includes one or more hotspots representing potential lesions within the pelvic region of the subject;

(b) segment the 3D anatomical image of the subject to identify representations of one or more pelvic bones within the 3D anatomical image of the subject, thereby creating a 3D segmentation map aligned with the 3D anatomical image of the subject and comprising one or more pelvic bone regions, wherein each pelvic bone region corresponds to a particular pelvic bone and/or group of one or more pelvic bones and identifies a representation of the particular pelvic bone and/or group of one or more pelvic bones within the 3D anatomical image;

(c) receive a 3D pelvic atlas image comprising:
    (A) an identification of one or more pelvic lymph sub-regions in the 3D pelvic atlas image; and
    (B) an identification of one or more reference pelvic bone regions in the 3D pelvic atlas image, wherein at least a portion of the one or more reference pelvic bone regions in the 3D pelvic atlas image corresponds to one or more of the pelvic bone regions of the 3D segmentation map;

(d) transform the 3D pelvic atlas image to co-register it with the 3D segmentation map using (i) the one or more reference pelvic bone regions identified within the 3D pelvic atlas image and (ii) the one or more pelvic bone regions of the 3D segmentation map, thereby creating a transformed 3D pelvic atlas image comprising the identified one or more pelvic lymph sub-regions thereby aligned to the 3D anatomical image and segmentation thereof; and (e) determine for each of the one or more hotspots of the 3D functional image, a pelvic lymph classification using the identification of the one or more pelvic lymph sub-regions within the transformed 3D pelvic atlas image, and wherein, at step (d), the instructions cause the processor to:
    determine a first transformation that aligns (i) a first subset of the one or more reference pelvic bone regions identified within the 3D pelvic atlas image to (ii) a corresponding first subset of the one or more pelvic bone regions of the 3D segmentation map;
    determine a second transformation that aligns (i) a second subset of the one or more reference pelvic bone regions identified within the 3D pelvic atlas image to (ii) a corresponding second subset of the one or more pelvic bone regions of the 3D segmentation map; and
    determine a final overall transformation based on the first transformation and the second transformation and use the final overall transformation to transform the 3D pelvic atlas image.

16. The system of claim 15, wherein the 3D functional image is a positron emission tomography (PET) image obtained following administration, to the subject, of a radiopharmaceutical.

17. A method for automatically processing 3D images of a subject to identify one or more pelvic lymph regions therein, the method comprising:

(a) receiving, by a processor of a computing device, (i) a 3D functional image of the subject obtained using a functional imaging modality and (ii) a 3D anatomical image of the subject obtained using an anatomical imaging modality, wherein the 3D functional image and the 3D anatomical image are aligned and include a representation of a pelvic region of the subject, and wherein the 3D functional image includes one or more hotspots representing potential lesions within the pelvic region of the subject;

(b) segmenting, by the processor, the 3D anatomical image of the subject to identify representations of one or more pelvic bones within the 3D anatomical image of the subject, thereby creating a 3D segmentation map aligned with the 3D anatomical image of the subject and comprising one or more pelvic bone regions, wherein each pelvic bone region corresponds to a particular pelvic bone and/or group of one or more pelvic bones and identifies a representation of the particular pelvic bone and/or group of one or more pelvic bones within the 3D anatomical image, and wherein the one or more pelvic bone regions comprise a left hip bone region that identifies a representation of a left hip bone within the 3D anatomical image and a right hip bone region that identifies a representation of a right hip bone within the 3D anatomical image;

(c) receiving, by the processor, a plurality of prospective 3D pelvic atlas images, each particular prospective 3D pelvic atlas image comprising:
    (A) an identification of one or more pelvic lymph sub-regions in the particular prospective 3D pelvic atlas image; and
    (B) an identification of one or more reference pelvic bone regions in the particular 3D pelvic atlas image, wherein the one or more reference pelvic bone regions comprise a left reference hip bone region corresponding to the left hip bone region of the 3D segmentation map and a right reference hip bone region corresponding to the right hip bone region of the 3D segmentation map;

(d) for each particular prospective pelvic atlas image of the plurality of prospective 3D pelvic atlas images, determining, by the processor, a corresponding coarse registration transformation that aligns (i) a reference pelvic bone region comprising the one or more reference pelvic bone regions identified within the particular prospective pelvic atlas image to (ii) a target pelvic bone region comprising the one or more pelvic bone regions of the 3D segmentation map;

(e) transforming, by the processor, each one of the plurality of prospective 3D pelvic atlas images according to its corresponding coarse registration transformation to create a plurality of transformed prospective pelvic atlas images;

(f) selecting, by the processor, a best-fit pelvic atlas image from the plurality of prospective 3D pelvic atlas images based on the plurality of transformed prospective pelvic atlas images;

(g) determining, by the processor, a fine registration transformation for the best-fit pelvic atlas image by:
    determining a left-side transformation that aligns (i) the left reference hip bone region of the best-fit pelvic atlas image with (ii) the left hip bone region of the 3D segmentation map;

determining a right-side transformation that aligns (i) the right reference hip bone region of the best-fit pelvic atlas image with (ii) the right hip bone region of the 3D segmentation map; and determining a weighted transformation based on the left-side transformation and the right-side transformation;

(h) transforming, by the processor, the best-fit pelvic atlas image using the weighted transformation to create a final transformed pelvic atlas image; and (i) determining, by the processor, for each of the one or more hotspots of the 3D functional image, a pelvic lymph classification using the identification of the one or more pelvic lymph sub-regions within the final transformed 3D pelvic atlas image.

18. The method of claim 17, wherein:

the one or more pelvic bone regions of the 3D segmentation map comprise a sacrum and coccyx region identifying a representation of sacrum and coccyx bones within the 3D anatomical image;

the one or more pelvic lymph sub-regions comprise a presacral region;

the one or more reference pelvic bone regions of the pelvic atlas images comprise a reference sacrum and coccyx region;

step (d) comprises, for each particular prospective pelvic atlas image, determining, as the corresponding coarse registration transformation, a transformation that aligns (i) a reference pelvic bone region comprising the left reference hip bone region, the right reference hip bone region, and the reference sacrum and coccyx region within the particular prospective pelvic atlas image to (ii) a target pelvic bone region comprising the left hip bone region, the right hip bone region, and the sacrum and coccyx region of the 3D segmentation map; and step (g) comprises combining the weighted transformation with the coarse registration transformation determined for the best-fit pelvic atlas image at step (d) by applying the coarse registration transformation to transform the presacral region of the best-fit pelvic atlas image and applying the weighted transformation to transform other regions of the best-fit pelvic atlas image.

19. A method for automatically processing 3D images of a subject to identify and/or characterize cancerous lesions within the subject, the method comprising:

(a) receiving, by a processor of a computing device, (i) a 3D functional image of the subject obtained using a functional imaging modality and (ii) a 3D anatomical image of the subject obtained using an anatomical imaging modality, wherein the 3D functional image and the 3D anatomical image are aligned and include a representation of a pelvic region of the subject, and wherein the 3D functional image includes one or more hotspots representing potential lesions within the pelvic region of the subject;

(b) segmenting, by the processor, the 3D anatomical image of the subject to identify representations of one or more pelvic bones within the 3D anatomical image of the subject, thereby creating a 3D segmentation map aligned with the 3D anatomical image of the subject and comprising one or more pelvic bone regions, wherein each pelvic bone region corresponds to a particular pelvic bone and/or group of one or more pelvic bones and identifies a representation of the particular pelvic bone and/or group of one or more pelvic bones within the 3D anatomical image;

(c) receiving, by the processor, a 3D pelvic atlas image comprising:

(A) an identification of one or more pelvic lymph sub-regions in the 3D pelvic atlas image; and (B) an identification of one or more reference pelvic bone regions in the 3D pelvic atlas image, wherein at least a portion of the one or more reference pelvic bone regions in the 3D pelvic atlas image corresponds to one or more of the pelvic bone regions of the 3D segmentation map;

(d) transforming, by the processor, the 3D pelvic atlas image to co-register it with the 3D segmentation map using (i) the one or more reference pelvic bone regions identified within the 3D pelvic atlas image and (ii) the one or more pelvic bone regions of the 3D segmentation map, thereby creating a transformed 3D pelvic atlas image comprising the identified one or more pelvic lymph sub-regions thereby aligned to the 3D anatomical image and segmentation thereof; and (e) determining, by the processor, for each of the one or more hotspots of the 3D functional image, a pelvic lymph classification using the identification of the one or more pelvic lymph sub-regions within the transformed 3D pelvic atlas image, and wherein the method comprises:

performing steps (c) and (d) for a plurality of prospective 3D pelvic atlas images to determine, for each of the prospective 3D pelvic atlas images, a corresponding transformed version and selecting, by the processor, a particular one of the prospective 3D pelvic atlas images as a best-fit 3D pelvic atlas image; and using the transformed version of the best-fit 3D pelvic atlas image as the transformed 3D pelvic atlas image to determine, at step (e), the pelvic lymph classification for each of the one or more hotspots.

20. A system for automatically processing 3D images of a subject to identify and/or characterize cancerous lesions within the subject, the system comprising:

a processor of a computing device; and a memory having instructions stored thereon, wherein the instructions, when executed by the processor, cause the processor to:

(a) receive (i) a 3D functional image of the subject obtained using a functional imaging modality and (ii) a 3D anatomical image of the subject obtained using an anatomical imaging modality, wherein the 3D functional image and the 3D anatomical image are aligned and include a representation of a pelvic region of the subject, and wherein the 3D functional image includes one or more hotspots representing potential lesions within the pelvic region of the subject;

(b) segment the 3D anatomical image of the subject to identify representations of one or more pelvic bones within the 3D anatomical image of the subject, thereby creating a 3D segmentation map aligned with the 3D anatomical image of the subject and comprising one or more pelvic bone regions, wherein each pelvic bone region corresponds to a particular pelvic bone and/or group of one or more pelvic bones and identifies a representation of the particular pelvic bone and/or group of one or more pelvic bones within the 3D anatomical image;

(c) receive a 3D pelvic atlas image comprising:

(A) an identification of one or more pelvic lymph sub-regions in the 3D pelvic atlas image; and (B) an identification of one or more reference pelvic bone regions in the 3D pelvic atlas image, wherein at least a portion of the one or more reference pelvic bone regions in the 3D pelvic atlas image corresponds to one or more of the pelvic bone regions of the 3D segmentation map;

(d) transform the 3D pelvic atlas image to co-register it with the 3D segmentation map using (i) the one or more reference pelvic bone regions identified within the pelvic atlas image and (ii) the one or more pelvic bone regions of the 3D segmentation map, thereby creating a transformed 3D pelvic atlas image comprising the identified one or more pelvic lymph sub-regions thereby aligned to the 3D anatomical image and segmentation thereof; and (e) determine for each of the one or more hotspots of the 3D functional image, a pelvic lymph classification using the identification of the one or more pelvic lymph sub-regions within the transformed 3D pelvic atlas image, and wherein the instructions cause the processor to:

perform steps (c) and (d) for a plurality of prospective 3D pelvic atlas images to determine, for each of the prospective 3D pelvic atlas images, a corresponding transformed version and select, by the processor, a particular one of the prospective 3D pelvic atlas images as a best-fit 3D pelvic atlas image; and use the transformed version of the best-fit 3D pelvic atlas image as the transformed 3D pelvic atlas image to determine, at step (e), the pelvic lymph classification for each of the one or more hotspots.

21. A method for automatically processing 3D images of a subject to identify and/or characterize cancerous lesions within the subject, the method comprising:

(a) receiving, by a processor of a computing device, (i) a 3D functional image of the subject obtained using a functional imaging modality and (ii) a 3D anatomical image of the subject obtained using an anatomical imaging modality, wherein the 3D functional image and the 3D anatomical image are aligned and include a representation of a pelvic region of the subject, and wherein the 3D functional image includes one or more hotspots representing potential lesions within the pelvic region of the subject;

(b) segmenting, by the processor, the 3D anatomical image of the subject to identify representations of one or more pelvic bones within the 3D anatomical image of the subject, thereby creating a 3D segmentation map aligned with the 3D anatomical image of the subject and comprising one or more pelvic bone regions, wherein each pelvic bone region corresponds to a particular pelvic bone and/or group of one or more pelvic bones and identifies a representation of the particular pelvic bone and/or group of one or more pelvic bones within the 3D anatomical image;

(c) receiving, by the processor, a 3D pelvic atlas image comprising:

(A) an identification of one or more pelvic lymph sub-regions in the 3D pelvic atlas image; and (B) an identification of one or more reference pelvic bone regions in the 3D pelvic atlas image, wherein at least a portion of the one or more reference pelvic bone regions in the 3D pelvic atlas image corresponds to one or more of the pelvic bone regions of the 3D segmentation map;

(d) transforming, by the processor, the 3D pelvic atlas image to co-register it with the 3D segmentation map using (i) the one or more reference pelvic bone regions identified within the pelvic atlas image and (ii) the one or more pelvic bone regions of the 3D segmentation map, thereby creating a transformed 3D pelvic atlas image comprising the identified one or more pelvic lymph sub-regions thereby aligned to the 3D anatomical image and segmentation thereof; and (e) determining, by the processor, for each of the one or more hotspots of the 3D functional image, a pelvic lymph classification using the identification of the one or more pelvic lymph sub-regions within the transformed 3D pelvic atlas image, and wherein the method comprises:

receiving, at step (c), a plurality of prospective 3D pelvic atlas images;

at step (d):

for each particular one of the plurality of prospective 3D pelvic atlas images, determining a first registration transformation to co-register the particular prospective 3D pelvic atlas image with the 3D segmentation map using (i) the one or more reference pelvic bone regions identified within the particular prospective 3D pelvic atlas image and (ii) the one or more pelvic bone regions of the 3D segmentation map and transforming the particular prospective 3D pelvic atlas image according to the first registration transformation, thereby creating a plurality of transformed prospective pelvic atlas images;

selecting a particular one of the transformed prospective pelvic atlas images as an initial best-fit pelvic atlas image; and determining, for the initial best-fit pelvic atlas image, a second registration transformation to refine the co-registration of the initial best-fit pelvic atlas image with the 3D segmentation map using (i) the one or more reference pelvic bone regions identified within initial best-fit pelvic atlas image and (ii) the one or more pelvic bone regions of the 3D segmentation map and transforming the initial best-fit pelvic atlas image according to the second registration transformation, thereby creating a final transformed pelvic atlas image; and using the final transformed pelvic atlas image as the transformed 3D pelvic atlas image to determine, at step (e), the pelvic lymph classification for each of the one or more hotspots.

22. A system for automatically processing 3D images of a subject to identify and/or characterize cancerous lesions within the subject, the system comprising:

a processor of a computing device; and a memory having instructions stored thereon, wherein the instructions, when executed by the processor, cause the processor to:

(a) receive (i) a 3D functional image of the subject obtained using a functional imaging modality and (ii) a 3D anatomical image of the subject obtained using an anatomical imaging modality, wherein the 3D functional image and the 3D anatomical image are aligned and include a representation of a pelvic region of the subject, and wherein the 3D functional image includes one or more hotspots representing potential lesions within the pelvic region of the subject;

(b) segment the 3D anatomical image of the subject to identify representations of one or more pelvic bones within the 3D anatomical image of the subject, thereby creating a 3D segmentation map aligned with the 3D anatomical image of the subject and comprising one or more pelvic bone regions, wherein each pelvic bone region corresponds to a particular pelvic bone and/or group of one or more pelvic bones and identifies a representation of the particular pelvic bone and/or group of one or more pelvic bones within the 3D anatomical image;

(c) receive a 3D pelvic atlas image comprising:

(A) an identification of one or more pelvic lymph sub-regions in the 3D pelvic atlas image; and (B) an identification of one or more reference pelvic bone regions in the 3D pelvic atlas image, wherein at least a portion of the one or more reference pelvic bone regions in the 3D pelvic atlas image corresponds to one or more of the pelvic bone regions of the 3D segmentation map;

(d) transform the 3D pelvic atlas image to co-register it with the 3D segmentation map using (i) the one or more reference pelvic bone regions identified within the pelvic atlas image and (ii) the one or more pelvic bone regions of the 3D segmentation map, thereby creating a transformed 3D pelvic atlas image comprising the identified one or more pelvic lymph sub-regions thereby aligned to the 3D anatomical image and segmentation thereof; and (e) determine for each of the one or more hotspots of the 3D functional image, a pelvic lymph classification using the identification of the one or more pelvic lymph sub-regions within the transformed 3D pelvic atlas image, and wherein the instructions cause the processor to:

receive, at step (c), a plurality of prospective 3D pelvic atlas images;

at step (d):

for each particular one of the plurality of prospective 3D pelvic atlas images, determine a first registration transformation to co-register the particular prospective 3D pelvic atlas image with the 3D segmentation map using (i) the one or more reference pelvic bone regions identified within the particular prospective 3D pelvic atlas image and (ii) the one or more pelvic bone regions of the 3D segmentation map and transform the particular prospective 3D pelvic atlas image according to the first registration transformation, thereby creating a plurality of transformed prospective pelvic atlas images;

select a particular one of the transformed prospective pelvic atlas images as an initial best-fit pelvic atlas image; and determine, for the initial best-fit pelvic atlas image, a second registration transformation to refine the co-registration of the initial best-fit pelvic atlas image with the 3D segmentation map using (i) the one or more reference pelvic bone regions identified within initial best-fit pelvic atlas image and (ii) the one or more pelvic bone regions of the 3D segmentation map and transform the initial best-fit pelvic atlas image according to the second registration transformation, thereby creating a final transformed pelvic atlas image; and use the final transformed pelvic atlas image as the transformed 3D pelvic atlas image to determine, at step (e), the pelvic lymph classification for each of the one or more hotspots.

*    *    *    *    *